United States Patent
Sahin et al.

(10) Patent No.: US 10,745,477 B2
(45) Date of Patent: *Aug. 18, 2020

(54) ANTIBODIES SPECIFIC FOR CLAUDIN 6 (CLDN6)

(71) Applicants: Ganymed Pharmaceuticals AG, Mainz (DE); Johannes Gutenberg-Universitat Mainz, Mainz (DE)

(72) Inventors: Ugur Sahin, Mainz (DE); Özlem Türeci, Mainz (DE); Michael Koslowski, Frankfurt (DE); Korden Walter, Wiesbaden (DE); Stefan Woll, Nackenheim (DE); Maria Kreuzberg, Mainz (DE); Bernd Hubner, Munich (DE); Michael Erdeljan, Hochheim am Main (DE)

(73) Assignees: Ganymed Pharmaceuticals GmbH, Mainz (DE); Johannes Gutenberg-Universitat Mainz, Mainz (DE)

( * ) Notice: Subject to any disclaimer, the term of this patent is extended or adjusted under 35 U.S.C. 154(b) by 291 days.

This patent is subject to a terminal disclaimer.

(21) Appl. No.: 15/885,454

(22) Filed: Jan. 31, 2018

(65) Prior Publication Data

US 2018/0162938 A1     Jun. 14, 2018

Related U.S. Application Data

(63) Continuation of application No. 15/133,783, filed on Apr. 20, 2016, now Pat. No. 9,932,401, which is a continuation of application No. 13/503,461, filed as application No. PCT/EP2010/006888 on Nov. 11, 2010, now Pat. No. 9,487,584.

(60) Provisional application No. 61/361,618, filed on Jul. 6, 2010, provisional application No. 61/260,202, filed on Nov. 11, 2009.

(30) Foreign Application Priority Data

Nov. 11, 2009 (EP) .................... 09014136
Jul. 6, 2010 (EP) .................... 10006956

(51) Int. Cl.

| C07K 14/47 | (2006.01) |
| C07K 14/725 | (2006.01) |
| A61K 39/00 | (2006.01) |
| G01N 33/50 | (2006.01) |
| G01N 33/569 | (2006.01) |
| G01N 33/574 | (2006.01) |
| C07K 14/705 | (2006.01) |
| C07K 14/74 | (2006.01) |
| C07K 16/38 | (2006.01) |
| A61K 35/17 | (2015.01) |
| C07K 16/28 | (2006.01) |
| C07K 16/30 | (2006.01) |

(52) U.S. Cl.
CPC ............. *C07K 16/28* (2013.01); *C07K 16/30* (2013.01); *A61K 2039/505* (2013.01); *C07K 2317/14* (2013.01); *C07K 2317/24* (2013.01); *C07K 2317/33* (2013.01); *C07K 2317/34* (2013.01); *C07K 2317/52* (2013.01); *C07K 2317/56* (2013.01); *C07K 2317/565* (2013.01); *C07K 2317/73* (2013.01); *C07K 2317/732* (2013.01); *C07K 2317/734* (2013.01)

(58) Field of Classification Search
None
See application file for complete search history.

(56) References Cited

U.S. PATENT DOCUMENTS

| 4,946,778 A | 8/1990 | Ladner et al. |
| 5,624,821 A | 4/1997 | Winter et al. |
| 5,648,260 A | 7/1997 | Winter et al. |
| 6,121,022 A | 9/2000 | Presta et al. |
| 6,194,551 B1 | 2/2001 | Idusogie et al. |
| 6,277,375 B1 | 8/2001 | Ward |
| 7,431,927 B2 | 10/2008 | Couto et al. |
| 9,321,842 B2 | 4/2016 | Sahin et al. |
| 9,487,584 B2 | 11/2016 | Sahin et al. |
| 9,718,886 B2 | 8/2017 | Sahin et al. |
| 10,233,253 B2 * | 3/2019 | Sahin ............ C07K 16/28 |
| 10,370,423 B2 * | 8/2019 | Sahin ............ G01N 33/574 |
| 2002/0086356 A1 | 7/2002 | Tuschl et al. |

(Continued)

FOREIGN PATENT DOCUMENTS

| CA | 2379661 A1 | 9/2003 |
| CN | 101312989 A | 11/2008 |

(Continued)

OTHER PUBLICATIONS

ISR for PCT/EP2014/066330 dated Nov. 17, 2014.

(Continued)

*Primary Examiner* — Julie Wu
(74) *Attorney, Agent, or Firm* — Neal, Gerber & Eisenberg LLP; Kevin A. O'Connor

(57) ABSTRACT

The present invention provides antibodies useful as therapeutics for treating and/or preventing diseases associated with cells expressing Claudin-6 (CLDN6), including tumor-related diseases such as ovarian cancer, lung cancer, gastric cancer, breast cancer, hepatic cancer, pancreatic cancer, skin cancer, malignant melanoma, head and neck cancer, sarcoma, bile duct cancer, cancer of the urinary bladder, kidney cancer, colon cancer, placental choriocarcinoma, cervical cancer, testicular cancer, and uterine cancer.

19 Claims, 30 Drawing Sheets

Specification includes a Sequence Listing.

(56) References Cited

U.S. PATENT DOCUMENTS

| | | |
|---|---|---|
| 2002/0127584 A1 | 9/2002 | Baker et al. |
| 2003/0017534 A1 | 1/2003 | Buelow et al. |
| 2003/0118592 A1 | 6/2003 | Ledbetter et al. |
| 2003/0133939 A1 | 7/2003 | Ledbetter et al. |
| 2007/0082345 A1 | 4/2007 | Ota et al. |
| 2011/0059469 A1 | 3/2011 | Aburatani et al. |
| 2011/0300144 A1 | 12/2011 | Sahin et al. |
| 2013/0183305 A1 | 7/2013 | Sahin et al. |
| 2014/0127219 A1 | 5/2014 | Sahin et al. |
| 2016/0264677 A1 | 9/2016 | Sahin et al. |
| 2019/0055311 A1* | 2/2019 | Sahin ............... C07K 16/30 |

FOREIGN PATENT DOCUMENTS

| | | |
|---|---|---|
| CN | 101687929 A | 3/2010 |
| EP | 338841 A1 | 10/1989 |
| EP | 1067182 A2 | 1/2001 |
| EP | 1242443 A1 | 9/2002 |
| EP | 1578996 A2 | 9/2005 |
| EP | 1594447 A2 | 11/2005 |
| EP | 2011886 A2 | 1/2009 |
| EP | 2241578 A1 | 10/2010 |
| EP | 2322555 A1 | 5/2011 |
| JP | H11503014 A | 3/1999 |
| JP | 2001506275 A | 5/2001 |
| JP | 2002536995 A | 11/2002 |
| JP | 2004537534 A | 12/2004 |
| JP | 2007529416 A | 10/2007 |
| JP | 2011501758 A | 1/2011 |
| JP | 2011516580 A | 5/2011 |
| JP | 2012512778 A | 6/2012 |
| JP | 2012518608 A | 8/2012 |
| JP | 2012518609 A | 8/2012 |
| WO | 8704462 A1 | 7/1987 |
| WO | 8901036 A1 | 2/1989 |
| WO | 9204381 A1 | 3/1992 |
| WO | 9633265 A1 | 10/1996 |
| WO | 9633739 A1 | 10/1996 |
| WO | 9924463 A2 | 5/1999 |
| WO | 9945962 A1 | 9/1999 |
| WO | 0012708 A2 | 3/2000 |
| WO | 0035937 A1 | 6/2000 |
| WO | 0073348 A2 | 12/2000 |
| WO | 0078961 A1 | 12/2000 |
| WO | 0151513 A2 | 7/2001 |
| WO | 0153312 A1 | 7/2001 |
| WO | 0193983 A1 | 12/2001 |
| WO | 0200690 A2 | 1/2002 |
| WO | 0208284 A2 | 1/2002 |
| WO | 0208288 A2 | 1/2002 |
| WO | 0243478 A2 | 6/2002 |
| WO | 2004030615 A2 | 4/2004 |
| WO | 2004035607 A2 | 4/2004 |
| WO | 2004060270 A2 | 7/2004 |
| WO | 2005005601 A2 | 1/2005 |
| WO | 2006033664 A1 | 3/2006 |
| WO | 2008114733 A1 | 9/2008 |
| WO | 2009025759 A1 | 2/2009 |
| WO | 2009028663 A1 | 3/2009 |
| WO | 2009087978 A1 | 7/2009 |
| WO | 2010043650 A2 | 4/2010 |
| WO | 2010094499 A1 | 8/2010 |
| WO | 2011057788 A1 | 5/2011 |
| WO | 2012003956 A1 | 1/2012 |
| WO | 2013087929 A2 | 6/2013 |
| WO | 2014015148 A1 | 1/2014 |

OTHER PUBLICATIONS

Jones, P. et al. (1986) Nature 321: 522-525.
K. Morita et al., "Endothelial claudin: Claudin-5/TMVCF constitutes tight junction strands in endothelial cells," The Journal of Cell Biology, vol., 147, No. 1, Oct. 4, 1999, pp. 185-194, XP002239048.
Kessels et al., Nat Immunol. 2:957-61, 2001.
Klimka et al., British Journal of Cancer, 2000, 83:252-260.
Kohler and Milstein, Nature 256: 495 (1975).
Kohler, "Immunoglobulin chain loss in hybridoma lines," Proc. Natl. Acad. Sci. USA, vol. 77, No. 4, pp. 2197-2199, Apr. 1980.
Koslowski et al, 2006.
Koslowski et al, Cancer Research, American Association for Cancer Research, Baltimore, MD, vol. 67, No. 19, pp. 9528-9534 (Oct. 1, 2007).
Kozak, 1991, J. Biol. Chem. 266: 19867-19870.
Kraeft et al, Clin Cancer Res 10: 3020-8, 2004.
Kraus et al., in Methods in Molecular Biology series, Recombinant antibodies for cancer therapy ISBN-0-89603-918-8 (2003).
Krieg et al., 1995, Nature 374: 546-549.
Kuby, Janis Immunology, W. H. Freeman and Company New York, N Y (1992).
Kwon, M., "Emerging Roles of Claudins in Human Cancer," International Journal of Molecular Science, vol. 14, No. 9, Sep. 4, 2013, XP055107170, pp. 18148-18180.
Lamminmaki et al. (Journal of Biological Chemistry, 2001, 276:36687-36694).
Landor M. (1995) Maternal-fetal transfer of immunoglobulins, Ann. Allergy Asthma Immunol. 74: 279-283.
Lu et al (2004) Clinical Cancer Research vol. 10: 3291-3300.
Maloy et al., Proc Natl Acad Sci USA 98:3299-303,2001.
Matz et al. (Nucleic Acids Research, 1999, vol. 27, No. 6, 1558).
Merrifield, R.B. Solid-Phase Peptide Synthesis. III. An Improved Synthesis of Bradykinin, Biochemistry, 3:1385-90, 1964 (1964).
Ming-Ming Tsai, "Potential prognostic, diagnostic and therapeutic markers for human gastric cancer", World Journal of Gastroenterology, vol. 20, No. 38, Oct. 14, 2014 (Oct. 14, 2014), p. 13791.
Monteiro, R. C. et al. (1992) J.Immunol. 148: 1764.
Morris, Glenn E., Epitope Mapping Protocols (Methods in Molecular Biology) ISBN 089603-375-9, (1996).
Morrison, S. (1985) Science 229: 1202.
Morton, H. C. et al. (1996) Critical Reviews in Immunology 16: 423-440.
NCBI, Homo sapiens claudin 6 (CLDN6), mRNA, May 1, 2015, 4 pages.
Neddleman and Wunsch, 1970, J. Mol. Biol. 48, 443.
Neefjes et al., Nature Reviews, Immunology, vol. 11, pp. 823-836 (Dec. 2011).
Order, Stanley, pp. 303-316 (1985); "Analysis, Results, and Future Prospective of the Therapeutic Use of Radiolabeled Antibody in Cancer Therapy", in Monoclonal Antibodies for Cancer Detection and Therapy.
Osanai Makoto et al., "Epigenetic silencing of claudin-6 promotes anchorage-independent growth of breast carcinoma cells" Cancer Science Oct. 2007, vol. 98, No. 10, pp. 1557-1562, XP002547907.
Ossendorp et al., Immunol Lett. 74:75-9, 2000.
Ossendorp et al., J. Exp. Med. 187:693-702, 1998.
Ozturk, et al., "Loss of Antibody Productivity During Long-Term Cultivation of a Hybridoma Cell Line in Low Serum and Serum-Free Media," Hybridoma, vol. 9, No. 2, 1990.
Padlan et al. (Proceedings of the National Academy of Sciences, 1989, 86:5938-5942).
Pakula A. A. et al., Genetic analysis of protein stability and function. Annu. Rev. Genet., 1989 No. 23, pp. 289-310.
Pascalis et al. (The Journal of Immunology, 2002, 169, 3076-3084).
PCT International Bureau, International Preliminary Report on Patentability for Application No. PCT/EP2010/006888, dated May 15, 2010.
Pearson and Lipman, 1988, Proc. Natl Acad. Sci. USA 85, 2444.
Poljak, R. J., et al. (1994) Structure 2: 1121-1123.
Pollock, et al. (1999) J. Immunol. Meth. 231: 147-157.
Prat, A. et al., "Phenotypic and Molecular Characterization of the Claudin-Low Intrinsic Subtype of Breast Cancer," Breast Cancer Research, Current Science, London, GB, vol. 12, No. 5, Sep. 2, 2010, XP021085380, p. R68.
Queen, C. et al. (1989) Proc. Natl. Acad. Sci. U. S. A. 86:10029-10033.
Reddehase et al., Nature vol. 337, pp. 651-653 (Feb. 1989).
Reisfeld et al. (eds. ), pp. 243-56 (Alan R. Liss, Inc. 1985).

(56) References Cited

OTHER PUBLICATIONS

Remington: The Science and Practice of Pharmacy, 19th Edition, Gennaro, Ed., Mack Publishing Co., Easton, PA, 1995.
Riechmann, L. et al. (1998) Nature 332: 323-327.
Robinson et al. (eds.), pp. 623-53 (Marcel Dekker, Inc. 1987).
Robinson, J.R., ed. Sustained and Controlled Release Drug Delivery Systems, Marcel Dekker, Inc., New York, 1978.
Roitt, I. (1991), Essential Immunology, 7th Edition, Blackwell Scientific Publications, Oxford.
Allard et al., Clinical Cancer Research, 10:6897-904, 2004.
Almagro & Fransson, Frontiers in Bioscience 2008; 13:1619-33.
Altman et al., Science, 274:94-96, 1996.
Anderson et al., 1. Immunol. 143: 1899-1904, 1989.
Anonymous, "Tumor Markers—National Cancer Institute", Dec. 7, 2011 (Dec. 7, 2011), Retrieved from the Internet: URL:http://www.cancer.gov/cancertopics/diagnosis-staging/diagnosis/tumor-markers-fact-sheet [retrieved on Mar. 20, 2015].
Arabzadeh et al., "Changes in the distribution pattern of Caludin tight junction proteins during the progression of mouse skin tumorigenesis," BMC Cancer, vol. 7, Oct. 18, 2007, p. 196, XP021034484.
Arabzadeh, et al., "Role of the Cldn6 Cytoplasmic Tail Domain in Membrane Targeting and Epidermal Differentiation In Vivo," Molecular and Cellular Biology, vol. 26(15), Aug. 2006.
Babcook et al., Proc. Natl. Acad. Sci, USA, vol. 93, pp. 7843-7848, Jul. 1996; A novel strategy for generating monoclonal antibodies from single, isolated lymphocytes producing antibodies of defined strategy.
Baldwin et al. (eds.), pp. 303-16 (Academic Press 1985).
Barthelemy et al. (Journal of Biological Chemistry, 2008, 283:3639-3654).
Beadling et al., Nature Medicine, 12:1208 (2006).
Beiboer et al. (Journal of Molecular Biology, 2000, 296:833-849).
Benny K.C. Lo Antibody Engineering ISBN 1-58829-092-1, 2004.
Berge, S. M., et al. (1977) J. Pharm. Sci. 66: 1-19.
Berzofsky et al., "Antibody-Antigen Interactions" In Fundamental Immunology, Paul, W. E., Ed., Raven Press New York, NY (1984).
Bird et al. (1988) Science 242: 423-426.
Casset et al. (Biochemical and Biophysical Research Communications, 2003, 307:198-205).
Chen et al. (Journal of Molecular Biology, 1999, 293:865-881).
Choi et al., 2011, Molecular Biosystems, 2011, 7:3327-334.
Clark, W.R. (1986), The Experimental Foundations of Modern Immunology.
Cristofanilli et al, N Eng. J Med 351: 781-91, 2004.
Cunningham-Rundles et al., (1992) Biological activities of polyethyleneglycol immunoglobulin conjugates J. Immunol. Methods, 152: 177-190.
David U., et al., "Immunologic and Chemical Targeting of the Tight-Junction Protein Claudin-6 Eliminates Tumorigenic Human Pluripotent Stem Cells," Natural Communications 2013, vol. 4, Jun. 18, 2013, XP008168176, p. 1992.
De Genst et al., Developmental and Comparative Immunology, 2006, 30:187-98.
Documentation of Affymetrix probe set "75948_AT" (2000).
Dormeyer, W. et al., "Plasma Membrane Proteomics of Human Embryonic Stem Cells and Human Embroyonal Carcinoma Cells," Journal of Proteome Research, American Chemical Society, Washington, DC., US, vol. 7, KP002599270, Jul. 3, 2008, pp. 2936-2951.
Dunbar et al., Curro Biol. 8:413-416, 1998.
European Search Report corresponding to European Patent Application Serial No. 09014136.7 dated Mar. 23, 2010.
Extended European Search Report for 10006957.4-2406 dated Nov. 10, 2010.
Extended European Search Report for European Patent Application No. 09002452.2- 1212, dated Oct. 22, 2009.
Fischer, R., et al. (1999) Biol. Chem. 380: 825-839.
Gardsvoll, J. Immunol. Methods 234: 107-116, 2000.
GenBank. Homo sapiens claudin 6 (CLDN6), mRNA NCB I Reference Sequence: NM_021195.4, 2014.
Goodman and Gilman, "The Pharmacological Basis of Therapeutics", 8th Edition, 1990, McGraw-Hill, Inc., in particular Chapter 52 (Antineoplastic Agents (Paul Calabresi and Bruce A. Chabner.
Griffiths et al. (The EMBO Journal, 1993, 12:725-734).
Hall et al., Science 268: 1432-1434 (1995).
Harlow et al., "Antibodies: A Laboratory Manual", ISBN 0879693142 (1988).
Harlow et al., "Using Antibodies: A Laboratory Manual: Portable Protocol NO", ISBN 0879695447 (1999).
Hellstrom et al., "Antibodies for Drug Delivery", in Controlled Drug Delivery (2nd Ed.) (1987).
Hewitt et al., "The claudin gene family: expression in normal and neoplastic tissdues." BMC Cancer, Biomed Central. vol. 6, No. 1, Jul. 12, 2006. XP021016181.
Holliger, P., et al. (1993) Proc. Natl. Acad. Sci. USA 90: 6444-6448.
Hong Yeon-Hee et al., "Up-regulation of the claudin-6 gene in adipongenesis." Bioscience Biotechnology, and Biochemistry, Nov. 2005, vol. 69, No. 11, pp. 2117-2121, XP002547908.
Huang Yu-Hung et al., "Claudin-3 gene silencing with siRNA suppresses ovarian tumor growth and metastasis." Proceedings of the National Academy of Sciences of the United States of America 3, Mar. 2009, vol. 106, No. 9, Feb. 10, 2009, pp. 3426-3430, XP002547909.
Huston et al. (1988) Proc. Natl. Acad. Sci. USA 85: 5879-5883.
Iacobuzio-Donahue et al. Amer. Journ. Pathology, vol. 160, No. 4, pp. 1239-1249 Apr. 2002.
International Search Report and Written Opinion corresponding to International Patent Application No. PCT/EP2010/006888, dated Feb. 4, 2011.
IPRP for PCT/EP2010/001062, dated Sep. 1, 2011.
IPRP for PCT/EP2012/001721 dated Nov. 19, 2013.
ISR & WO for PCT/EP2011/003312, dated Oct. 5, 2011.
ISR for PCT/EP2012/001721 dated Jul. 25, 2012.
U.S. Appl. No. 15/133,783, filed Apr. 20, 2016.
U.S. Appl. No. 13/503,461, filed Aug. 13, 2012.
U.S. Appl. No. 13/201,702, Publication No. US 2011/0300144 A1, U.S. Pat. No. 9,809,815.
U.S. Appl. No. 15/726,063.
U.S. Appl. No. 13/503,461, Publication No. US 2012/0308478 A1, U.S. Pat. No. 9,487,584.
U.S. Appl. No. 15/133,783, Publication No. US 2016/0222125 A1, U.S. Pat. No. 9,932,401.
U.S. Appl. No. 13/808,423, Publication No. US 2013/0183305 A1, U.S. Pat. No. 9,718,886.
U.S. Appl. No. 15/206,039, Publication No. US 2016/0355604 A1, U.S. Pat. No. 9,902,778.
U.S. Appl. No. 15/866,139.
U.S. Appl. No. 14/117,118, Publication No. US 2014/0127219 A1, U.S. Pat. No. 9,321,842.
U.S. Appl. No. 15/076,536, Publication No. US 2016/0264677 A1.
U.S. Appl. No. 14/904,011, Publication No. US 2016/0159901 A1.
Rossi et al., Am. J. Clin. Pathol. 124: 295 (2005).
Rudikoff et al. (Proceedings of the National Academy of Science USA, 1982, 79-1979).
Sambrook et al., Molecular Cloning: A Laboratory Manual, 2nd Edition, Cold Spring Harbor Laboratory Cold Spring Harbor, New York, 1989.
Satohisa et al. (Experimental Cell Research, 2005: 310-66-78).
Scatchard et al., Ann N. Y. Acad. Sci, 51 :660 (1949).
Sela-Culang, et al., "The structural basis of antibody-antigen recognition," Frontiers in Immunology, vol. 4, Article 302, Oct. 8, 2013.
Shepard et al., "Monoclonal Antibodies: A Practical Approach", ISBN 0-19-963722-0 (2000).
Shield et al. (2002) JBC, 277: 26733.
Smirnov et al, Cancer Res 65: 4993-7, 2005.
Smith and Waterman, 1981, Ads App. Math. 2, 482.
So et al., 1997, Mol. Cells 7: 178-186.
Spieker-Polet et al., Proc. Natl. Acad. Sci. U.S.A. 92:9348 (1995).
Stanislawski et al., Nat Immunol. 2:962-70, 2001.
Strejan et al. (1984) J. Neuroimmunol. 7: 27.
Thorpe et al., "The Preparation and Cytotoxic Properties of Antibody-Toxin Conjugates", Immunol. Rev., 62: 119-58 (1982).

(56) References Cited

OTHER PUBLICATIONS

Thorpe, Antibody Carriers of Cytotoxic Agents in Cancer Therapy: A Review, in Monoclonal Antibodies '84: Biological and Clinical Applications (1985).
Trail, P., "Antibody Drug Conjugates as Cancer Therapeutics," Antibodies, M D P I AG, CH, vol. 2, No. 1, Feb. 27, 2013, XP002725437, pp. 113-129.
Turksen, K., "Claudins and Cancer Stem Cells," Stem Cell Reviews and Reports, Humana Press Inc., New York, vol. 1, No. 4, Apr. 28, 2011, XP019985913, pp. 797-798.
Tuschl T. et al., "The siRNA User Guide", revised Oct. 11, 2002.
Ushiku T. et al., "Distinct Expression Pattern of Claudin-6, a Primitive Phenotypic Tight Junction Molecule, In Germ Cell Tumours and Visceral Carcinomas," Histopatology, vol. 61, No. 6, Jul. 17, 2012, XP055107355, pp. 1043-1056.
Vajdos F. F. et al., Comprehensive Functional Maps of the Antigenbinding Site of an Anti-ErbB2 Antibody Obtained with Shotgun Scanning Mutagenesis, J. Mol. Biol., 2002, vol. 320, pp. 415-428.
Verma, R., et al. (1998) J. Immunol. Meth. 216: 165-181.
Wang, L. et al., "Claudin 6: A Novel Surface Marker for Characterizing Mouse Pluripotent Stem Cells," Cell Research, vol. 22, No. 6, May 8, 2012, XP055107350, pp. 1082-1085.
Ward et al. (Nature, 1989, 341 :544-546).
Welschof and Kraus, Recombinant antibodes for cancer therapy ISBN-0-89603-918-8 (2003).
Westwood, O. et al. Epitope Mapping: A Practical Approach Practical Approach Series, 248 (Mar. 2001).
Wu, et al., "Humanization of a Murine Monoclonal Antibody by Simultaneous Optimization of Framework and CDR Residues," Journal of Molecular Biology, 294, 1999.
Xu, et al., "Diversity in the CDR3 Region of VH Is Sufficient for Most Antibody Specificities," Immunity, vol. 13, No. 1, Jul. 2000.
Yuan et al. (Cytotherapy 8:498, 2006).

\* cited by examiner

Fig. 1

```
                                                                                          Extracellular Loop 1
CLDN6 (SEQ ID NO: 2)   MASAGMQILGVVLTLLGWVNGLVSCALPMWRVTAFIGNSIVVAQVVWEGLWMSCVVQSTG   60
CLDN9 (SEQ ID NO: 9)   MASTGLELLGMTLAVLGWLGTIVSCALPMWKVTAFIGNSIVVAQVVWEGLMWSCVVQSTG   60
CLDN4 (SEQ ID NO: 10)  MASMGLQVMGIALAVLGWLAVMLCCALPMWRVTAFICSNIVTSQTIWEGLWMNCVVQSTG   60
CLDN3 (SEQ ID NO: 11)  -MSMGLEITGTALAVLGWLGTIVCCALPMWRVSAFIGSNIITSQNIWEGLWMNCVVQSTG   59
                        *  *: . ::*::***:. :: ********:.:*:  .::.*: *****:**:******

CLDN6 (SEQ ID NO: 2)   QMQCKVYDSLLALPQDLQAARALCVIALLVALFGLLVYLAGAKCTTCVEEKDSKARLVLT  120
CLDN9 (SEQ ID NO: 9)   QMQCKVYDSLLALPQDLQAARALCVIALLVALLALLGLLVATTGAQCTTCVEDEGAKARIVLT  120
CLDN4 (SEQ ID NO: 10)  QMQCKVYDSLLALPQDLQAARALVIISITVAALGVLLSVVGGKCTNCLEDESAKAKTMIV  120
CLDN3 (SEQ ID NO: 11)  QMQCKVYDSLLALPQDLQAARALIVVAIILAAPGLLVAVLVGAQCTNCVQDDTANAKITIV  119
                       ***********************: ::::::** ::: : :  :.:** *.:: ..*: :

Extracellular Loop 2
CLDN6 (SEQ ID NO: 2)   SGIVFVISGVLTLIPVCWTAHAIIRDFYNPLVAEAQKRELGASLYLGWAASGLLLLGGGL  180
CLDN9 (SEQ ID NO: 9)   AGVILLAGILVILIPVCWTAHAITQDFYNPLVAEALKRELGASLYLGWAAAALLMLGGGL  180
CLDN4 (SEQ ID NO: 10)  AGVFLLAGLMVIVPVSWTAHNIIQDFYNPLVASGQKREMGASLYVGWAASGLLVGGGL  180
CLDN3 (SEQ ID NO: 11)  AGVIFLLAALLTIVPVSWSANTIIRDFYNPVVPEAQKRGAGLIVGWAAAALQLLGGAL  179
                        *:::*. :: :: ** *:*: .:**** .*. :* ***:: **  :*:***.:

CLDN6 (SEQ ID NO: 2)   LCCTCPSGGSQGPSHYMARYSTSAPAISRGPSEYP------TSNYV  220
CLDN9 (SEQ ID NO: 9)   LCCTCPPPQVERPRG--PRLGYSIPSRS-GASGLD-----KRDYV  217
CLDN4 (SEQ ID NO: 10)  LCCNCPERT---DKPYSAK----YSAARSAAASN------YV  209
CLDN3 (SEQ ID NO: 11)  LCCSCPPR----EKKYTATKVVYSAPRSTGPGASLGTGYDRKDYV  220
                       ***.**.:                                 *:
```

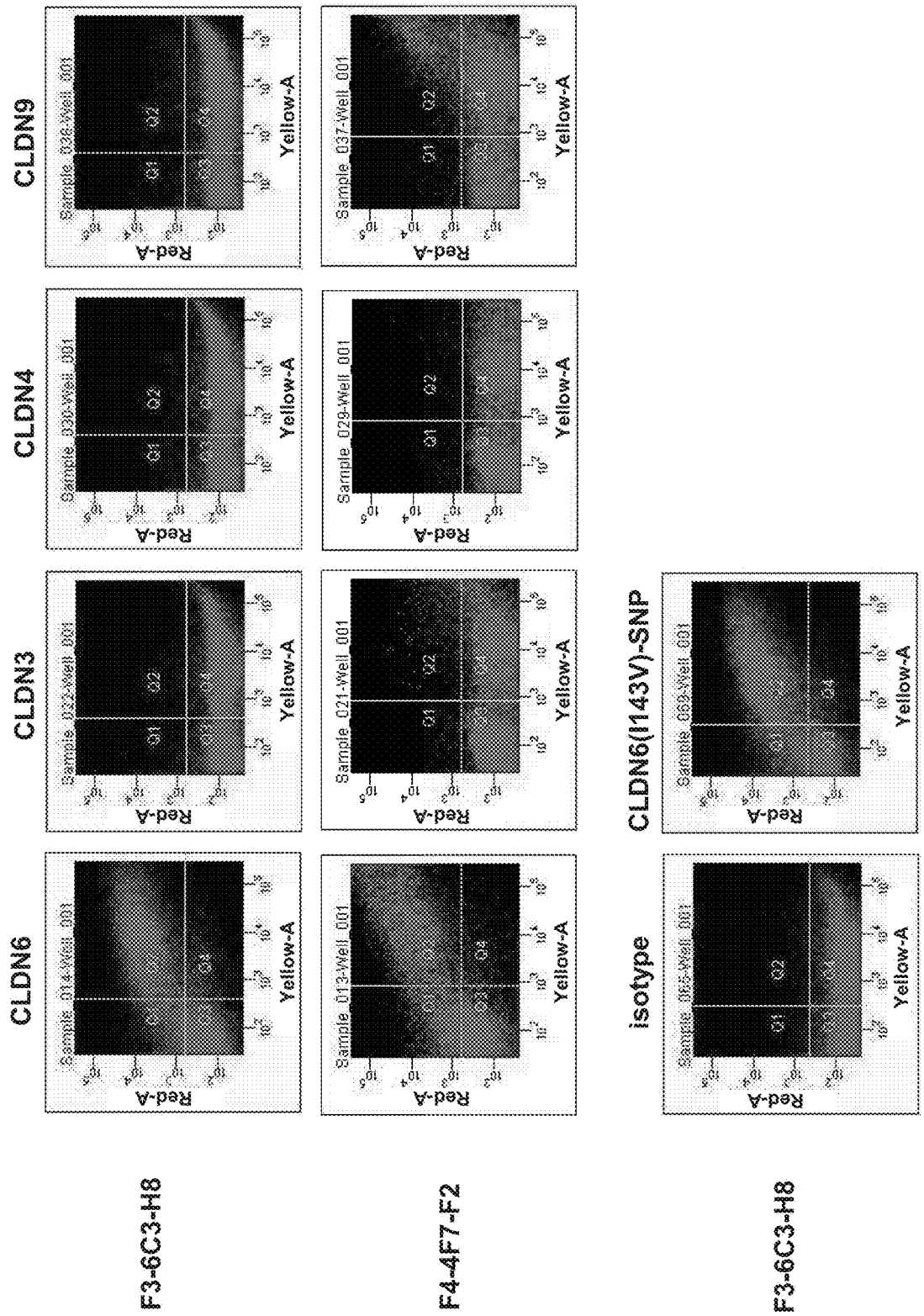

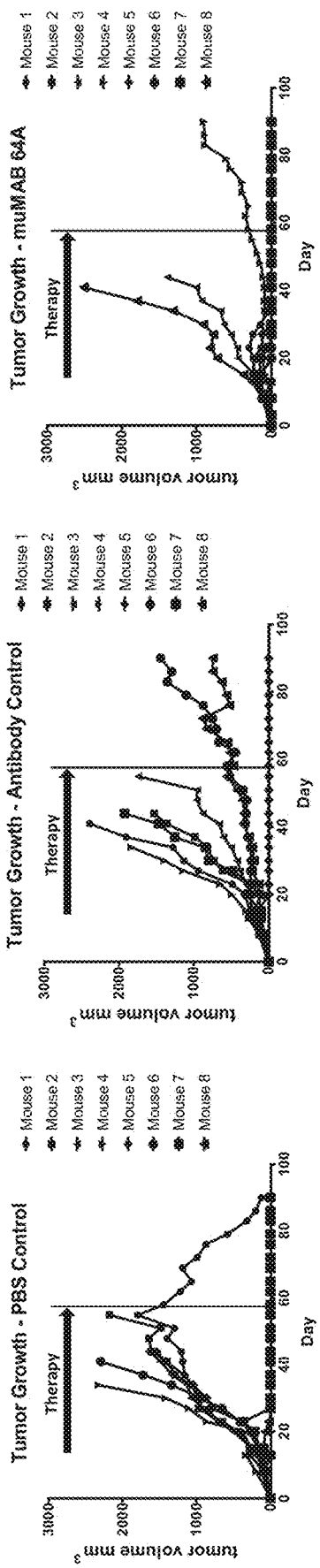
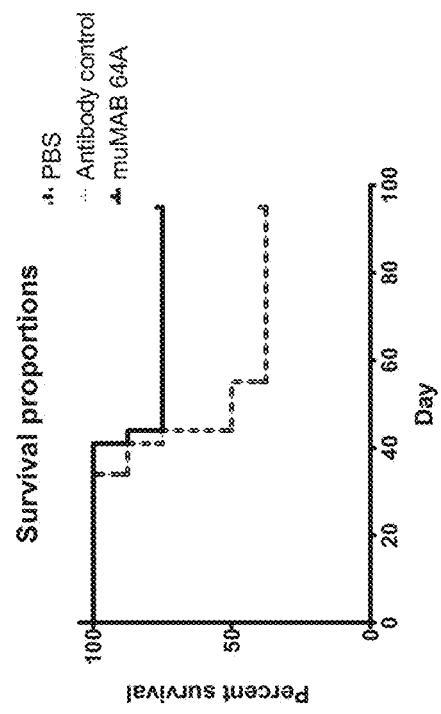
Fig. 20A
Fig. 20B

| Name | L 27 | P 28 | M 29 | W 30 | K 31 | V 32 | T 33 | A 34 | F 35 | I 36 | I 37 | G 38 | N 39 | S 40 | I 41 | V 42 | V 43 | A 44 | Q 45 | V 46 | V 47 | W 48 | E 49 | G 50 | L 51 | W 52 | M 53 | S 54 | C 55 | V 56 | V 57 | Q 58 | S 59 | T 60 | G 61 | Q 62 | M 63 | Q 64 | C 65 | K 66 | V 67 | V 68 | Y 69 | D 70 | S 71 | L 72 | L 73 | A 74 | L 75 | P 76 | Q 77 | D 78 | L 79 | Q 80 | A 81 | A | R |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| GT512chimAB 61D |  | X |  |  |  |  |  |  |  |  |  |  |  |  |  |  |  |  |  |  |  |  |  |  |  |  |  |  |  |  |  |  |  |  |  |  |  |  |  |  |  |  |  |  |  |  |  |  |  |  |  |  |  |  |  |  |
| GT512chimAB 64A |  | X |  |  |  |  |  |  |  | ■ | ■ | ■ | ■ |  |  |  |  |  |  |  |  |  | X | X | X | X | X | X |  |  |  |  |  |  |  |  |  | X |  |  |  |  |  |  |  |  |  |  |  |  |  |  |  |  |  |  |
| GT512chimAB 67A |  | X |  |  |  |  |  |  | ■ | ■ | ■ | ■ |  |  |  |  |  |  |  |  |  |  | X | X | X | X | X | X |  |  |  |  |  |  |  |  |  | X |  |  |  |  |  |  |  |  |  |  |  |  |  |  |  |  |  |  |
| GT512chimAB 89A |  | X |  |  |  |  |  |  |  | ■ | ■ | ■ | ■ |  |  |  |  |  |  |  |  |  | X | X | X | X | X | X |  |  |  |  |  |  |  |  |  | X |  |  |  |  |  |  |  |  |  |  |  |  |  |  |  |  |  |  |
| R&D |  | X |  |  |  |  |  |  | ░ | ░ | ░ | ░ | ░ | ░ |  |  |  |  |  |  |  | ░ | X | X | X | X | X | X |  |  |  |  |  |  |  |  |  | X |  |  |  |  |  |  |  |  |  |  |  |  |  |  |  |  |  |  |

EC2 (aa 137-161)

| Name | C 137 | W 138 | T 139 | A 140 | H 141 | A 142 | I 143 | I 144 | R 145 | D 146 | F 147 | Y 148 | N 149 | P 150 | L 151 | V 152 | A 153 | E 154 | A 155 | Q 156 | K 157 | R 158 | E 159 | L 160 | G 161 |
|---|---|---|---|---|---|---|---|---|---|---|---|---|---|---|---|---|---|---|---|---|---|---|---|---|---|
| GT512chimAB 61D |  |  |  |  |  |  |  |  |  |  |  |  |  |  |  |  |  |  |  |  |  |  |  |  |  |
| GT512chimAB 64A |  |  |  |  |  |  |  |  |  |  |  |  |  |  |  |  |  |  |  |  |  |  |  |  |  |
| GT512chimAB 67A |  |  |  |  |  |  |  |  |  |  |  |  |  |  | ░ |  |  |  |  |  |  |  |  |  |  |
| GT512chimAB 89A |  |  |  |  |  |  |  |  |  |  |  |  |  |  |  |  |  |  |  |  |  |  |  |  |  |
| R&D |  |  |  |  |  |  |  |  |  |  |  |  |  |  | ■ |  |  |  |  |  |  |  |  |  |  |

Legend:
- X : altered transport to the membrane
- ☐ : no influence on antibody binding
- ░ : contributes to antibody binding
- ■ : essential for antibody binding

SEQUENCE LISTING

```
<160> NUMBER OF SEQ ID NOS: 66

<210> SEQ ID NO 1
<211> LENGTH: 1369
<212> TYPE: DNA
<213> ORGANISM: Homo sapiens
```

<400> SEQUENCE: 1

```
cgacactcgg cctaggaatt tcccttatct ccttcgcagt gcagctcctt caacctcgcc      60
atggcctctg ccggaatgca gatcctggga gtcgtcctga cactgctggg ctgggtgaat     120
ggcctggtct cctgtgccct gcccatgtgg aaggtgaccg ctttcatcgg caacagcatc     180
gtggtggccc aggtggtgtg ggagggcctg tggatgtcct gcgtggtgca gagcaccggc     240
cagatgcagt gcaaggtgta cgactcactg ctggcgctgc cacaggacct gcaggctgca     300
cgtgccctct gtgtcatcgc cctccttgtg gccctgttcg gcttgctggt ctaccttgct     360
ggggccaagt gtaccacctg tgtggaggag aaggattcca aggcccgcct ggtgctcacc     420
tctgggattg tctttgtcat ctcaggggtc ctgacgctaa tccccgtgtg ctggacggcg     480
catgccatca tccgggactt ctataacccc ctggtggctg aggcccaaaa gcgggagctg     540
ggggcctccc tctacttggg ctgggcggcc tcaggccttt tgttgctggg tgggggggttg     600
ctgtgctgca cttgccccct cgggggggtcc cagggcccca gccattacat ggcccgctac     660
tcaacatctg ccccctgccat ctctcggggg ccctctgagt accctaccaa gaattacgtc     720
tgacgtggag gggaatgggg gctccgctgg cgctagagcc atccagaagt ggcagtgccc     780
aacagctttg ggatgggttc gtaccttttg tttctgcctc ctgctatttt tcttttgact     840
gaggatattt aaaattcatt tgaaaactga gccaaggtgt tgactcagac tctcacttag     900
gctctgctgt ttctcaccct tggatgatgg agccaaagag gggatgcttt gagattctgg     960
atcttgacat gcccatctta gaagccagtc aagctatgga actaatgcgg aggctgcttg    1020
ctgtgctggc tttgcaacaa gacagactgt ccccaagagt tcctgctgct gctgggggct    1080
gggcttccct agatgtcact ggacagctgc ccccatcct actcaggtct ctggagctcc     1140
tctcttcacc cctggaaaaa caaatgatct gttaacaaag gactgcccac ctccggaact    1200
tctgacctct gtttcctccg tcctgataag acgtccaccc cccagggcca ggtcccagct    1260
atgtagaccc ccgcccccac ctccaacact gcacccttct gccctgcccc cctcgtctca    1320
ccccctttac actcacattt ttatcaaata aagcatgttt tgttagtgc                1369
```

<210> SEQ ID NO 2
<211> LENGTH: 220
<212> TYPE: PRT
<213> ORGANISM: Homo sapiens

<400> SEQUENCE: 2

```
Met Ala Ser Ala Gly Met Gln Ile Leu Gly Val Val Leu Thr Leu Leu
1               5                   10                  15
Gly Trp Val Asn Gly Leu Val Ser Cys Ala Leu Pro Met Trp Lys Val
            20                  25                  30
Thr Ala Phe Ile Gly Asn Ser Ile Val Val Ala Gln Val Val Trp Glu
        35                  40                  45
Gly Leu Trp Met Ser Cys Val Val Gln Ser Thr Gly Gln Met Gln Cys
    50                  55                  60
Lys Val Tyr Asp Ser Leu Leu Ala Leu Pro Gln Asp Leu Gln Ala Ala
65                  70                  75                  80
Arg Ala Leu Cys Val Ile Ala Leu Leu Val Ala Leu Phe Gly Leu Leu
                85                  90                  95
Val Tyr Leu Ala Gly Ala Lys Cys Thr Thr Cys Val Glu Glu Lys Asp
            100                 105                 110
Ser Lys Ala Arg Leu Val Leu Thr Ser Gly Ile Val Phe Val Ile Ser
        115                 120                 125
```

Gly Val Leu Thr Leu Ile Pro Val Cys Trp Thr Ala His Ala Ile Ile
         130                 135                 140

Arg Asp Phe Tyr Asn Pro Leu Val Ala Glu Ala Gln Lys Arg Glu Leu
145                 150                 155                 160

Gly Ala Ser Leu Tyr Leu Gly Trp Ala Ala Ser Gly Leu Leu Leu
                165                 170                 175

Gly Gly Gly Leu Leu Cys Cys Thr Cys Pro Ser Gly Ser Gln Gly
            180                 185                 190

Pro Ser His Tyr Met Ala Arg Tyr Ser Thr Ser Ala Pro Ala Ile Ser
        195                 200                 205

Arg Gly Pro Ser Glu Tyr Pro Thr Lys Asn Tyr Val
    210                 215                 220

<210> SEQ ID NO 3
<211> LENGTH: 805
<212> TYPE: DNA
<213> ORGANISM: Artificial
<220> FEATURE:
<223> OTHER INFORMATION: codon-optimized nucleic acid sequence encoding
      human claudin 6

<400> SEQUENCE: 3
caagcgcgtc aattaaccct cactaaaggg aacaaaagct gttaattaac taaggtacca    60
agcttgccac catggccagc gccggcatgc agatcctggg agtggtgctg accctgctgg   120
gctgggtgaa cggcctggtg tcctgcgccc tgcccatgtg gaaagtgacc gccttcatcg   180
gcaacagcat cgtggtggcc caggtcgtgt gggagggcct gtggatgagc tgtgtggtgc   240
agagcaccgg ccagatgcag tgcaaggtgt acgacagcct gctggccctg cctcaggatc   300
tgcaggccgc cagagccctg tgtgtgatcg ccctgctggt cgccctgttc ggcctgctgg   360
tgtacctcgc tggcgccaag tgcaccacct gtgtggagga aaaggacagc aaggcccggc   420
tggtcctgac aagcggcatc gtgttcgtga tcagcgccgt gctgacactg atccccgtgt   480
gctggaccgc ccacgccatc atccgggact ctacaacccc tctggtggcc gaggcccaga   540
agagagagct gggcgccagc ctgtatctgg atgggccgc ctcaggactg ctgctgctgg   600
gcggaggcct gctgtgctgt acatgtccta gcggcggctc ccagggccct agccactaca   660
tggcccggta cagcaccagc gcccctgcca tcagcagagg ccccagcgag taccccacca   720
agaactacgt gtgataggaa ttcgagctct tatggcgcgc caattcgcc ctatagtgag   780 tcgtattacg tcgcgctcac tggcc                                        805

<210> SEQ ID NO 4
<211> LENGTH: 165
<212> TYPE: DNA
<213> ORGANISM: Artificial
<220> FEATURE:
<223> OTHER INFORMATION: codon-optimized nucleic acid sequence encoding
      the predicted extracellular loop 2 (EC2) of human claudin 6

<400> SEQUENCE: 4
ggcgcgccaa ggtaccaagc ttgccaccat ggaaaccgac accctgctgc tgtgggtgct    60
gctcctgtgg gtcccaggct ctacaggcga cgccgcccag cccagagact ctacaacccc   120
cctggtggcc gaggcccaga agctcgagtc tagagggtta attaa                  165

<210> SEQ ID NO 5
<211> LENGTH: 38
<212> TYPE: PRT

```
<213> ORGANISM: Artificial
<220> FEATURE:
<223> OTHER INFORMATION: predicted 2nd extracellular loop of human
      claudin 6 containing an Ig kappa leader sequence
<220> FEATURE:
<221> NAME/KEY: SIGNAL
<222> LOCATION: (1)..(21)
<223> OTHER INFORMATION: Ig kappa leader sequence
<220> FEATURE:
<221> NAME/KEY: DOMAIN
<222> LOCATION: (26)..(38)
<223> OTHER INFORMATION: predicted 2nd extracellular loop (EC2) of human
      claudin 6

<400> SEQUENCE: 5

Met Glu Thr Asp Thr Leu Leu Leu Trp Val Leu Leu Leu Trp Val Pro
1               5                   10                  15

Gly Ser Thr Gly Asp Ala Ala Gln Pro Arg Asp Phe Tyr Asn Pro Leu
            20                  25                  30

Val Ala Glu Ala Gln Lys
        35

<210> SEQ ID NO 6
<211> LENGTH: 13
<212> TYPE: PRT
<213> ORGANISM: Homo sapiens

<400> SEQUENCE: 6

Arg Asp Phe Tyr Asn Pro Leu Val Ala Glu Ala Gln Lys
1               5                   10

<210> SEQ ID NO 7
<211> LENGTH: 53
<212> TYPE: PRT
<213> ORGANISM: Homo sapiens

<400> SEQUENCE: 7

Pro Met Trp Lys Val Thr Ala Phe Ile Gly Asn Ser Ile Val Val Ala
1               5                   10                  15

Gln Val Val Trp Glu Gly Leu Trp Met Ser Cys Val Val Gln Ser Thr
            20                  25                  30

Gly Gln Met Gln Cys Lys Val Tyr Asp Ser Leu Leu Ala Leu Pro Gln
        35                  40                  45

Asp Leu Gln Ala Ala
    50

<210> SEQ ID NO 8
<211> LENGTH: 220
<212> TYPE: PRT
<213> ORGANISM: Homo sapiens
<220> FEATURE:
<221> NAME/KEY: VARIANT
<222> LOCATION: (143)..(143)
<223> OTHER INFORMATION: human claudin 6 I143V polymorphism

<400> SEQUENCE: 8

Met Ala Ser Ala Gly Met Gln Ile Leu Gly Val Val Leu Thr Leu Leu
1               5                   10                  15

Gly Trp Val Asn Gly Leu Val Ser Cys Ala Leu Pro Met Trp Lys Val
            20                  25                  30

Thr Ala Phe Ile Gly Asn Ser Ile Val Val Ala Gln Val Val Trp Glu
        35                  40                  45

Gly Leu Trp Met Ser Cys Val Val Gln Ser Thr Gly Gln Met Gln Cys
    50                  55                  60
```

```
Lys Val Tyr Asp Ser Leu Leu Ala Leu Pro Gln Asp Leu Gln Ala Ala
 65                  70                  75                  80

Arg Ala Leu Cys Val Ile Ala Leu Leu Val Ala Leu Phe Gly Leu Leu
                 85                  90                  95

Val Tyr Leu Ala Gly Ala Lys Cys Thr Thr Cys Val Glu Glu Lys Asp
            100                 105                 110

Ser Lys Ala Arg Leu Val Leu Thr Ser Gly Ile Val Phe Val Ile Ser
        115                 120                 125

Gly Val Leu Thr Leu Ile Pro Val Cys Trp Thr Ala His Ala Val Ile
    130                 135                 140

Arg Asp Phe Tyr Asn Pro Leu Val Ala Glu Ala Gln Lys Arg Glu Leu
145                 150                 155                 160

Gly Ala Ser Leu Tyr Leu Gly Trp Ala Ala Ser Gly Leu Leu Leu Leu
                165                 170                 175

Gly Gly Gly Leu Leu Cys Cys Thr Cys Pro Ser Gly Gly Ser Gln Gly
            180                 185                 190

Pro Ser His Tyr Met Ala Arg Tyr Ser Thr Ser Ala Pro Ala Ile Ser
        195                 200                 205

Arg Gly Pro Ser Glu Tyr Pro Thr Lys Asn Tyr Val
    210                 215                 220

<210> SEQ ID NO 9
<211> LENGTH: 217
<212> TYPE: PRT
<213> ORGANISM: Homo sapiens

<400> SEQUENCE: 9

Met Ala Ser Thr Gly Leu Glu Leu Leu Gly Met Thr Leu Ala Val Leu
 1               5                  10                  15

Gly Trp Leu Gly Thr Leu Val Ser Cys Ala Leu Pro Leu Trp Lys Val
                20                  25                  30

Thr Ala Phe Ile Gly Asn Ser Ile Val Ala Gln Val Val Trp Glu
            35                  40                  45

Gly Leu Trp Met Ser Cys Val Val Gln Ser Thr Gly Gln Met Gln Cys
 50                 55                  60

Lys Val Tyr Asp Ser Leu Leu Ala Leu Pro Gln Asp Leu Gln Ala Ala
 65                 70                  75                  80

Arg Ala Leu Cys Val Ile Ala Leu Leu Ala Leu Leu Gly Leu Leu
                85                  90                  95

Val Ala Ile Thr Gly Ala Gln Cys Thr Thr Cys Val Glu Asp Glu Gly
            100                 105                 110

Ala Lys Ala Arg Ile Val Leu Thr Ala Gly Val Ile Leu Leu Leu Ala
        115                 120                 125

Gly Ile Leu Val Leu Ile Pro Val Cys Trp Thr Ala His Ala Ile Ile
    130                 135                 140

Gln Asp Phe Tyr Asn Pro Leu Val Ala Glu Ala Leu Lys Arg Glu Leu
145                 150                 155                 160

Gly Ala Ser Leu Tyr Leu Gly Trp Ala Ala Ala Leu Leu Met Leu
                165                 170                 175

Gly Gly Gly Leu Leu Cys Cys Thr Cys Pro Pro Gln Val Glu Arg
            180                 185                 190

Pro Arg Gly Pro Arg Leu Gly Tyr Ser Ile Pro Ser Arg Ser Gly Ala
        195                 200                 205

Ser Gly Leu Asp Lys Arg Asp Tyr Val
```

```
                210               215

<210> SEQ ID NO 10
<211> LENGTH: 209
<212> TYPE: PRT
<213> ORGANISM: Homo sapiens

<400> SEQUENCE: 10

Met Ala Ser Met Gly Leu Gln Val Met Gly Ile Ala Leu Ala Val Leu
1               5                   10                  15

Gly Trp Leu Ala Val Met Leu Cys Cys Ala Leu Pro Met Trp Arg Val
                20                  25                  30

Thr Ala Phe Ile Gly Ser Asn Ile Val Thr Ser Gln Thr Ile Trp Glu
            35                  40                  45

Gly Leu Trp Met Asn Cys Val Val Gln Ser Thr Gly Gln Met Gln Cys
        50                  55                  60

Lys Val Tyr Asp Ser Leu Leu Ala Leu Pro Gln Asp Leu Gln Ala Ala
65                  70                  75                  80

Arg Ala Leu Val Ile Ile Ser Ile Ile Val Ala Ala Leu Gly Val Leu
                85                  90                  95

Leu Ser Val Val Gly Gly Lys Cys Thr Asn Cys Leu Glu Asp Glu Ser
            100                 105                 110

Ala Lys Ala Lys Thr Met Ile Val Ala Gly Val Val Phe Leu Leu Ala
        115                 120                 125

Gly Leu Met Val Ile Val Pro Val Ser Trp Thr Ala His Asn Ile Ile
    130                 135                 140

Gln Asp Phe Tyr Asn Pro Leu Val Ala Ser Gly Gln Lys Arg Glu Met
145                 150                 155                 160

Gly Ala Ser Leu Tyr Val Gly Trp Ala Ala Ser Gly Leu Leu Leu Leu
                165                 170                 175

Gly Gly Gly Leu Leu Cys Cys Asn Cys Pro Pro Arg Thr Asp Lys Pro
            180                 185                 190

Tyr Ser Ala Lys Tyr Ser Ala Ala Arg Ser Ala Ala Ala Ser Asn Tyr
        195                 200                 205

Val

<210> SEQ ID NO 11
<211> LENGTH: 220
<212> TYPE: PRT
<213> ORGANISM: Homo sapiens

<400> SEQUENCE: 11

Met Ser Met Gly Leu Glu Ile Thr Gly Thr Ala Leu Ala Val Leu Gly
1               5                   10                  15

Trp Leu Gly Thr Ile Val Cys Cys Ala Leu Pro Met Trp Arg Val Ser
                20                  25                  30

Ala Phe Ile Gly Ser Asn Ile Ile Thr Ser Gln Asn Ile Trp Glu Gly
            35                  40                  45

Leu Trp Met Asn Cys Val Val Gln Ser Thr Gly Gln Met Gln Cys Lys
        50                  55                  60

Val Tyr Asp Ser Leu Leu Ala Leu Pro Gln Asp Leu Gln Ala Ala Arg
65                  70                  75                  80

Ala Leu Ile Val Val Ala Ile Leu Leu Ala Ala Phe Gly Leu Leu Val
                85                  90                  95

Ala Leu Val Gly Ala Gln Cys Thr Asn Cys Val Gln Asp Asp Thr Ala
            100                 105                 110
```

```
Lys Ala Lys Ile Thr Ile Val Ala Gly Val Leu Phe Leu Leu Ala Ala
        115                 120                 125

Leu Leu Thr Leu Val Pro Val Ser Trp Ser Ala Asn Thr Ile Ile Arg
        130                 135                 140

Asp Phe Tyr Asn Pro Val Val Pro Glu Ala Gln Lys Arg Glu Met Gly
145                 150                 155                 160

Ala Gly Leu Tyr Val Gly Trp Ala Ala Ala Leu Gln Leu Leu Gly
                165                 170                 175

Gly Ala Leu Leu Cys Cys Ser Cys Pro Arg Glu Lys Lys Tyr Thr
                180                 185                 190

Ala Thr Lys Val Val Tyr Ser Ala Pro Arg Ser Thr Gly Pro Gly Ala
        195                 200                 205

Ser Leu Gly Thr Gly Tyr Asp Arg Lys Asp Tyr Val
        210                 215                 220

<210> SEQ ID NO 12
<211> LENGTH: 159
<212> TYPE: DNA
<213> ORGANISM: Artificial
<220> FEATURE:
<223> OTHER INFORMATION: codon-optimized nucleic acid sequence encoding
      the predicted extracellular loop 1 (EC1) of human claudin 6

<400> SEQUENCE: 12
cccatgtgga aagtgaccgc cttcatcggc aacagcatcg tggtggccca ggtggtctgg      60
gagggcctgt ggatgagctg cgtggtgcag agcaccggcc agatgcagtg caaggtgtac     120
gacagcctgc tggccctgcc tcaggatctg caggctgct                            159

<210> SEQ ID NO 13
<211> LENGTH: 106
<212> TYPE: PRT
<213> ORGANISM: Artificial
<220> FEATURE:
<223> OTHER INFORMATION: predicted 1st extracellular loop of human
      claudin 6 containing an Ig kappa leader sequence
<220> FEATURE:
<221> NAME/KEY: Signal
<222> LOCATION: (1)..(21)
<223> OTHER INFORMATION: Ig kappa leader sequence
<220> FEATURE:
<221> NAME/KEY: Domain
<222> LOCATION: (26)..(78)
<223> OTHER INFORMATION: predicted 1st extracellular loop (EC1) of human
      claudin 6

<400> SEQUENCE: 13

Met Glu Thr Asp Thr Leu Leu Leu Trp Val Leu Leu Leu Trp Val Pro
1               5                   10                  15

Gly Ser Thr Gly Asp Ala Ala Gln Pro Pro Met Trp Lys Val Thr Ala
                20                  25                  30

Phe Ile Gly Asn Ser Ile Val Val Ala Gln Val Val Trp Glu Gly Leu
            35                  40                  45

Trp Met Ser Cys Val Val Gln Ser Thr Gly Gln Met Gln Cys Lys Val
        50                  55                  60

Tyr Asp Ser Leu Leu Ala Leu Pro Gln Asp Leu Gln Ala Ala Leu Glu
65                  70                  75                  80

Ser Arg Gly Pro Phe Glu Gln Lys Leu Ile Ser Glu Glu Asp Leu Asn
                85                  90                  95

Met His Thr Gly His His His His His His
                100                 105
```

<210> SEQ ID NO 14
<211> LENGTH: 13
<212> TYPE: PRT
<213> ORGANISM: Homo sapiens

<400> SEQUENCE: 14

Pro Met Trp Lys Val Thr Ala Phe Ile Gly Asn Ser Ile
1               5                   10

<210> SEQ ID NO 15
<211> LENGTH: 15
<212> TYPE: PRT
<213> ORGANISM: Homo sapiens

<400> SEQUENCE: 15

Met Trp Lys Val Thr Ala Phe Ile Gly Asn Ser Ile Val Val Ala
1               5                   10                  15

<210> SEQ ID NO 16
<211> LENGTH: 20
<212> TYPE: DNA
<213> ORGANISM: Artificial
<220> FEATURE:
<223> OTHER INFORMATION: Oligonucleotide

<400> SEQUENCE: 16
tccatgacgt tcctgacgtt                                          20

<210> SEQ ID NO 17
<211> LENGTH: 43
<212> TYPE: DNA
<213> ORGANISM: Artificial Sequence
<220> FEATURE:
<223> OTHER INFORMATION: Oligonucleotide

<400> SEQUENCE: 17
gagaaagctt gccgccacca tgggatggag ctggatcttt ctc                43

<210> SEQ ID NO 18
<211> LENGTH: 43
<212> TYPE: DNA
<213> ORGANISM: Artificial Sequence
<220> FEATURE:
<223> OTHER INFORMATION: Oligonucleotide

<400> SEQUENCE: 18
gagagggccc ttggtggagg ctgaagagac tgtgagagtg gtg                43

<210> SEQ ID NO 19
<211> LENGTH: 43
<212> TYPE: DNA
<213> ORGANISM: Artificial Sequence
<220> FEATURE:
<223> OTHER INFORMATION: Oligonucleotide

<400> SEQUENCE: 19
gagagggccc ttggtggagg ctgaggagac tgtgagagtg gtg                43

<210> SEQ ID NO 20
<211> LENGTH: 43
<212> TYPE: DNA
<213> ORGANISM: Artificial Sequence
<220> FEATURE:
<223> OTHER INFORMATION: Oligonucleotide

<400> SEQUENCE: 20
gagagggccc ttggtggagg ctgaggagac tgtgagagtg gtg          43

<210> SEQ ID NO 21
<211> LENGTH: 46
<212> TYPE: DNA
<213> ORGANISM: Artificial Sequence
<220> FEATURE:
<223> OTHER INFORMATION: Oligonucleotide

<400> SEQUENCE: 21
gagaaagctt gccgccacca tgcattttca agtgcagatt ttcagc          46

<210> SEQ ID NO 22
<211> LENGTH: 33
<212> TYPE: DNA
<213> ORGANISM: Artificial Sequence
<220> FEATURE:
<223> OTHER INFORMATION: Oligonucleotide

<400> SEQUENCE: 22
cacacgtacg tttgatttcc agcttggtgc ctc          33

<210> SEQ ID NO 23
<211> LENGTH: 33
<212> TYPE: DNA
<213> ORGANISM: Artificial Sequence
<220> FEATURE:
<223> OTHER INFORMATION: Oligonucleotide

<400> SEQUENCE: 23
cacacgtacg tttgatttcc agcttggtgc ctc          33

<210> SEQ ID NO 24
<211> LENGTH: 993
<212> TYPE: DNA
<213> ORGANISM: Homo sapiens

<400> SEQUENCE: 24
gcctccacca agggcccaag cgtgttcccc ctggccccca gcagcaagag caccagcggc          60
ggcacagccg ccctgggctg cctggtgaag gactacttcc ccgagcccgt gaccgtgagc         120
tggaacagcg gagccctgac ctccggcgtg cacaccttcc ccgccgtgct gcagagcagc         180
ggcctgtaca gcctgagcag cgtggtgacc gtgcccagca gcagcctggg cacccagacc         240
tacatctgca acgtgaacca caagcccagc aacaccaagg tggacaagag agtggagccc         300
aagagctgcg acaagaccca cacctgcccc cctgcccag cccagagct gctgggcgga         360
cccagcgtgt tcctgttccc ccccaagccc aaggacaccc tgatgatcag caggacccc          420
gaggtgacct gcgtggtggt ggacgtgagc cacgaggacc cagaggtgaa gttcaactgg         480
tacgtggacg gcgtggaggt gcacaacgcc aagaccaagc cagagagga gcagtacaac         540
agcacctaca gggtggtgtc cgtgctgacc gtgctgcacc aggactggct gaacggcaag         600
gaatacaagt gcaaggtctc caacaaggcc ctgccagccc catcgaaaaa gaccatcagc         660
aaggccaagg gccagccacg ggagcccag gtgtacaccc tgcccccag ccggaggag           720
atgaccaaga accaggtgtc cctgacctgt ctggtgaagg gcttctaccc cagcgacatc         780
gccgtggagt gggagagcaa cggccagccc gagaacaact acaagaccac ccccccagtg         840
ctggacagcg acggcagctt cttcctgtac agcaagctga ccgtggacaa gtccaggtgg         900
cagcagggca acgtgttcag ctgcagcgtg atgcacgagg ccctgcacaa ccactacacc         960
cagaagtccc tgagcctgag ccccggcaag tag                                      993

<210> SEQ ID NO 25
<211> LENGTH: 330
<212> TYPE: PRT
<213> ORGANISM: Homo sapiens

<400> SEQUENCE: 25

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 26
<211> LENGTH: 324
<212> TYPE: DNA
<213> ORGANISM: Homo sapiens

```
<400> SEQUENCE: 26
cgtacggtgg ccgctcccag cgtgttcatc ttccccccca gcgacgagca gctgaagtcc    60
ggcaccgcca gcgtggtgtg cctgctgaac aacttctacc cccgggaggc caaggtgcag   120
tggaaggtgg acaacgccct gcagagcggc aacagccagg agagcgtcac cgagcaggac   180
agcaaggact ccacctacag cctgagcagc accctgaccc tgagcaaggc cgactacgag   240
aagcacaagg tgtacgcctg cgaggtgacc caccagggcc tgtccagccc cgtgaccaag   300
agcttcaaca ggggcgagtg ctag                                          324

<210> SEQ ID NO 27
<211> LENGTH: 107
<212> TYPE: PRT
<213> ORGANISM: Homo sapiens

<400> SEQUENCE: 27

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 28
<211> LENGTH: 32
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (31)..(32)
<223> OTHER INFORMATION: any nucleotide

<400> SEQUENCE: 28
tttttttttt tttttttttt tttttttttt nn                                  32

<210> SEQ ID NO 29
<211> LENGTH: 30
<212> TYPE: DNA
<213> ORGANISM: Artificial Sequence
<220> FEATURE:
<223> OTHER INFORMATION: Oligonucleotide

<400> SEQUENCE: 29
aagcagtggt atcaacgcag agtacgcggg                                     30

<210> SEQ ID NO 30
<211> LENGTH: 26
<212> TYPE: DNA
<213> ORGANISM: Artificial Sequence
<220> FEATURE:
<223> OTHER INFORMATION: Oligonucleotide
```

<210> SEQ ID NO 31
<211> LENGTH: 25
<212> TYPE: DNA
<213> ORGANISM: Artificial Sequence
<220> FEATURE:
<223> OTHER INFORMATION: Oligonucleotide

<400> SEQUENCE: 31
acaggggcca gtggatagac cgatg                                       25

<210> SEQ ID NO 32
<211> LENGTH: 45
<212> TYPE: DNA
<213> ORGANISM: Artificial Sequence
<220> FEATURE:
<223> OTHER INFORMATION: Oligonucleotide

<400> SEQUENCE: 32
gtaatacgac tcactatagg gcaagcagtg gtatcaacgc agagt                 45

<210> SEQ ID NO 33
<211> LENGTH: 22
<212> TYPE: DNA
<213> ORGANISM: Artificial Sequence
<220> FEATURE:
<223> OTHER INFORMATION: Oligonucleotide

<400> SEQUENCE: 33
gtaatacgac tcactatagg gc                                          22

<210> SEQ ID NO 34
<211> LENGTH: 117
<212> TYPE: PRT
<213> ORGANISM: Artificial Sequence
<220> FEATURE:
<223> OTHER INFORMATION: Antibody VH sequence

<400> SEQUENCE: 34

Glu Val Gln Leu Gln Gln Ser Gly Pro Glu Leu Val Lys Pro Gly Ala
1               5                   10                  15

Ser Met Lys Ile Ser Cys Lys Ala Ser Gly Tyr Ser Phe Thr Gly Tyr
            20                  25                  30

Thr Met Asn Trp Val Lys Gln Ser His Gly Lys Asn Leu Glu Trp Ile
        35                  40                  45

Gly Leu Ile Asn Pro Tyr Asn Gly Gly Thr Ser Tyr Asn Gln Lys Phe
    50                  55                  60

Lys Gly Lys Ala Thr Leu Thr Ile Asp Lys Ser Ser Ser Thr Ala Tyr
65                  70                  75                  80

Met Glu Leu Leu Ser Leu Thr Ser Glu Asp Ser Ala Val Tyr Tyr Cys
                85                  90                  95

Ala Arg Asp Tyr Gly Tyr Val Leu Asp Tyr Trp Gly Gln Gly Thr Thr
            100                 105                 110

Leu Thr Val Ser Ser
        115

<210> SEQ ID NO 35
<211> LENGTH: 107
<212> TYPE: PRT

```
<213> ORGANISM: Artificial Sequence
<220> FEATURE:
<223> OTHER INFORMATION: Antibody VL sequence

<400> SEQUENCE: 35

Gln Ile Val Leu Thr Gln Ser Pro Ala Ile Met Ser Ala Ser Pro Gly
1               5                   10                  15

Glu Lys Val Thr Ile Thr Cys Ser Ala Ser Ser Val Ser Tyr Leu
            20                  25                  30

His Trp Phe Gln Gln Lys Pro Gly Thr Ser Pro Lys Leu Trp Val Tyr
        35                  40                  45

Ser Thr Ser Asn Leu Pro Ser Gly Val Pro Ala Arg Phe Gly Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Ile Tyr Pro Pro Trp
                85                  90                  95

Thr Phe Gly Gly Gly Thr Lys Leu Glu Ile Lys
            100                 105

<210> SEQ ID NO 36
<211> LENGTH: 117
<212> TYPE: PRT
<213> ORGANISM: Artificial Sequence
<220> FEATURE:
<223> OTHER INFORMATION: Antibody VH sequence

<400> SEQUENCE: 36

Glu Val Gln Leu Gln Gln Ser Gly Pro Glu Leu Val Lys Pro Gly Ala
1               5                   10                  15

Ser Met Lys Ile Ser Cys Lys Ala Ser Gly Tyr Ser Phe Thr Gly Tyr
            20                  25                  30

Thr Met Asn Trp Val Lys Gln Ser His Gly Lys Asn Leu Glu Trp Ile
        35                  40                  45

Gly Leu Ile Asn Pro Tyr Asn Gly Gly Thr Ile Tyr Asn Gln Lys Phe
    50                  55                  60

Lys Gly Lys Ala Thr Leu Thr Val Asp Lys Ser Ser Thr Ala Tyr
65                  70                  75                  80

Met Glu Leu Leu Ser Leu Thr Ser Glu Asp Ser Ala Val Tyr Tyr Cys
                85                  90                  95

Ala Arg Asp Tyr Gly Phe Val Leu Asp Tyr Trp Gly Gln Gly Thr Thr
            100                 105                 110

Leu Thr Val Ser Ser
        115

<210> SEQ ID NO 37
<211> LENGTH: 107
<212> TYPE: PRT
<213> ORGANISM: Artificial Sequence
<220> FEATURE:
<223> OTHER INFORMATION: Antibody VL sequence

<400> SEQUENCE: 37

Gln Ile Val Leu Thr Gln Ser Pro Ser Ile Met Ser Val Ser Pro Gly
1               5                   10                  15

Glu Lys Val Thr Ile Thr Cys Ser Ala Ser Ser Ser Val Ser Tyr Met
            20                  25                  30

His Trp Phe Gln Gln Lys Pro Gly Thr Ser Pro Lys Leu Cys Ile Tyr
        35                  40                  45
```

```
Ser Thr Ser Asn Leu Ala Ser Gly Val Pro Ala Arg Phe Ser Gly Arg
        50                  55                  60

Gly Ser Gly Thr Ser Tyr Ser Leu Thr Ile Ser Arg Val Ala Ala Glu
65                  70                  75                  80

Asp Ala Ala Thr Tyr Tyr Cys Gln Gln Arg Ser Asn Tyr Pro Pro Trp
                85                  90                  95

Thr Phe Gly Gly Gly Thr Lys Leu Glu Ile Lys
            100                 105
```

<210> SEQ ID NO 38
<211> LENGTH: 117
<212> TYPE: PRT
<213> ORGANISM: Artificial Sequence
<220> FEATURE:
<223> OTHER INFORMATION: Antibody VH sequence

<400> SEQUENCE: 38

```
Glu Val Gln Leu Gln Gln Ser Gly Pro Glu Leu Val Lys Pro Gly Ala
1               5                   10                  15

Ser Met Lys Ile Ser Cys Lys Ala Ser Gly Tyr Ser Phe Thr Gly Tyr
                20                  25                  30

Thr Met Asn Trp Val Lys Gln Ser His Gly Lys Asn Leu Glu Trp Ile
            35                  40                  45

Gly Leu Ile Asn Pro Tyr Asn Gly Gly Ile Ile Tyr Asn Gln Lys Phe
        50                  55                  60

Lys Gly Lys Ala Thr Leu Thr Val Asp Lys Ser Ser Ser Thr Ala Tyr
65                  70                  75                  80

Met Glu Leu Leu Ser Leu Thr Ser Glu Asp Ser Ala Val Phe Tyr Cys
                85                  90                  95

Ala Arg Asp Phe Gly Tyr Val Leu Asp Tyr Trp Gly Gln Gly Thr Thr
                100                 105                 110

Leu Thr Val Ser Ser
            115
```

<210> SEQ ID NO 39
<211> LENGTH: 107
<212> TYPE: PRT
<213> ORGANISM: Artificial Sequence
<220> FEATURE:
<223> OTHER INFORMATION: Antibody VL sequence

<400> SEQUENCE: 39

```
Gln Ile Val Leu Thr Gln Ser Pro Ala Ile Met Ser Ala Ser Pro Gly
1               5                   10                  15

Glu Lys Val Thr Ile Thr Cys Ser Ala Ser Ser Ser Val Ser Tyr Met
                20                  25                  30

His Trp Phe Gln Gln Lys Pro Gly Thr Ser Pro Lys Leu Trp Ile Tyr
            35                  40                  45

Ser Thr Ser Asn Leu Ala Ser Gly Val Pro Ala Arg Phe Ser Gly Ser
        50                  55                  60

Gly Ser Gly Thr Ser Tyr Ser Leu Thr Ile Ser Arg Val Ala Ala Glu
65                  70                  75                  80

Asp Ala Ala Thr Tyr Tyr Cys Gln Gln Arg Ser Thr Tyr Pro Pro Trp
                85                  90                  95

Thr Phe Gly Gly Gly Thr Lys Leu Glu Ile Lys
            100                 105
```

```
<210> SEQ ID NO 40
<211> LENGTH: 117
<212> TYPE: PRT
<213> ORGANISM: Artificial Sequence
<220> FEATURE:
<223> OTHER INFORMATION: Antibody VH sequence

<400> SEQUENCE: 40

Glu Val Gln Leu Gln Gln Ser Arg Pro Glu Leu Val Lys Pro Gly Ala
1               5                   10                  15

Ser Met Lys Ile Ser Cys Lys Ala Ser Gly Tyr Ser Phe Thr Gly Tyr
                20                  25                  30

Thr Leu Asn Trp Val Lys Gln Ser His Gly Lys Asn Leu Glu Trp Ile
            35                  40                  45

Gly Leu Ile Asn Pro Tyr Asn Gly Gly Ser Ser Tyr Asn Gln Lys Phe
50                  55                  60

Lys Asp Lys Ala Thr Leu Thr Val Asp Lys Ser Ser Ser Thr Ala Tyr
65                  70                  75                  80

Met Glu Leu Leu Ser Leu Thr Ser Glu Asp Ser Ala Val Tyr Tyr Cys
                85                  90                  95

Ala Arg Asp Tyr Gly Tyr Val Phe Asp Tyr Trp Gly Gln Gly Thr Thr
                100                 105                 110

Leu Thr Val Ser Ser
        115

<210> SEQ ID NO 41
<211> LENGTH: 107
<212> TYPE: PRT
<213> ORGANISM: Artificial Sequence
<220> FEATURE:
<223> OTHER INFORMATION: Antibody VL sequence

<400> SEQUENCE: 41

Gln Ile Val Leu Thr Gln Ser Pro Ala Ile Met Ser Ala Ser Pro Gly
1               5                   10                  15

Glu Lys Val Thr Ile Thr Cys Ser Ala Ser Ser Ser Val Asn Tyr Met
                20                  25                  30

His Trp Phe Gln Leu Lys Pro Gly Thr Ser Pro Lys Leu Leu Ile Tyr
            35                  40                  45

Ser Thr Ser Asn Leu Ala Ser Gly Val Pro Ala Arg Phe Ser Gly Arg
50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Asn Asn Tyr Pro Pro Trp
                85                  90                  95

Thr Phe Gly Gly Gly Thr Lys Leu Glu Ile Lys
                100                 105

<210> SEQ ID NO 42
<211> LENGTH: 5
<212> TYPE: PRT
<213> ORGANISM: Artificial Sequence
<220> FEATURE:
<223> OTHER INFORMATION: Antibody VH CDR3 sequence
<220> FEATURE:
<221> NAME/KEY: MISC_FEATURE
<222> LOCATION: (1)..(1)
<223> OTHER INFORMATION: Any amino acid, preferably an aromatic amino
      acid, more preferably Phe or Tyr, most preferably Tyr
<220> FEATURE:
<221> NAME/KEY: MISC_FEATURE
<222> LOCATION: (3)..(3)
```

```
<223> OTHER INFORMATION: Any amino acid, preferably an aromatic amino
      acid, more preferably Phe or Tyr, most preferably Tyr
<220> FEATURE:
<221> NAME/KEY: MISC_FEATURE
<222> LOCATION: (5)..(5)
<223> OTHER INFORMATION: Any amino acid, preferably Leu or Phe, more
      preferably Leu

<400> SEQUENCE: 42

Xaa Gly Xaa Val Xaa
1               5

<210> SEQ ID NO 43
<211> LENGTH: 6
<212> TYPE: PRT
<213> ORGANISM: Artificial Sequence
<220> FEATURE:
<223> OTHER INFORMATION: Antibody VH CDR3 sequence
<220> FEATURE:
<221> NAME/KEY: MISC_FEATURE
<222> LOCATION: (2)..(2)
<223> OTHER INFORMATION: Any amino acid, preferably an aromatic amino
      acid, more preferably Phe or Tyr, most preferably Tyr
<220> FEATURE:
<221> NAME/KEY: MISC_FEATURE
<222> LOCATION: (4)..(4)
<223> OTHER INFORMATION: Any amino acid, preferably an aromatic amino
      acid, more preferably Phe or Tyr, most preferably Tyr
<220> FEATURE:
<221> NAME/KEY: MISC_FEATURE
<222> LOCATION: (6)..(6)
<223> OTHER INFORMATION: Any amino acid, preferably Leu or Phe, more
      preferably Leu

<400> SEQUENCE: 43

Asp Xaa Gly Xaa Val Xaa
1               5

<210> SEQ ID NO 44
<211> LENGTH: 6
<212> TYPE: PRT
<213> ORGANISM: Artificial Sequence
<220> FEATURE:
<223> OTHER INFORMATION: Antibody VH CDR3 sequence
<220> FEATURE:
<221> NAME/KEY: MISC_FEATURE
<222> LOCATION: (1)..(1)
<223> OTHER INFORMATION: Any amino acid, preferably an aromatic amino
      acid, more preferably Phe or Tyr, most preferably Tyr
<220> FEATURE:
<221> NAME/KEY: MISC_FEATURE
<222> LOCATION: (3)..(3)
<223> OTHER INFORMATION: Any amino acid, preferably an aromatic amino
      acid, more preferably Phe or Tyr, most preferably Tyr
<220> FEATURE:
<221> NAME/KEY: MISC_FEATURE
<222> LOCATION: (5)..(5)
<223> OTHER INFORMATION: Any amino acid, preferably Leu or Phe, more
      preferably Leu

<400> SEQUENCE: 44

Xaa Gly Xaa Val Xaa Asp
1               5

<210> SEQ ID NO 45
<211> LENGTH: 7
<212> TYPE: PRT
<213> ORGANISM: Artificial Sequence
<220> FEATURE:
<223> OTHER INFORMATION: Antibody VH CDR3 sequence
<220> FEATURE:
<221> NAME/KEY: MISC_FEATURE
<222> LOCATION: (2)..(2)
```

```
<223> OTHER INFORMATION: Any amino acid, preferably an aromatic amino
      acid, more preferably Phe or Tyr, most preferably Tyr
<220> FEATURE:
<221> NAME/KEY: MISC_FEATURE
<222> LOCATION: (4)..(4)
<223> OTHER INFORMATION: Any amino acid, preferably an aromatic amino
      acid, more preferably Phe or Tyr, most preferably Tyr
<220> FEATURE:
<221> NAME/KEY: MISC_FEATURE
<222> LOCATION: (6)..(6)
<223> OTHER INFORMATION: Any amino acid, preferably Leu or Phe, more
      preferably Leu

<400> SEQUENCE: 45

Asp Xaa Gly Xaa Val Xaa Asp
1               5

<210> SEQ ID NO 46
<211> LENGTH: 10
<212> TYPE: PRT
<213> ORGANISM: Artificial Sequence
<220> FEATURE:
<223> OTHER INFORMATION: Antibody VH CDR3 sequence
<220> FEATURE:
<221> NAME/KEY: MISC_FEATURE
<222> LOCATION: (4)..(4)
<223> OTHER INFORMATION: Any amino acid, preferably an aromatic amino
      acid, more preferably Phe or Tyr, most preferably Tyr
<220> FEATURE:
<221> NAME/KEY: MISC_FEATURE
<222> LOCATION: (6)..(6)
<223> OTHER INFORMATION: Any amino acid, preferably an aromatic amino
      acid, more preferably Phe or Tyr, most preferably Tyr
<220> FEATURE:
<221> NAME/KEY: MISC_FEATURE
<222> LOCATION: (8)..(8)
<223> OTHER INFORMATION: Any amino acid, preferably Leu or Phe, more
      preferably Leu

<400> SEQUENCE: 46

Ala Arg Asp Xaa Gly Xaa Val Xaa Asp Tyr
1               5                   10

<210> SEQ ID NO 47
<211> LENGTH: 8
<212> TYPE: PRT
<213> ORGANISM: Artificial Sequence
<220> FEATURE:
<223> OTHER INFORMATION: Antibody VH CDR1 sequence

<400> SEQUENCE: 47

Gly Tyr Ser Phe Thr Gly Tyr Thr
1               5

<210> SEQ ID NO 48
<211> LENGTH: 8
<212> TYPE: PRT
<213> ORGANISM: Artificial Sequence
<220> FEATURE:
<223> OTHER INFORMATION: Antibody VH CDR2 sequence
<220> FEATURE:
<221> NAME/KEY: MISC_FEATURE
<222> LOCATION: (8)..(8)
<223> OTHER INFORMATION: Any amino acid, preferably Thr, Ser or Ile,
      most preferably Thr

<400> SEQUENCE: 48

Ile Asn Pro Tyr Asn Gly Gly Xaa
1               5

<210> SEQ ID NO 49
```

```
<211> LENGTH: 5
<212> TYPE: PRT
<213> ORGANISM: Artificial Sequence
<220> FEATURE:
<223> OTHER INFORMATION: Antibody VL CDR3 sequence
<220> FEATURE:
<221> NAME/KEY: MISC_FEATURE
<222> LOCATION: (2)..(2)
<223> OTHER INFORMATION: Any amino acid, preferably Ser or Asn, most
      preferably Ser
<220> FEATURE:
<221> NAME/KEY: MISC_FEATURE
<222> LOCATION: (3)..(3)
<223> OTHER INFORMATION: Any amino acid, preferably Tyr, Ser, Ile, Asn
      or Thr, more preferably Tyr, Ser, or Asn, most preferably Asn
<220> FEATURE:
<221> NAME/KEY: MISC_FEATURE
<222> LOCATION: (4)..(4)
<223> OTHER INFORMATION: Any amino acid, preferably Ser or Tyr, more
      preferably Tyr

<400> SEQUENCE: 49

Arg Xaa Xaa Xaa Pro
1               5

<210> SEQ ID NO 50
<211> LENGTH: 7
<212> TYPE: PRT
<213> ORGANISM: Artificial Sequence
<220> FEATURE:
<223> OTHER INFORMATION: Antibody VL CDR3 sequence
<220> FEATURE:
<221> NAME/KEY: MISC_FEATURE
<222> LOCATION: (3)..(3)
<223> OTHER INFORMATION: Any amino acid, preferably Ser or Asn, most
      preferably Ser
<220> FEATURE:
<221> NAME/KEY: MISC_FEATURE
<222> LOCATION: (4)..(4)
<223> OTHER INFORMATION: Any amino acid, preferably Tyr, Ser, Ile, Asn
      or Thr, more preferably Tyr, Ser, or Asn, most preferably Asn
<220> FEATURE:
<221> NAME/KEY: MISC_FEATURE
<222> LOCATION: (5)..(5)
<223> OTHER INFORMATION: Any amino acid, preferably Ser or Tyr, more
      preferably Tyr

<400> SEQUENCE: 50

Gln Arg Xaa Xaa Xaa Pro Pro
1               5

<210> SEQ ID NO 51
<211> LENGTH: 10
<212> TYPE: PRT
<213> ORGANISM: Artificial Sequence
<220> FEATURE:
<223> OTHER INFORMATION: Antibody VL CDR3 sequence
<220> FEATURE:
<221> NAME/KEY: MISC_FEATURE
<222> LOCATION: (4)..(4)
<223> OTHER INFORMATION: Any amino acid, preferably Ser or Asn, most
      preferably Ser
<220> FEATURE:
<221> NAME/KEY: MISC_FEATURE
<222> LOCATION: (5)..(5)
<223> OTHER INFORMATION: Any amino acid, preferably Tyr, Ser, Ile, Asn
      or Thr, more preferably Tyr, Ser, or Asn, most preferably Asn
<220> FEATURE:
<221> NAME/KEY: MISC_FEATURE
<222> LOCATION: (6)..(6)
<223> OTHER INFORMATION: Any amino acid, preferably Ser or Tyr, more
      preferably Tyr

<400> SEQUENCE: 51
```

```
Gln Gln Arg Xaa Xaa Xaa Pro Pro Trp Thr
1               5                   10

<210> SEQ ID NO 52
<211> LENGTH: 5
<212> TYPE: PRT
<213> ORGANISM: Artificial Sequence
<220> FEATURE:
<223> OTHER INFORMATION: Antibody VL CDR1 sequence
<220> FEATURE:
<221> NAME/KEY: MISC_FEATURE
<222> LOCATION: (4)..(4)
<223> OTHER INFORMATION: Any amino acid, preferably Ser or Asn, most
      preferably Ser

<400> SEQUENCE: 52

Ser Ser Val Xaa Tyr
1               5

<210> SEQ ID NO 53
<211> LENGTH: 3
<212> TYPE: PRT
<213> ORGANISM: Artificial Sequence
<220> FEATURE:
<223> OTHER INFORMATION: Antibody VL CDR2 sequence

<400> SEQUENCE: 53

Ser Thr Ser
1

<210> SEQ ID NO 54
<211> LENGTH: 8
<212> TYPE: PRT
<213> ORGANISM: Artificial Sequence
<220> FEATURE:
<223> OTHER INFORMATION: Antibody VH  CDR2 sequence

<400> SEQUENCE: 54

Ile Asn Pro Tyr Asn Gly Gly Thr
1               5

<210> SEQ ID NO 55
<211> LENGTH: 10
<212> TYPE: PRT
<213> ORGANISM: Artificial Sequence
<220> FEATURE:
<223> OTHER INFORMATION: Antibody VH CDR3 sequence

<400> SEQUENCE: 55

Ala Arg Asp Tyr Gly Tyr Val Leu Asp Tyr
1               5                   10

<210> SEQ ID NO 56
<211> LENGTH: 5
<212> TYPE: PRT
<213> ORGANISM: Artificial Sequence
<220> FEATURE:
<223> OTHER INFORMATION: Antibody VL CDR1 sequence

<400> SEQUENCE: 56

Ser Ser Val Ser Tyr
1               5

<210> SEQ ID NO 57
<211> LENGTH: 10
<212> TYPE: PRT
<213> ORGANISM: Artificial Sequence
<220> FEATURE:
```

<223> OTHER INFORMATION: Antibody VL CDR3 sequence

<400> SEQUENCE: 57

Gln Gln Arg Ser Ile Tyr Pro Pro Trp Thr
1               5                   10

<210> SEQ ID NO 58
<211> LENGTH: 10
<212> TYPE: PRT
<213> ORGANISM: Artificial Sequence
<220> FEATURE:
<223> OTHER INFORMATION: Antibody VH CDR3 sequence

<400> SEQUENCE: 58

Ala Arg Asp Tyr Gly Phe Val Leu Asp Tyr
1               5                   10

<210> SEQ ID NO 59
<211> LENGTH: 10
<212> TYPE: PRT
<213> ORGANISM: Artificial Sequence
<220> FEATURE:
<223> OTHER INFORMATION: Antibody VL CDR3 sequence

<400> SEQUENCE: 59

Gln Gln Arg Ser Asn Tyr Pro Pro Trp Thr
1               5                   10

<210> SEQ ID NO 60
<211> LENGTH: 8
<212> TYPE: PRT
<213> ORGANISM: Artificial Sequence
<220> FEATURE:
<223> OTHER INFORMATION: Antibody VH CDR2 sequence

<400> SEQUENCE: 60

Ile Asn Pro Tyr Asn Gly Gly Ile
1               5

<210> SEQ ID NO 61
<211> LENGTH: 10
<212> TYPE: PRT
<213> ORGANISM: Artificial Sequence
<220> FEATURE:
<223> OTHER INFORMATION: Antibody VH CDR3 sequence

<400> SEQUENCE: 61

Ala Arg Asp Phe Gly Tyr Val Leu Asp Tyr
1               5                   10

<210> SEQ ID NO 62
<211> LENGTH: 10
<212> TYPE: PRT
<213> ORGANISM: Artificial Sequence
<220> FEATURE:
<223> OTHER INFORMATION: Antibody VL CDR3 sequence

<400> SEQUENCE: 62

Gln Gln Arg Ser Thr Tyr Pro Pro Trp Thr
1               5                   10

<210> SEQ ID NO 63
<211> LENGTH: 8
<212> TYPE: PRT
<213> ORGANISM: Artificial Sequence
<220> FEATURE:
<223> OTHER INFORMATION: Antibody VH CDR2 sequence

```
<400> SEQUENCE: 63

Ile Asn Pro Tyr Asn Gly Gly Ser
1               5

<210> SEQ ID NO 64
<211> LENGTH: 10
<212> TYPE: PRT
<213> ORGANISM: Artificial Sequence
<220> FEATURE:
<223> OTHER INFORMATION: Antibody VH CDR3 sequence

<400> SEQUENCE: 64

Ala Arg Asp Tyr Gly Tyr Val Phe Asp Tyr
1               5                   10

<210> SEQ ID NO 65
<211> LENGTH: 5
<212> TYPE: PRT
<213> ORGANISM: Artificial Sequence
<220> FEATURE:
<223> OTHER INFORMATION: Antibody VL CDR1 sequence

<400> SEQUENCE: 65

Ser Ser Val Asn Tyr
1               5

<210> SEQ ID NO 66
<211> LENGTH: 10
<212> TYPE: PRT
<213> ORGANISM: Artificial Sequence
<220> FEATURE:
<223> OTHER INFORMATION: Antibody VL CDR3 sequence

<400> SEQUENCE: 66

Gln Gln Arg Asn Asn Tyr Pro Pro Trp Thr
1               5                   10
```

ANTIBODIES SPECIFIC FOR CLAUDIN 6 (CLDN6)

CROSS-REFERENCE TO RELATED APPLICATIONS

This application is a divisional of U.S. patent application Ser. No. 15/133,783, filed on Apr. 20, 2016, which is a continuation of U.S. patent application Ser. No. 13/503,461, now U.S. Pat. No. 9,487,584, filed on Aug. 13, 2012 as a National Stage Entry of PCT/EP2010/006888, which was filed on Nov. 11, 2010 and claimed priority to European Patent Application Number 09014136.7 and U.S. Patent Application Ser. No. 61/260,202, which were filed on Nov. 11, 2009, and European Patent Application Number 10006956.6 and U.S. Patent Application Ser. No. 61/361,618, which were filed on Jul. 6, 2010. The contents of each of the aforementioned applications are incorporated herein by reference in their entireties.

BACKGROUND

Antibodies have been successfully introduced into the clinic for use in cancer therapy and have emerged as the most promising therapeutics in oncology over the last decade. Antibody-based therapies for cancer have the potential of higher specificity and lower side effect profile as compared to conventional drugs. The reason is a precise distinction between normal and neoplastic cells by antibodies and the fact that their mode of action relies on less toxic immunological anti-tumor mechanisms, such as complement activation and recruitment of cytotoxic immune cells.

Claudins are integral membrane proteins located within the tight junctions of epithelia and endothelia. Claudins are predicted to have four transmembrane segments with two extracellular loops, and N and C termini located in the cytoplasm. The claudin (CLDN) family of transmembrane proteins plays a critical role in the maintenance of epithelial and endothelial tight junctions and might also play a role in the maintenance of the cytoskeleton and in cell signaling. The differential expression of these proteins between tumor and normal cells, in addition to their membrane localization, makes them attractive targets for cancer immunotherapy and the use of antibody-based therapeutics for targeting CLDNs in cancer therapy promises a high level of therapeutic specificity.

However, the clinical application of CLDN-targeted therapeutics faces several obstacles. The ubiquitous expression of CLDNs in the body and the critical role of CLDNs in the maintenance of tight junctions requires target specificity of CLDN-targeted therapeutics in order to maximize treatment specificity and minimize systemic toxicity.

WO 2009/087978 relates to anti-CLDN6 antibodies and to their use as anti-cancer agents. In particular, the monoclonal antibodies designated AB3-1, AE1-16, AE49-11, and AE3-20 are described. However, none of these antibodies was specific for CLDN6 as shown by FACS analysis in Example 5. Antibody AE3-20 reacted with CLDN9, while the antibodies AE1-16 and AE49-11 showed considerable reactivity with CLDN9 and also reacted with CLDN4. The binding of antibody AB3-1 to CLDN6 was as strong as its binding to CLDN9. It is described in Example 7 that the antibody AE49-11 when administered to a mouse tumor model tended to inhibit tumor growth and had a life-prolonging effect. However, given the unspecificity of the antibody used, it remains unclear whether the described effects are due to binding of the antibody to CLDN6.

Thus, up to now, no CLDN6-specific antibody has been described that selectively binds to the surface of cells expressing CLDN6. However, such specific antibody would be required for antibody-based therapeutic approaches using CLDN6 as a target.

The sequence alignment of CLDN3, CLDN4, CLDN6 and CLDN9 shown in FIG. 1 illustrates that there is a high degree of conservation of CLDN6 to other claudin proteins. This high homology of CLDN6 with other claudin proteins, in particular CLDN9 and CLDN4, and the fact that WO 2009/087978 failed to provide CLDN6-specific antibodies suggest that it might not be possible to produce antibodies specifically binding to CLDN6.

SUMMARY OF THE INVENTION

The experimental results disclosed herein confirm that CLDN6 is expressed in different human cancer cells while expression in normal tissues is limited to placenta.

Furthermore, the present invention for the first time describes the successful production of CLDN6-specific antibodies capable of binding to the surface of intact cells that express CLDN6. FACS analyzes of intact cells expressing CLDN6 showed the specific binding of anti-CLDN6 antibodies while no binding was observed for cells expressing other claudin proteins, in particular, CLDN3, CLDN4 and CLDN9, or cells not expressing any of these CLDN proteins. Thus, the present invention unexpectedly demonstrates that an antibody can be produced specifically performing an antigen-antibody reaction with CLDN6 on the surface of cells expressing CLDN6, but not substantially performing the antigen-antibody reaction with other highly homologous claudins.

The present invention generally provides antibodies useful as therapeutics for treating and/or preventing diseases associated with cells expressing CLDN6 and being characterized by association of CLDN6 with their cell surface, including tumor-related diseases, in particular cancer, such as ovarian cancer, in particular ovarian adenocarcinoma and ovarian teratocarcinoma, lung cancer, including small cell lung cancer (SCLC) and non-small cell lung cancer (NSCLC), in particular squamous cell lung carcinoma and adenocarcinoma, gastric cancer, breast cancer, hepatic cancer, pancreatic cancer, skin cancer, in particular basal cell carcinoma and squamous cell carcinoma, malignant melanoma, head and neck cancer, in particular malignant pleomorphic adenoma, sarcoma, in particular synovial sarcoma and carcinosarcoma, bile duct cancer, cancer of the urinary bladder, in particular transitional cell carcinoma and papillary carcinoma, kidney cancer, in particular renal cell carcinoma including clear cell renal cell carcinoma and papillary renal cell carcinoma, colon cancer, small bowel cancer, including cancer of the ileum, in particular small bowel adenocarcinoma and adenocarcinoma of the ileum, testicular embryonal carcinoma, placental choriocarcinoma, cervical cancer, testicular cancer, in particular testicular seminoma, testicular teratoma and embryonic testicular cancer, uterine cancer, a germ cell tumor such as a teratocarcinoma or an embryonal carcinoma, in particular a germ cell tumor of the testis, and the metastatic forms thereof.

In one aspect the invention relates to an antibody which is capable of binding to CLDN6 associated with the surface of a cell that expresses CLDN6. Preferably, the antibody is not substantially capable of binding to CLDN9 associated with the surface of a cell that expresses CLDN9. Preferably, the antibody is not substantially capable of binding to CLDN4 associated with the surface of a cell that expresses CLDN4 and/or is not substantially capable of binding to CLDN3 associated with the surface of a cell that expresses CLDN3. Most preferably, the antibody is not substantially capable of binding to a CLDN protein other than CLDN6 associated with the surface of a cell that expresses said CLDN protein and is specific for CLDN6. Preferably, said cell expressing said CLDN protein is an intact cell, in particular a non-permeabilized cell, and said CLDN protein associated with the surface of a cell has a native, i.e. non-denatured, conformation. Preferably, the antibody is capable of binding to one or more epitopes of CLDN6 in their native conformation.

In one embodiment, the antibody is capable of binding to an epitope located within an extracellular portion of CLDN6, wherein said extracellular portion of CLDN6 preferably comprises the amino acid sequence of any one of SEQ ID NO: 6, SEQ ID NO: 7, SEQ ID NO: 14 and SEQ ID NO: 15, preferably the amino acid sequence of SEQ ID NO: 6 or SEQ ID NO: 7, more preferably the amino acid sequence of SEQ ID NO: 6. Preferably, the antibody is capable of binding to an epitope located within the amino acid sequence of any one of SEQ ID NO: 6, SEQ ID NO: 7, SEQ ID NO: 14 and SEQ ID NO: 15, preferably the amino acid sequence of SEQ ID NO: 6 or SEQ ID NO: 7.

In one embodiment, the antibody is capable of binding to CLDN6 by interacting at least with one, preferably more than one, such as 2, 3, 4 or 5, preferably all amino acids selected from the group consisting of Thr33, Phe35, Gly37, Ser39, Ile40 and Leu151, preferably by interacting at least with one, preferably more than one, preferably all amino acids selected from the group consisting of Thr33, Phe35, Gly37, Ser39 and Ile40, more preferably by interacting at least with one, preferably more than one, preferably all amino acids selected from the group consisting of Phe35, Gly37, Ser39 and Ile40 or consisting of Thr33, Phe35, Gly37 and Ser39, and, in particular, by interacting at least with one, preferably more than one, preferably all amino acids selected from the group consisting of Phe35, Gly37 and Ser39. Preferably, the antibody does not interact with one or more, preferably all amino acids selected from the group consisting of Glu154, Ala155, Arg158 and Gly161, and preferably does not interact with one or more, preferably all amino acids selected from the group consisting of Arg158 and Gly161.

The interaction between an antibody and CLDN6, in particular in its native conformation, can be analyzed by an alanine scanning mutagenesis of amino acids. CLDN6 mutants can be assessed for their ability to be bound by specific monoclonal antibodies. Impaired binding of a specific monoclonal antibody to a CLDN6 mutant suggest that the mutated amino acid is an important contact residue. Binding can be analyzed, for example, by flow cytometry.

In one embodiment, the antibody is obtainable by a method comprising the step of immunizing an animal with a peptide having the amino acid sequence of any one of SEQ ID NO: 6, SEQ ID NO: 7, SEQ ID NO: 14 and SEQ ID NO: 15, preferably the amino acid sequence of SEQ ID NO: 6 or SEQ ID NO: 7 or an immunologically equivalent peptide, or a nucleic acid or host cell expressing said peptide.

In different embodiments, the CLDN6 to which the antibody is capable of binding has the amino acid sequence of SEQ ID NO: 2 or the amino acid sequence of SEQ ID NO: 8. It is particularly preferred that the antibody is capable of binding to CLDN6 having the amino acid sequence of SEQ ID NO: 2 and capable of binding to CLDN6 having the amino acid sequence of SEQ ID NO: 8.

In one embodiment, an antibody of the invention comprises an antibody heavy chain comprising at least one, preferably two, more preferably all three of the CDR sequences of an antibody heavy chain sequence selected from SEQ ID NOs: 34, 36, 38 and 40, or a variant thereof. The CDR sequences are marked by a box in the above mentioned antibody heavy chain sequences given in FIG. 25.

In one embodiment, an antibody of the invention comprises an antibody heavy chain comprising the CDR3 sequence Xaa1 Gly Xaa2 Val Xaa3, wherein Xaa1 is any amino acid, preferably an aromatic amino acid, more preferably Phe or Tyr, most preferably Tyr, Xaa2 is any amino acid, preferably an aromatic amino acid, more preferably Phe or Tyr, most preferably Tyr, and Xaa3 is any amino acid, preferably Leu or Phe, more preferably Leu. In one embodiment, an antibody of the invention comprises an antibody heavy chain comprising the CDR3 sequence Asp Xaa1 Gly Xaa2 Val Xaa3 or Xaa1 Gly Xaa2 Val Xaa3 Asp, wherein Xaa1, Xaa2 and Xaa3 are as defined above. In one embodiment, an antibody of the invention comprises an antibody heavy chain comprising the CDR3 sequence Asp Xaa1 Gly Xaa2 Val Xaa3 Asp, wherein Xaa1, Xaa2 and Xaa3 are as defined above. In one embodiment, an antibody of the invention comprises an antibody heavy chain comprising the CDR3 sequence Ala Arg Asp Xaa1 Gly Xaa2 Val Xaa3 Asp Tyr, wherein Xaa1, Xaa2 and Xaa3 are as defined above. In one embodiment, an antibody according to the foregoing embodiments comprises an antibody heavy chain comprising the CDR1 sequence according to SEQ ID NO: 47 or a variant thereof and/or the CDR2 sequence according to SEQ ID NO: 48 or a variant thereof.

In one embodiment, an antibody of the invention comprises an antibody heavy chain comprising an antibody heavy chain sequence selected from SEQ ID NOs: 34, 36, 38 and 40 or a variant thereof.

In one embodiment, an antibody of the invention comprises an antibody light chain comprising at least one, preferably two, more preferably all three of the CDR sequences of an antibody light chain sequence selected from SEQ ID NOs: 35, 37, 39 and 41, or a variant thereof. The CDR sequences are marked by a box in the above mentioned antibody light chain sequences given in FIG. 26.

In one embodiment, an antibody of the invention comprises an antibody light chain comprising the CDR3 sequence Arg Xaa1 Xaa2 Xaa3 Pro, wherein Xaa1 is any amino acid, preferably Ser or Asn, most preferably Ser, Xaa2 is any amino acid, preferably Tyr, Ser, Ile, Asn or Thr, more preferably Tyr, Ser, or Asn, most preferably Asn, and Xaa3 is any amino acid, preferably Ser or Tyr, more preferably Tyr. In one embodiment, an antibody of the invention comprises an antibody light chain comprising the CDR3 sequence Gln Arg Xaa1 Xaa2 Xaa3 Pro Pro, wherein Xaa1, Xaa2 and Xaa3 are as defined above. In one embodiment, an antibody of the invention comprises an antibody light chain comprising the CDR3 sequence Gln Gln Arg Xaa1 Xaa2 Xaa3 Pro Pro Trp Thr, wherein Xaa1, Xaa2 and Xaa3 are as defined above. In one embodiment, an antibody according to the foregoing embodiments comprises an antibody light chain comprising the CDR1 sequence according to SEQ ID NO: 52 or a variant thereof and/or the CDR2 sequence according to SEQ ID NO: 53 or a variant thereof.

In one embodiment, an antibody of the invention comprises an antibody light chain comprising an antibody light chain sequence selected from SEQ ID NOs: 35, 37, 39 and 41 or a variant thereof.

In various embodiments, an antibody of the invention comprises an antibody heavy chain as discussed above and an antibody light chain as also discussed above.

In one embodiment, an antibody of the invention comprises:
(i) an antibody heavy chain comprising at least one, preferably two, more preferably all three of the CDR sequences of an antibody heavy chain sequence of SEQ ID NO: x, or a variant thereof, and
(ii) an antibody light chain comprising at least one, preferably two, more preferably all three of the CDR sequences of an antibody light chain sequence of SEQ ID NO: x+1, or a variant thereof; wherein x selected from 34, 36, 38 and 40.

The CDR sequences are marked by a box in the above mentioned antibody heavy chain sequences and antibody light chain sequences, respectively, given in FIG. 25 and FIG. 26, respectively.

In one embodiment, an antibody of the invention comprises:
(i) an antibody heavy chain comprising a CDR3 sequence selected from the group consisting of Xaa1 Gly Xaa2 Val Xaa3, Asp Xaa1 Gly Xaa2 Val Xaa3, Xaa1 Gly Xaa2 Val Xaa3 Asp, Asp Xaa1 Gly Xaa2 Val Xaa3 Asp, and Ala Arg Asp Xaa1 Gly Xaa2 Val Xaa3 Asp Tyr, wherein Xaa1 is any amino acid, preferably an aromatic amino acid, more preferably Phe or Tyr, most preferably Tyr, Xaa2 is any amino acid, preferably an aromatic amino acid, more preferably Phe or Tyr, most preferably Tyr, and Xaa3 is any amino acid, preferably Leu or Phe, more preferably Leu, and
(ii) an antibody light chain comprising a CDR3 sequence selected from the group consisting of Arg Xaa1 Xaa2 Xaa3 Pro, Gln Arg Xaa1 Xaa2 Xaa3 Pro Pro, Gln Gln Arg Xaa1 Xaa2 Xaa3 Pro Pro Trp Thr, wherein Xaa1 is any amino acid, preferably Ser or Asn, most preferably Ser, Xaa2 is any amino acid, preferably Tyr, Ser, Ile, Asn or Thr, more preferably Tyr, Ser, or Asn, most preferably Asn, and Xaa3 is any amino acid, preferably Ser or Tyr, more preferably Tyr.

In one embodiment, an antibody according to the foregoing embodiments comprises (i) an antibody heavy chain comprising the CDR1 sequence according to SEQ ID NO: 47 or a variant thereof and/or the CDR2 sequence according to SEQ ID NO: 48 or a variant thereof and/or (ii) an antibody light chain comprising the CDR1 sequence according to SEQ ID NO: 52 or a variant thereof and/or the CDR2 sequence according to SEQ ID NO: 53 or a variant thereof.

In one embodiment, an antibody of the invention comprises:
(i) an antibody heavy chain comprising an antibody heavy chain sequence of SEQ ID NO: x or a variant thereof, and
(ii) an antibody light chain comprising an antibody light chain sequence of SEQ ID NO: x+1 or a variant thereof; wherein x selected from 34, 36, 38 and 40.

In preferred embodiments, the antibody has one or more of the following activities: (i) killing of a cell expressing CLDN6, (ii) inhibition of proliferation of a cell expressing CLDN6, (iii) inhibition of colony formation of a cell expressing CLDN6, (iv) mediating remission, i.e. reduction in size, preferably complete remission, i.e. complete disappearance, of established tumors, (v) prevention of the formation or re-formation of tumors, and (vi) inhibition of metastasis of a cell expressing CLDN6. Accordingly, the antibody may be used for one or more of the foregoing, in particular when administered to a patient. Such killing of cells and/or inhibition of one or more activities of cells can be utilized therapeutically as described herein. In particular, killing of cells, inhibition of proliferation of cells and/or inhibition of colony formation of cells can be utilized for treating or preventing cancer, including cancer metastasis. Inhibition of proliferation, colony formation and/or metastasis of cells can be utilized, in particular, for treating or preventing cancer metastasis and the metastatic spread of cancer cells. Preferably the antibody of the invention mediates killing of cells by inducing complement dependent cytotoxicity (CDC) mediated lysis, antibody dependent cellular cytotoxicity (ADCC) mediated lysis, apoptosis, homotypic adhesion, and/or phagocytosis, preferably by inducing CDC mediated lysis and/or ADCC mediated lysis. However, the present invention also includes embodiments wherein the antibody exerts its activity as described herein such as killing of cells and/or inhibition of one or more activities of cells, e.g. cell proliferation and/or colony formation, without inducing complement dependent cytotoxicity (CDC) mediated lysis, antibody dependent cellular cytotoxicity (ADCC) mediated lysis, apoptosis, homotypic adhesion, and/or phagocytosis. For example, the antibody of the invention may also exert an effect simply by binding to CLDN6 on the cell surface, thus, e.g. blocking proliferation of the cells. In one embodiment the antibody of the invention does not induce CDC mediated lysis of cells.

Preferably, ADCC mediated lysis of cells takes place in the presence of effector cells, which in particular embodiments are selected from the group consisting of monocytes, mononuclear cells, NK cells and PMNs, and phagocytosis is by macrophages.

The activity of inhibiting or reducing proliferation of cells expressing CLDN6, preferably cancer cells, can be measured in vitro by determining proliferation of CLDN6-expressing cancer cells in an assay using bromodeoxyuridine (5-bromo-2-deoxyuridine, BrdU). BrdU is a synthetic nucleoside which is an analogue of thymidine and can be incorporated into the newly synthesized DNA of replicating cells (during the S phase of the cell cycle), substituting for thymidine during DNA replication. Detecting the incorporated chemical using, for example, antibodies specific for BrdU indicates cells that were actively replicating their DNA.

The activity of inhibiting or reducing colony formation of cells expressing CLDN6, preferably cancer cells, can be measured in vitro in a clonogenic assay. A clonogenic assay is a microbiology technique for studying the effectiveness of specific agents on the survival and proliferation of cells. It is frequently used in cancer research laboratories to determine the effect of drugs or radiation on proliferating tumor cells. The experiment involves three major steps: (i) applying a treatment to a sample of cells, in particular cancer cells, (ii) plating the cells in a tissue culture vessel and (iii) allowing the cells to grow. The colonies produced are fixed, stained, and counted. Colony formation is of importance with respect to the formation of metastases if individual tumor cells colonize organs. The inhibitory activity of the antibodies indicates their potential in suppressing the formation of metastases. Antibodies having the activity of inhibiting or reducing colony formation in a clonogenic assay are particularly useful for treating or preventing metastasis and the metastatic spread of cancer cells, in particular of the cancer types mentioned herein.

In preferred embodiments, the antibody exhibits one or more immune effector functions against a cell carrying CLDN6 in its native conformation, wherein the one or more immune effector functions are preferably selected from the group consisting of complement dependent cytotoxicity (CDC), antibody-dependent cell-mediated cytotoxicity (ADCC), induction of apoptosis, and inhibition of proliferation, preferably the effector functions are ADCC and/or CDC.

Preferably said one or more activities or one or more immune effector functions exhibited by said antibody are induced by binding of said antibody to CLDN6, preferably to an epitope located within an extracellular portion of CLDN6, wherein said extracellular portion of CLDN6 preferably comprises the amino acid sequence of any one of SEQ ID NO: 6, SEQ ID NO: 7, SEQ ID NO: 14 and SEQ ID NO: 15, preferably the amino acid sequence of SEQ ID NO: 6 or SEQ ID NO: 7, more preferably the amino acid sequence of SEQ ID NO: 6.

According to the invention, a cell expressing CLDN6 is preferably characterized by association of CLDN6 with its cell surface. A cell expressing CLDN6 or a cell carrying CLDN6 in its native conformation preferably is a tumor cell, such as a cancer cell, preferably a cancer cell from a cancer selected from the group consisting of ovarian cancer, in particular ovarian adenocarcinoma and ovarian teratocarcinoma, lung cancer, including small cell lung cancer (SCLC) and non-small cell lung cancer (NSCLC), in particular squamous cell lung carcinoma and adenocarcinoma, gastric cancer, breast cancer, hepatic cancer, pancreatic cancer, skin cancer, in particular basal cell carcinoma and squamous cell carcinoma, malignant melanoma, head and neck cancer, in particular malignant pleomorphic adenoma, sarcoma, in particular synovial sarcoma and carcinosarcoma, bile duct cancer, cancer of the urinary bladder, in particular transitional cell carcinoma and papillary carcinoma, kidney cancer, in particular renal cell carcinoma including clear cell renal cell carcinoma and papillary renal cell carcinoma, colon cancer, small bowel cancer, including cancer of the ileum, in particular small bowel adenocarcinoma and adenocarcinoma of the ileum, testicular embryonal carcinoma, placental choriocarcinoma, cervical cancer, testicular cancer, in particular testicular seminoma, testicular teratoma and embryonic testicular cancer, uterine cancer, a germ cell tumor such as a teratocarcinoma or an embryonal carcinoma, in particular a germ cell tumor of the testis, and the metastatic forms thereof.

The antibody of the invention may be attached to one or more therapeutic effector moieties, e.g., radiolabels, cytotoxins, therapeutic enzymes, agents that induce apoptosis, and the like in order to provide for targeted cytotoxicity, i.e., killing of tumor cells.

In one embodiment the antibody of the invention (i) binds to cells expressing CLDN6 and being characterized by association of CLDN6 with their cell surface, and (ii) does not bind to cells not expressing CLDN6 and not being characterized by association of CLDN6 with their cell surface. The antibody of the invention preferably (i) mediates killing and/or inhibits proliferation of cells expressing CLDN6 and being characterized by association of CLDN6 with their cell surface, and (ii) does not mediate killing and/or do not inhibit proliferation of cells not expressing CLDN6 and not being characterized by association of CLDN6 with their cell surface.

In particular preferred embodiments, the antibody of the invention binds to native epitopes of CLDN6 present on the surface of living cells such as those of SEQ ID NOs: 6 or 7. In further preferred embodiments, the antibody of the invention is specific for CLDN6-expressing cancer cells and does not bind to cancer cells not expressing CLDN6.

Antibodies of the invention may be derived from different species, including but not limited to mouse, rat, rabbit, guinea pig and human. Antibodies of the invention also include chimeric molecules in which an antibody constant region derived from one species, preferably human, is combined with the antigen binding site derived from another species. Moreover antibodies of the invention include humanized molecules in which the antigen binding sites of an antibody derived from a non-human species are combined with constant and framework regions of human origin.

Antibodies of the invention include polyclonal and monoclonal antibodies and include IgG2a (e.g. IgG2a κ, λ), IgG2b (e.g. IgG2b, κ, λ), IgG3 (e.g. IgG3, κ, λ) and IgM antibodies. However, other antibody isotypes are also encompassed by the invention, including IgG1, IgA1, IgA2, secretory IgA, IgD, and IgE antibodies. The antibodies can be whole antibodies or antigen-binding fragments thereof including, for example, Fab, F(ab)$_2$, Fv, single chain Fv fragments or bispecific antibodies. Furthermore, the antigen-binding fragments include binding-domain immunoglobulin fusion proteins comprising (i) a binding domain polypeptide (such as a heavy chain variable region or a light chain variable region) that is fused to an immunoglobulin hinge region polypeptide, (ii) an immunoglobulin heavy chain CH2 constant region fused to the hinge region, and (iii) an immunoglobulin heavy chain CH3 constant region fused to the CH2 constant region. Such binding-domain immunoglobulin fusion proteins are further disclosed in US2003/0118592 and US 2003/0133939.

The antibody of the invention preferably is a monoclonal, chimeric, human or humanized antibody, or a fragment of an antibody. Antibodies of the invention include fully human antibodies. Such antibodies may be produced in a non-human transgenic animal, e.g., a transgenic mouse, capable of producing multiple isotypes of human monoclonal antibodies to CLDN6 by undergoing V-D-J recombination and isotype switching. Such transgenic animal can also be a transgenic rabbit for producing polyclonal antibodies such as disclosed in US 2003/0017534.

Antibodies of the present invention preferably dissociate from CLDN6 with a dissociation equilibrium constant (KD) of approximately 1-100 nM or less. Preferably, antibodies of the invention do not cross-react with related cell-surface antigens and thus do not inhibit their function.

In preferred embodiments, antibodies of the present invention can be characterized by one or more of the following properties:
a) specificity for CLDN6;
b) a binding affinity to CLDN6 of about 100 nM or less, preferably, about 5-10 nM or less and, more preferably, about 1-3 nM or less,
c) the ability to induce CDC of cells which express CLDN6 and are characterized by association of CLDN6 with their cell surface;
d) the ability to inhibit the growth of cells which express CLDN6 and are characterized by association of CLDN6 with their cell surface;
e) the ability to induce apoptosis of cells which express CLDN6 and are characterized by association of CLDN6 with their cell surface;
f) the ability to induce homotypic adhesion of cells which express CLDN6 and are characterized by association of CLDN6 with their cell surface;
g) the ability to induce ADCC of cells which express CLDN6 and are characterized by association of CLDN6 with their cell surface in the presence of effector cells;
h) the ability to prolong survival of a subject having tumor cells which express CLDN6 and are characterized by association of CLDN6 with their cell surface;

i) the ability to deplete cells which express CLDN6 and are characterized by association of CLDN6 with their cell surface;
j) the ability to aggregate CLDN6 on the surface of living cells.

A preferred antibody described herein is an antibody produced by or obtainable from a hybridoma cell deposited at the DSMZ (Inhoffenstr. 7B, 38124 Braunschweig, Germany) and having one of the following designations and accession numbers:
1. GT512muMAB 59A, accession no. DSM ACC3067, deposited on Jun. 21, 2010;
2. GT512muMAB 60A, accession no. DSM ACC3068, deposited on Jun. 21, 2010;
3. GT512muMAB 61D, accession no. DSM ACC3069, deposited on Jun. 21, 2010;
4. GT512muMAB 64A, accession no. DSM ACC3070, deposited on Jun. 21, 2010;
5. GT512muMAB 65A, accession no. DSM ACC3071, deposited on Jun. 21, 2010;
6. GT512muMAB 66B, accession no. DSM ACC3072, deposited on Jun. 21, 2010;
7. GT512muMAB 67A, accession no. DSM ACC3073, deposited on Jun. 21, 2010;
8. GT512muMAB 55A, accession no. DSM ACC3089, deposited on Aug. 31, 2010; or
9. GT512muMAB 89A, accession no. DSM ACC3090, deposited on Aug. 31, 2010.

Antibodies of the invention are designated herein by referring to the designation of the antibody and/or by referring to the clone producing the antibody, e.g. muMAB 59A.

Further preferred antibodies are those having the specificity of the antibodies produced by and obtainable from the above-described hybridomas and, in particular, those comprising an antigen binding portion or antigen binding site, in particular a variable region, identical or highly homologous to that of the antibodies produced by and obtainable from the above-described hybridomas. It is contemplated that preferred antibodies are those having CDR regions either identical or highly homologous to the regions of antibodies produced by and obtainable from the above-described hybridomas. By "highly homologous" it is contemplated that from 1 to 5, preferably from 1 to 4, such as 1 to 3 or 1 or 2 substitutions may be made in each CDR region. Particularly preferred antibodies are the chimerized and humanized forms of the antibodies produced by and obtainable from the above-described hybridomas.

Thus, an antibody of the invention may be selected from the group consisting of (i) an antibody produced by or obtainable from a clone deposited under the accession no. DSM ACC3067 (GT512muMAB 59A), DSM ACC3068 (GT512muMAB 60A), DSM ACC3069 (GT512muMAB 61D), DSM ACC3070 (GT512muMAB 64A), DSM ACC3071 (GT512muMAB 65A), DSM ACC3072 (GT512muMAB 66B), DSM ACC3073 (GT512muMAB 67A), DSM ACC3089 (GT512muMAB 55A), or DSM ACC3090 (GT512muMAB 89A), (ii) an antibody which is a chimerized or humanized form of the antibody under (i), (iii) an antibody which has the specificity of the antibody under (i), and (iv) an antibody comprising the antigen binding portion or antigen binding site of the antibody under (i). The antigen binding portion or antigen binding site of the antibody under (i) may comprise the variable region of the antibody under (i).

The present invention also relates to a cell such as a hybridoma cell producing an antibody as described herein.

Preferred hybridoma cells are those deposited at the DSMZ (Inhoffenstr. 7B, 38124 Braunschweig, Germany) and having one of the following designations and accession numbers:
1. GT512muMAB 59A, accession no. DSM ACC3067, deposited on Jun. 21, 2010;
2. GT512muMAB 60A, accession no. DSM ACC3068, deposited on Jun. 21, 2010;
3. GT512muMAB 61D, accession no. DSM ACC3069, deposited on Jun. 21, 2010;
4. GT512muMAB 64A, accession no. DSM ACC3070, deposited on Jun. 21, 2010;
5. GT512muMAB 65A, accession no. DSM ACC3071, deposited on Jun. 21, 2010;
6. GT512muMAB 66B, accession no. DSM ACC3072, deposited on Jun. 21, 2010;
7. GT512muMAB 67A, accession no. DSM ACC3073, deposited on Jun. 21, 2010;
8. GT512muMAB 55A, accession no. DSM ACC3089, deposited on Aug. 31, 2010; or
9. GT512muMAB 89A, accession no. DSM ACC3090, deposited on Aug. 31, 2010.

The anti-CLDN6 antibodies of the present invention can be derivatized, linked to or co-expressed to other binding specificities. In a particular embodiment, the invention provides a bispecific or multispecific molecule comprising at least one first binding specificity for CLDN6 (e.g., an anti-CLDN6 antibody or mimetic thereof), and a second binding specificity for a effector cell, such as a binding specificity for an Fc receptor (e.g., a Fc-gamma receptor, such as Fc-gamma RI, or any other Fc receptor) or a T cell receptor, e.g., CD3.

Accordingly, the present invention includes bispecific and multispecific molecules that bind to both CLDN6 and to an Fc receptor or a T cell receptor, e.g. CD3. Examples of Fc receptors are IgG receptor, Fc-gamma receptor (FcγR), such as FcγRI (CD64), FcγRII (CD32), and FcγRIII (CD16). Other Fc receptors, such as IgA receptors (e.g., FcαRI), also can be targeted. The Fc receptor is preferably located on the surface of an effector cell, e.g., a monocyte, macrophage or an activated mononuclear cell. In a preferred embodiment, the bispecific and multispecific molecules bind to an Fc receptor at a site which is distinct from the immunoglobulin Fc (e.g., IgG or IgA) binding site of the receptor. Therefore, the binding of the bispecific and multispecific molecules is not blocked by physiological levels of immunoglobulins.

In yet another aspect, anti-CLDN6 antibodies of the invention are derivatized, linked to or co-expressed with another functional molecule, e.g., another peptide or protein (e.g., a Fab' fragment). For example, an antibody of the invention can be functionally linked (e.g., by chemical coupling, genetic fusion, noncovalent association or otherwise) to one or more other molecular entities, such as another antibody (e.g. to produce a bispecific or a multispecific antibody), a cytotoxin, cellular ligand or antigen (e.g. to produce an immunoconjugate, such as an immunotoxin). An antibody of the present invention can be linked to other therapeutic moieties, e.g., a radioisotope, a small molecule anti-cancer drug, a recombinant cytokine or chemokine. Accordingly, the present invention encompasses a large variety of antibody conjugates, bispecific and multispecific molecules, and fusion proteins, all of which bind to CLDN6 expressing cells and/or to cells being characterized by association of CLDN6 with their cell surface and which can be used to target other molecules to such cells.

Generally, for the purposes of the present invention, all antibody derivatives such as antibody conjugates, bispecific and multispecific molecules, and fusion proteins described herein are encompassed by the term "antibody".

In a further aspect, the invention also envisions CLDN6-binding proteins derived from non-immunoglobulin domains, in particular single-chain proteins. Such binding proteins and methods for their production are described, for example, in Binz et al. (2005) Nature Biotechnology 23 (10): 1257-1268, herein incorporated by reference. It is to be understood that the teaching given herein with respect to immunoglobulin or immunoglobulin derived binding molecules correspondingly also applies to binding molecules derived from non-immunoglobulin domains. In particular, using such binding molecules derived from non-immunoglobulin domains it is possible to block CLDN6 of cells expressing said target and being characterized by association of said target with their cell surface and thus, to bring about therapeutic effects as disclosed herein for antibodies of the invention, in particular the inhibition of one or more activities of tumor cells as disclosed herein such as proliferation. Although not mandatory, it is possible to confer effector functions of antibodies to such non-immunoglobulin binding molecules by e.g. fusion to the Fc region of antibodies.

The present invention generally embraces the treatment and/or diagnosis of diseases, in particular tumor diseases, by targeting CLDN6 expressed by cells and being associated with the surface of cells. These methods provide for the selective detection and/or eradication of such cells thereby minimizing adverse effects to normal cells not expressing CLDN6 and not being characterized by association of CLDN6 with their cell surface. Preferred diseases for a therapy or diagnosis are those in which cells expressing CLDN6 and being characterized by association of CLDN6 with their cell surface are involved such as tumor diseases, in particular cancer diseases such as those described herein.

In one aspect, the invention provides compositions, e.g., pharmaceutical and diagnostic compositions/kits, comprising an antibody or a combination of antibodies of the invention. A pharmaceutical composition of the invention may comprise a pharmaceutically acceptable carrier and may optionally comprise one or more adjuvants, stabilizers etc. In a particular embodiment, the composition includes a combination of antibodies which bind to distinct epitopes or which possess distinct functional characteristics, such as inducing CDC and/or ADCC and inducing apoptosis. In this embodiment of the invention, antibodies may be used in combination, e. g., as a pharmaceutical composition comprising two or more anti-CLDN6 monoclonal antibodies. For example, anti-CLDN6 antibodies having different but complementary activities can be combined in a single therapy to achieve a desired therapeutic effect. In a preferred embodiment, the composition includes an anti-CLDN6 antibody that mediates CDC combined with another anti-CLDN6 antibody that induces apoptosis. In another embodiment, the composition includes an anti-CLDN6 antibody that mediates highly effective killing of target cells in the presence of effector cells, combined with another anti-CLDN6 antibody that inhibits the growth of cells expressing CLDN6 and being characterized by association of CLDN6 with their cell surface.

The present invention also includes the simultaneous or sequential administration of two or more anti-CLDN6 antibodies of the invention, wherein preferably at least one of said antibodies is a chimeric anti-CLDN6 antibody and at least one further antibody is a human anti-CLDN6 antibody, the antibodies binding to the same or different epitopes of CLDN6. Preferably, a chimeric CLDN6 antibody of the invention is administered first followed by the administration of a human anti-CLDN6 antibody of the invention, wherein the human anti-CLDN6 antibody is preferably administered for an extended period of time, i.e. as maintenance therapy.

Antibodies, conjugates, bispecific/multispecific molecules and compositions of the present invention can be used in a variety of methods for inhibiting growth of cells expressing CLDN6 and being characterized by association of CLDN6 with their cell surface and/or selectively killing cells expressing CLDN6 and being characterized by association of CLDN6 with their cell surface by contacting the cells with an effective amount of the antibody, conjugate, bispecific/multispecific molecule or composition, such that the growth of the cell is inhibited and/or the cell is killed. In one embodiment, the method includes killing of the cell expressing CLDN6 and being characterized by association of CLDN6 with its cell surface, optionally in the presence of effector cells, for example, by CDC, apoptosis, ADCC, phagocytosis, or by a combination of two or more of these mechanisms. Cells expressing CLDN6 and being characterized by association of CLDN6 with their cell surface which can be inhibited or killed using the antibodies of the invention include cancer cells.

Antibodies, conjugates, and bispecific/multispecific molecules and compositions of the present invention can be used to treat and/or prevent a variety of diseases involving cells expressing CLDN6 and being characterized by association of CLDN6 with their cell surface by administering the antibodies to patients suffering from such diseases. Exemplary diseases that can be treated (e.g., ameliorated) or prevented include, but are not limited to, tumorigenic diseases. Examples of tumorigenic diseases, which can be treated and/or prevented, include cancer diseases such as ovarian cancer, in particular ovarian adenocarcinoma and ovarian teratocarcinoma, lung cancer, including small cell lung cancer (SCLC) and non-small cell lung cancer (NSCLC), in particular squamous cell lung carcinoma and adenocarcinoma, gastric cancer, breast cancer, hepatic cancer, pancreatic cancer, skin cancer, in particular basal cell carcinoma and squamous cell carcinoma, malignant melanoma, head and neck cancer, in particular malignant pleomorphic adenoma, sarcoma, in particular synovial sarcoma and carcinosarcoma, bile duct cancer, cancer of the urinary bladder, in particular transitional cell carcinoma and papillary carcinoma, kidney cancer, in particular renal cell carcinoma including clear cell renal cell carcinoma and papillary renal cell carcinoma, colon cancer, small bowel cancer, including cancer of the ileum, in particular small bowel adenocarcinoma and adenocarcinoma of the ileum, testicular embryonal carcinoma, placental choriocarcinoma, cervical cancer, testicular cancer, in particular testicular seminoma, testicular teratoma and embryonic testicular cancer, uterine cancer, a germ cell tumor such as a teratocarcinoma or an embryonal carcinoma, in particular a germ cell tumor of the testis, and the metastatic forms thereof.

In a further aspect the invention relates to a method of treating or preventing a disease or disorder involving cells expressing CLDN6 and being characterized by association of CLDN6 with their cell surface comprising administering to a subject the antibody, conjugate, bispecific/multispecific molecule or composition of the invention. Preferably the disease or disorder is a tumor-related disease and in particular embodiments is selected from the group consisting of ovarian cancer, in particular ovarian adenocarcinoma and ovarian teratocarcinoma, lung cancer, including small cell lung cancer (SCLC) and non-small cell lung cancer (NSCLC), in particular squamous cell lung carcinoma and adenocarcinoma, gastric cancer, breast cancer, hepatic cancer, pancreatic cancer, skin cancer, in particular basal cell carcinoma and squamous cell carcinoma, malignant melanoma, head and neck cancer, in particular malignant pleomorphic adenoma, sarcoma, in particular synovial sarcoma and carcinosarcoma, bile duct cancer, cancer of the urinary bladder, in particular transitional cell carcinoma and papillary carcinoma, kidney cancer, in particular renal cell carcinoma including clear cell renal cell carcinoma and papillary renal cell carcinoma, colon cancer, small bowel cancer, including cancer of the ileum, in particular small bowel adenocarcinoma and adenocarcinoma of the ileum, testicular embryonal carcinoma, placental choriocarcinoma, cervical cancer, testicular cancer, in particular testicular seminoma, testicular teratoma and embryonic testicular cancer, uterine cancer, a germ cell tumor such as a teratocarcinoma or an embryonal carcinoma, in particular a germ cell tumor of the testis, and the metastatic forms thereof. CLDN6 is preferably expressed on the surface of said cells.

The invention may involve the use of the agents and compositions described herein for a prophylactic and/or therapeutic treatment of tumor diseases, i.e. for treating a patient having a tumor disease or being at risk of developing a tumor disease. In one aspect, the invention provides methods for inhibiting tumor growth comprising the administration of one or more of the agents and compositions described herein.

Preferably, the agents and compositions described herein are administered in a way such that the therapeutically active substance is not delivered or not substantially delivered to a tissue or organ wherein the cells when the tissue or organ is free of tumors express CLDN6 and are characterized by association of CLDN6 with their cell surface such as placenta tissue or placenta. To this end, the agents and compositions described herein can be administered locally.

In one aspect, the invention provides an antibody as described herein for use in the methods of treatment described herein. In one embodiment, the invention provides a pharmaceutical composition as described herein for use in the methods of treatment described herein.

In a particular embodiment of the invention, the subject being administered the antibody is additionally treated with a chemotherapeutic agent, radiation, or an agent that modulates, e.g., enhances or inhibits, the expression or activity of an Fc receptor, e.g. an Fc-gamma receptor, such as a cytokine. Typical cytokines for administration during treatment include granulocyte colony-stimulating factor (G-CSF), granulocyte-macrophage colony-stimulating factor (GM-CSF), interferon-γ (IFN-γ), and tumor necrosis factor (TNF). Typical therapeutic agents include, among others, anti-neoplastic agents such as doxorubicin, cisplatin, taxotere, 5-fluoruracil, methotrexat, gemzitabin and cyclophosphamide.

In yet another aspect, the invention relates to an immunization strategy to immunize non-human animals such as mice with human CLDN6 or a peptide fragment thereof to obtain antibodies. Preferred peptides for immunization are those selected from the group consisting of SEQ ID NO: 6, SEQ ID NO: 7, SEQ ID NO: 14 and SEQ ID NO: 15, and immunologically equivalent peptides.

Wildtype as well as transgenic non-human animals can be immunized with a purified or enriched preparation of CLDN6 antigen or a peptide fragment thereof and/or nucleic acids and/or cells expressing CLDN6 or a peptide fragment thereof. Preferably, the transgenic non-human animal is capable of producing multiple isotypes of human monoclonal antibodies to CLDN6 (e.g., IgG, IgA and/or IgM) by undergoing V-D-J recombination and isotype switching. Isotype switching may occur by e.g., classical or non-classical isotype switching.

Accordingly, in yet another aspect, the invention provides isolated B cells from a non-human animal as described above. The isolated B cells can then be immortalized by fusion to an immortalized cell to provide a source (e.g., a hybridoma) of antibodies of the invention. Such hybridomas (i.e., which produce antibodies of the invention) are also included within the scope of the invention.

In a further aspect, the present invention relates to methods for diagnosis, detection or monitoring of a tumor disease comprising the detection of and/or determination of the quantity of CLDN6 or cells expressing CLDN6 and being characterized by association of CLDN6 with their cell surface in a biological sample isolated from a patient using an antibody of the invention. The biological sample may be isolated from a patient having a tumor disease, being suspected of having or falling ill with a tumor disease or having a potential for a tumor disease.

In one embodiment of the method for diagnosis, detection or monitoring of a tumor disease according to the invention, a biological sample and/or a control/reference sample is from a tissue or organ corresponding to the tissue or organ which is to be diagnosed, detected or monitored with respect to affection by a tumor disease, e.g. the tumor disease which is to be diagnosed, detected or monitored is ovarian cancer and the biological sample and/or control/reference sample is ovarian tissue. Such tissues and organs are described herein, for example, in connection with different tumor diseases and cancers.

In one embodiment of the methods for diagnosis, detection or monitoring of a tumor disease the biological sample is from a tissue or organ wherein the cells when the tissue or organ is free of tumors do not substantially express CLDN6 and are not characterized by substantial association of CLDN6 with their cell surface. Preferably said tissue is a tissue other than placenta tissue.

Typically, the level of a target molecule in a biological sample is compared to a reference level, wherein a deviation from said reference level is indicative of the presence and/or stage of a tumor disease in a subject. The reference level may be a level as determined in a control sample (e.g., from a healthy tissue or subject) or a median level from healthy subjects. A "deviation" from said reference level designates any significant change, such as an increase or decrease by at least 10%, 20%, or 30%, preferably by at least 40% or 50%, or even more. Preferably, the presence of CLDN6 or cells expressing CLDN6 and being characterized by association of CLDN6 with their cell surface in said biological sample or a quantity of CLDN6 or cells expressing CLDN6 and being characterized by association of CLDN6 with their cell surface in the biological sample which is increased compared to a reference level indicates the presence of a tumor disease.

Typically, the detection and/or determination of the quantity in the methods of the invention involves the use of labeled antibodies which specifically bind to a target molecule.

In a particular aspect, the invention relates to a method for detection, i.e. determining the position or site, of a tumor disease, e.g. a particular tissue or organ, which comprises administering an antibody of the present invention which is coupled to a detectable label to a patient. Labelling of a tissue or organ in said patient may indicate the presence of or risk for a tumor disease in said tissue or organ.

As exemplified herein, antibodies of the invention can be obtained directly from hybridomas which express the antibody, or can be cloned and recombinantly expressed in a host cell (e.g., a CHO cell, or a lymphocytic cell). Further examples of host cells are microorganisms, such as *E. coli*, and fungi, such as yeast. Alternatively, they can be produced recombinantly in a transgenic non-human animal or plant. However, the present invention also envisions embodiments wherein the antibodies are produced by immunization or vaccination using immunization strategies as disclosed herein in situ in a patient.

The present invention also relates to nucleic acids comprising genes or nucleic acid sequences encoding antibodies or parts thereof, e.g. an antibody chain, as described herein. The nucleic acids may be comprised in a vector, e.g., a plasmid, cosmid, virus, bacteriophage or another vector used e.g. conventionally in genetic engineering. The vector may comprise further genes such as marker genes which allow for the selection of the vector in a suitable host cell and under suitable conditions. Furthermore, the vector may comprise expression control elements allowing proper expression of the coding regions in suitable hosts. Such control elements are known to the artisan and may include a promoter, a splice cassette, and a translation initiation codon.

Preferably, the nucleic acid of the invention is operatively attached to the above expression control sequences allowing expression in eukaryotic or prokaryotic cells. Control elements ensuring expression in eukaryotic or prokaryotic cells are well known to those skilled in the art.

Methods for construction of nucleic acid molecules according to the present invention, for construction of vectors comprising the above nucleic acid molecules, for introduction of the vectors into appropriately chosen host cells, for causing or achieving the expression are well-known in the art.

A further aspect of the present invention relates to a host cell comprising a nucleic acid or vector as disclosed herein.

Other features and advantages of the instant invention will be apparent from the following detailed description and claims.

BRIEF DESCRIPTION OF THE DRAWINGS

FIG. 1 shows sequence alignment of CLDN3, CLDN4, CLDN6 and CLDN9.

FIG. 2A. Unfixed CHO-K1 cells co-transfected with nucleic acids encoding human CLDN6 and GFP, respectively, were probed with an anti-CLDN6 monoclonal mouse antibody (R&D Systems, MAB3656). CLDN6 is located at the plasma membrane of transfected cells and can be targeted on living cells by specific antibodies.

FIG. 2B. Serum from a mouse on the basis of which the hybridoma F3-6C3-H8 was produced contained antibodies binding to CLDN6 on the surface of unfixed CHO-K1 cells co-transfected with nucleic acids encoding human CLDN6 and GFP.

Protein lysates of HEK293T cells transfected with nucleic acids encoding CLDN3, CLDN4, CLDN6, and CLDN9, respectively, or mock-transfected were tested by Western blotting using commercially available anti-CLDN3(A) (Invitrogen, Cat No. 34-1700), anti-CLDN4(A) (Zymed, 32-9400), anti-CLDN6(A) (ARP, 01-8865) and anti-CLDN9 (A) (Santa Cruz, sc-17672) antibodies. The antibodies detected expression of their corresponding targets only in the respective HEK293T transfectants. No endogenous expression of any of these claudins was observed in non-transfected HEK293T cells.

Figure 4:
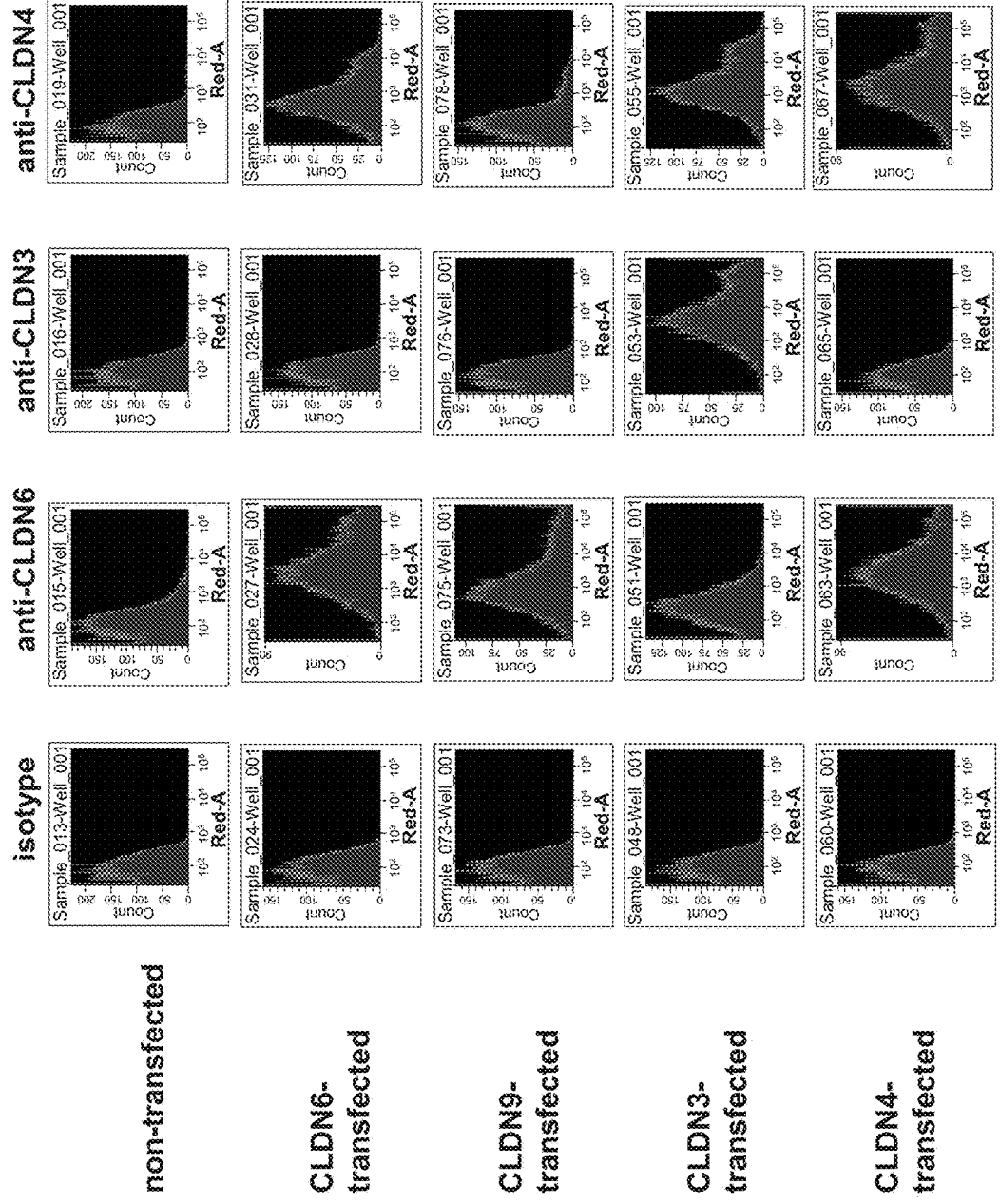

FIG. 4 shows flow cytometry analysis for assaying the specificity of commercially available anti-CLDN antibodies.

Binding of commercially available anti-CLDN antibodies to HEK293T cells transfected with nucleic acids encoding CLDN3, CLDN4, CLDN6, and CLDN9, respectively, or non-transfected was determined by flow cytometry. Only the commercially available anti-CLDN3 antibody is specific for its target.

Figure 5B:
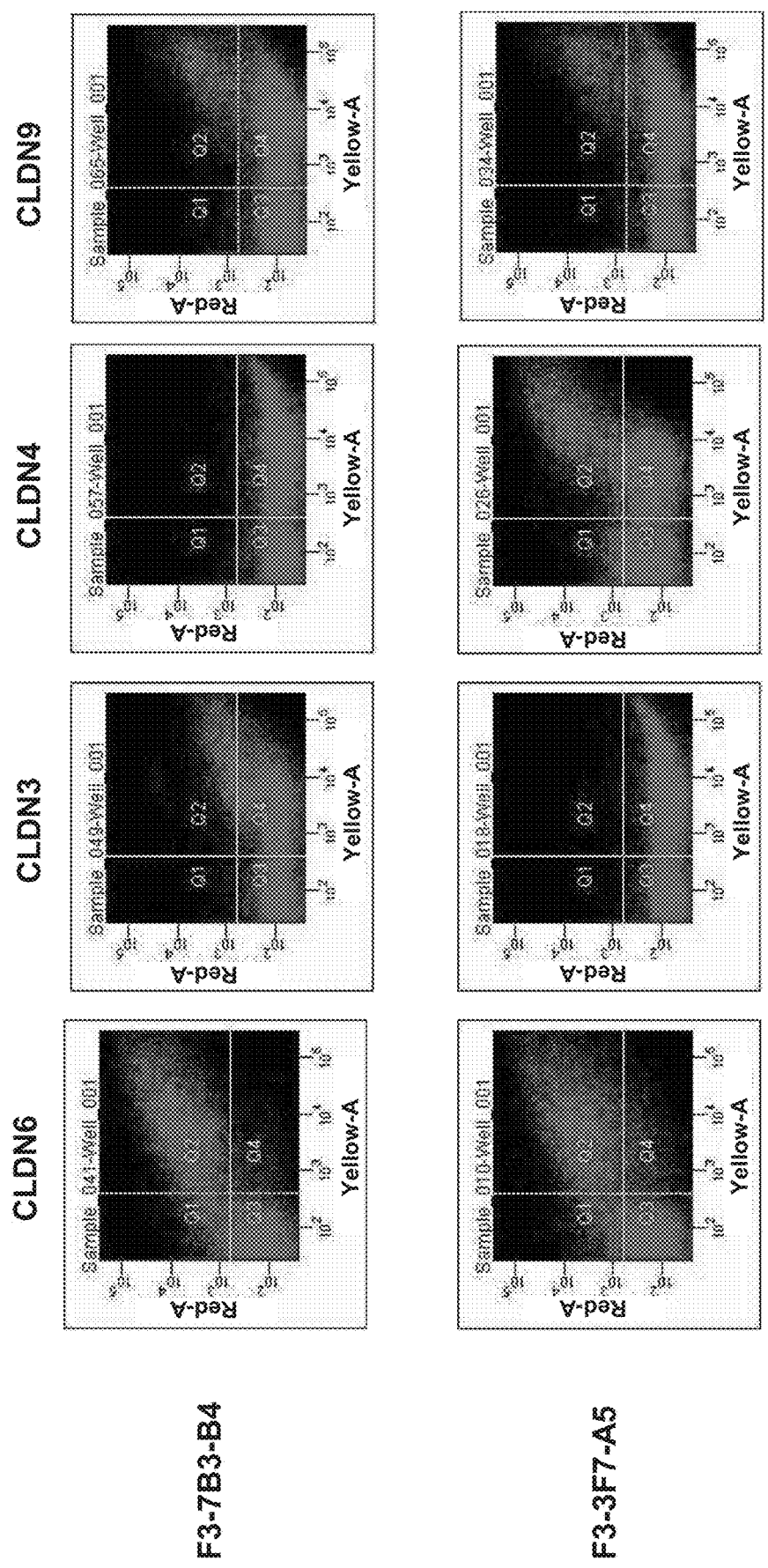

FIG. 5A and FIG. 5B show flow cytometry analysis for assaying the specificity of anti-CLDN antibodies prepared according to the invention.

Binding of antibodies in supernatants from monoclonal hybridoma subclones to HEK293T cells co-transfected with a vector encoding CLDN6, CLDN3, CLDN4 or CLDN9 and a vector encoding a fluorescence marker was determined by flow cytometry.

FIG. 5A. Antibodies in the supernatant from the monoclonal hybridoma subclone F3-6C3-H8 specifically bind to CLDN6 transfected cells but not to cells transfected with CLDN3, CLDN4 and CLDN9, respectively. In contrast, antibodies in the supernatant from the monoclonal hybridoma subclone F4-4F7-F2 bind to cells transfected with CLDN6 or CLDN9. Antibodies in the supernatant from the monoclonal hybridoma subclone F3-6C3-H8 also bind to cells transfected with the (I143V)-SNP variant of CLDN6.

FIG. 5B. Antibodies in the supernatant from the monoclonal hybridoma subclone F3-7B3-B4 bind to cells transfected with CLDN6, CLDN3 or CLDN9. Antibodies in the supernatant from the monoclonal hybridoma subclone F3-3F7-A5 bind to cells transfected with CLDN6, CLDN4 or CLDN9.

Figure 6:
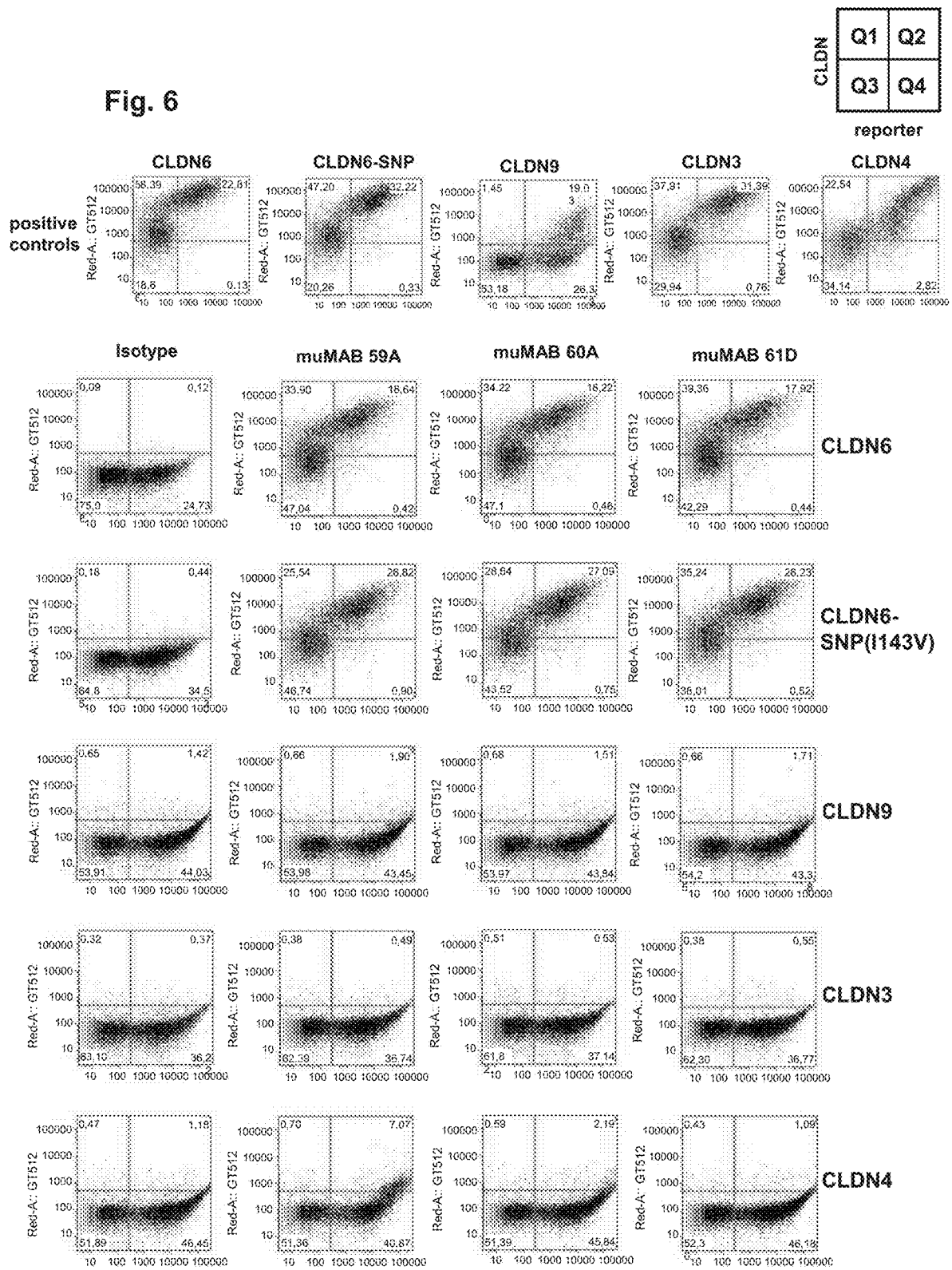
Figure 6:
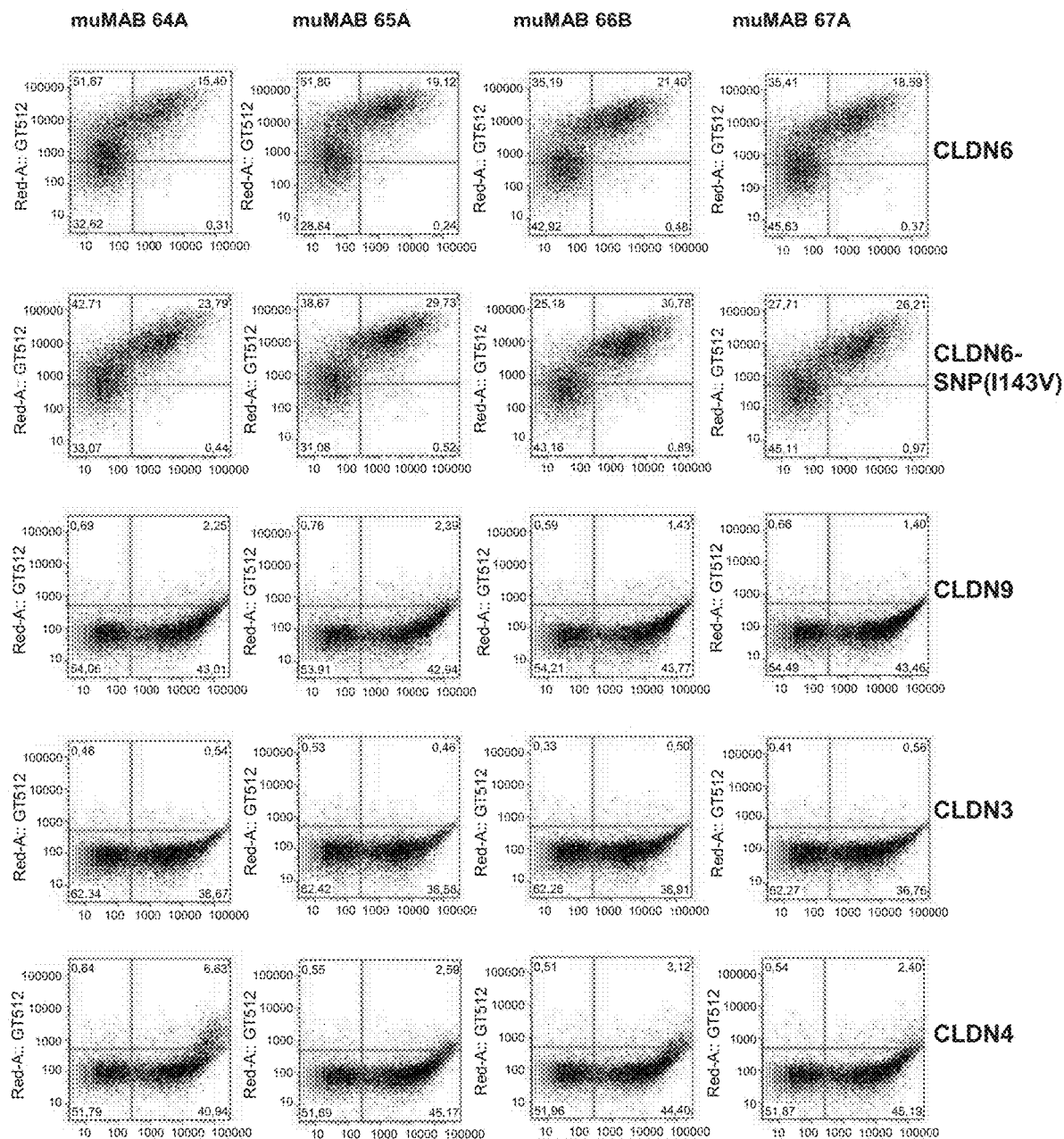

FIG. 6 shows binding specificity of anti-CLDN6 murine monoclonlal antibodies muMAB 59A, 60A, 61D, 64A, 65A, 66B and 67A.

The binding of anti-CLDN6 antibodies to human CLDN6, 3, 4, 9 and the CLDN6 SNP (single nucleotide polymorphism) variant I143V was analyzed by flow cytometry using HEK293T cells transiently expressing the corresponding human claudin. HEK293T were co-transfected with a fluorescence marker to distinguish between non-transfected (Q1 and Q3 population) and transfected (Q2 and Q4 population) cells. The antibody concentration used was the concentration that saturated binding to CLDN6 (25 µg/ml). The expression of human CLDN6, 3, 4, 9 and CLDN6-SNP (I143V) was confirmed with commercially available monoclonal antibodies against human Claudin-6 (R&D Systems, MAB3656), human Claudin-3 (R&D Systems, MAB4620) and human Claudin-4 (R&D Systems, MAB 4219).

Figure 7:
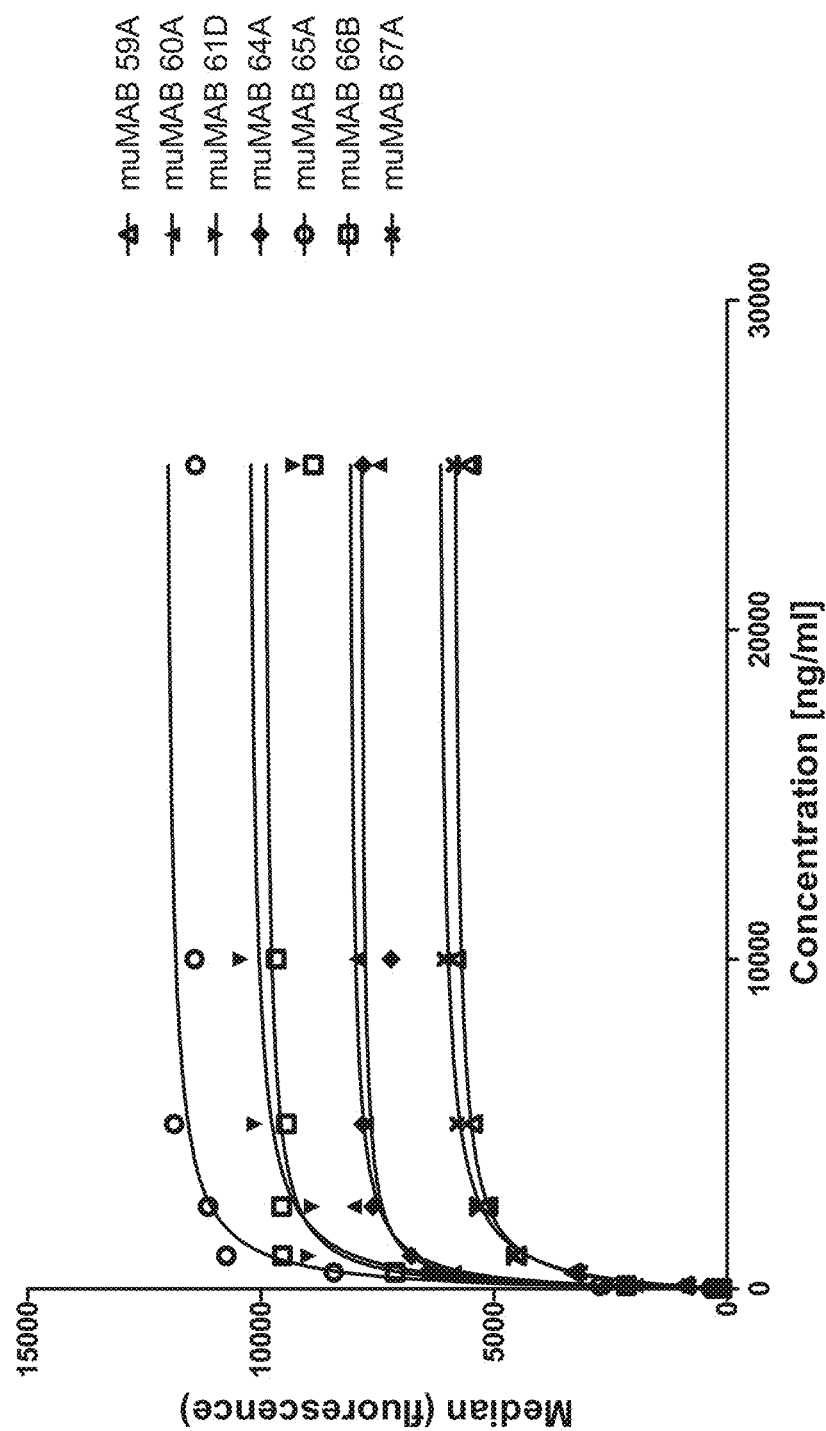

FIG. 7 shows relative affinities of anti-CLDN6 murine monoclonal antibodies muMAB 59A, 60A, 61D, 64A, 65A, 66B and 67A.

To determine relative affinities the binding of anti-CLDN6 antibodies to human CLDN6 stably expressed on the surface of HEK293 cells was analyzed by flow cytometry. In the saturation binding experiment the concentration of the antibodies was plotted against the FACS signals (median of fluorescence intensity). The EC50 (antibody concentration that binds to half the binding sites at equilibrium) was calculated by nonlinear regression. The CLDN6-specific antibodies muMAB 59A, 60A, 61D, 64A, 65A, 66B and 67A exhibited very low EC50 values (EC50 200-500 ng/ml) and saturation of binding was achieved at low concentrations.

Figure 8:
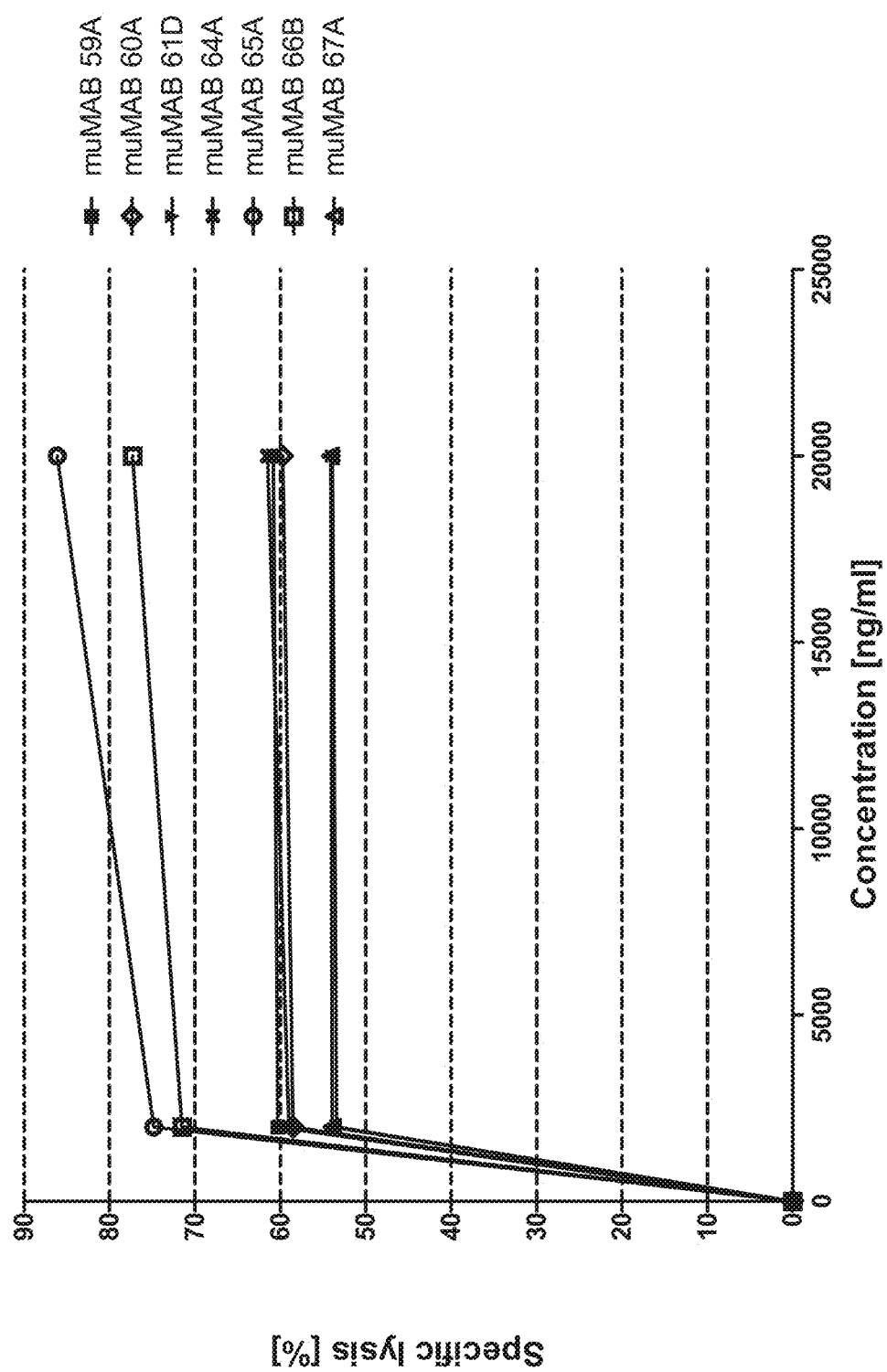

FIG. 8 shows complement-dependent cytotoxicity (CDC) activity of anti-CLDN6 murine monoclonal antibody muMAB 59A, 60A, 61D, 64A, 65A, 66B and 67A.

The CDC activity of anti-CLDN6 antibodies was analyzed using a luciferase-dependent assay to detect endogenous ATP within non-lysed cells. Therefore, CHO-K1 cells stably expressing human CLDN6 were treated with different concentrations of muMAB 59A, 60A, 61D, 64A, 65A, 66B and 67A. MuMAB 59A, 60A, 61D, 64A, 65A, 66B and 67A exhibited dose-dependent CDC activity and induced CDC at low concentrations.

Figure 9:
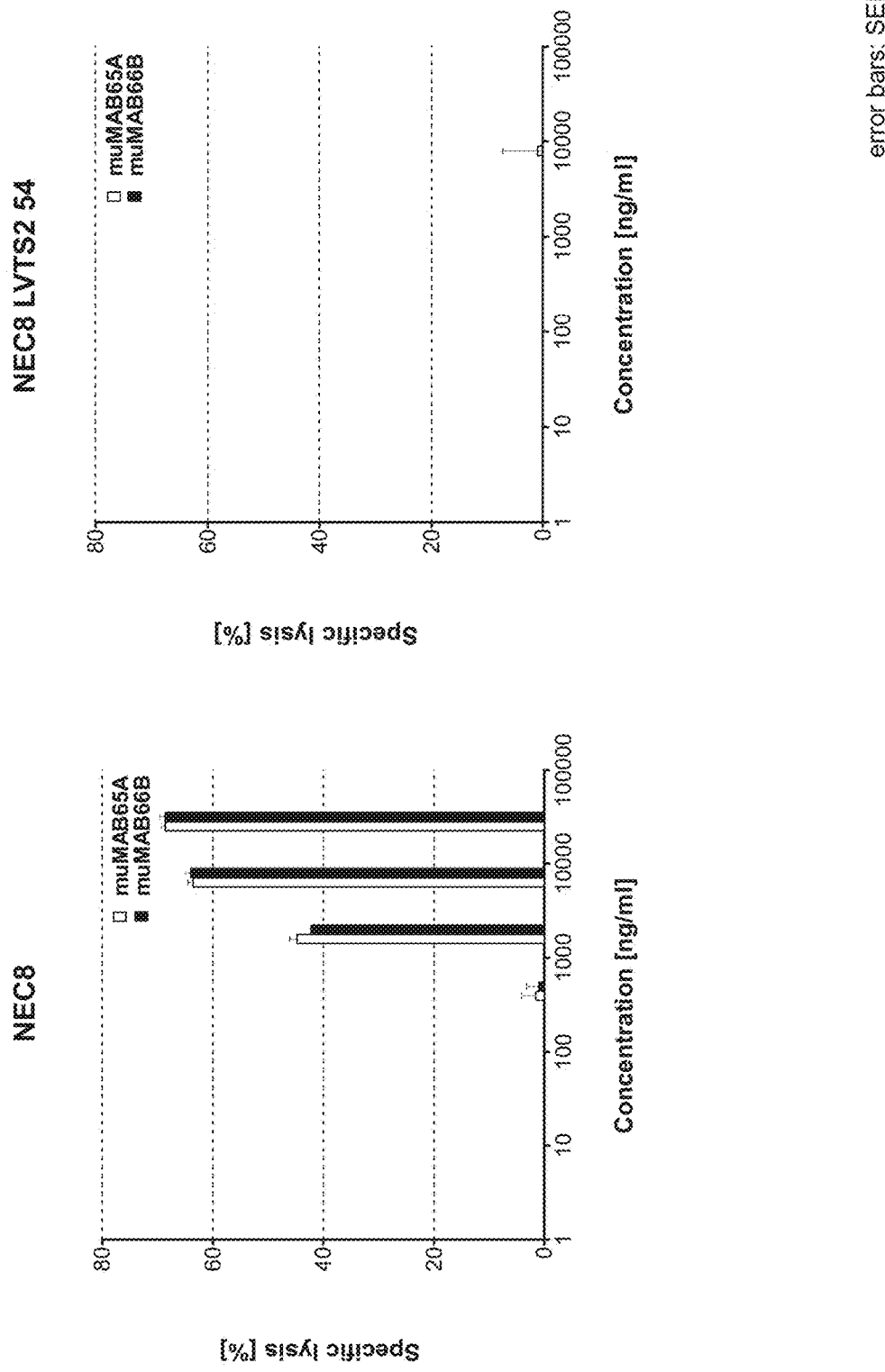

FIG. 9 shows complement-dependent cytotoxicity (CDC) activity of anti-CLDN6 murine monoclonal antibodies muMAB 65A and 66B on endogenously CLDN6 expressing NEC8 and NEC8 LVTS2 54 (CLDN6 knock-down) cells.

The anti-CLDN6 antibodies muMAB 65A and 66B induced CDC on NEC8 cells in a dose dependent manner. Target specificity of muMAB 65A and 66B was proved by using NEC8 LVTS2 54 cells (CLDN6 knock-down).

Figure 10:
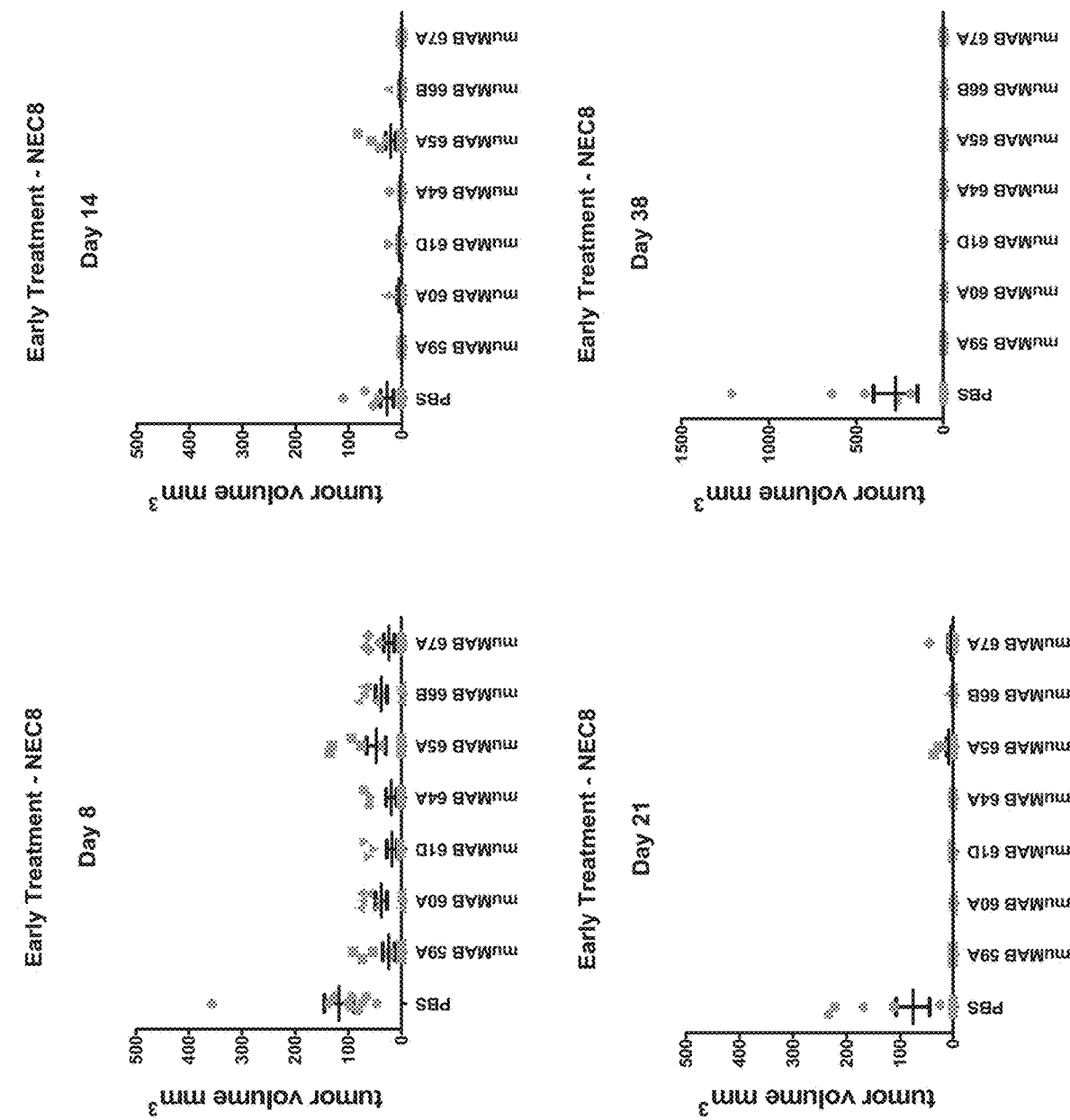

FIG. 10 shows therapeutic effect of muMAB 59A, 60A, 61D, 64A, 65A, 66B and 67A in an early treatment xenograft model using mice engrafted with the tumor cell line NEC8.

The model used endogenously CLDN6 expressing NEC8 xenografts in athymic Nude-Foxn1$^{nu}$ mice. Compared to the saline control group muMAB 59A, 60A, 61D, 64A, 65A, 66B and 67A showed tumor growth inhibition in mice engrafted with NEC8 cells.

Figure 11:
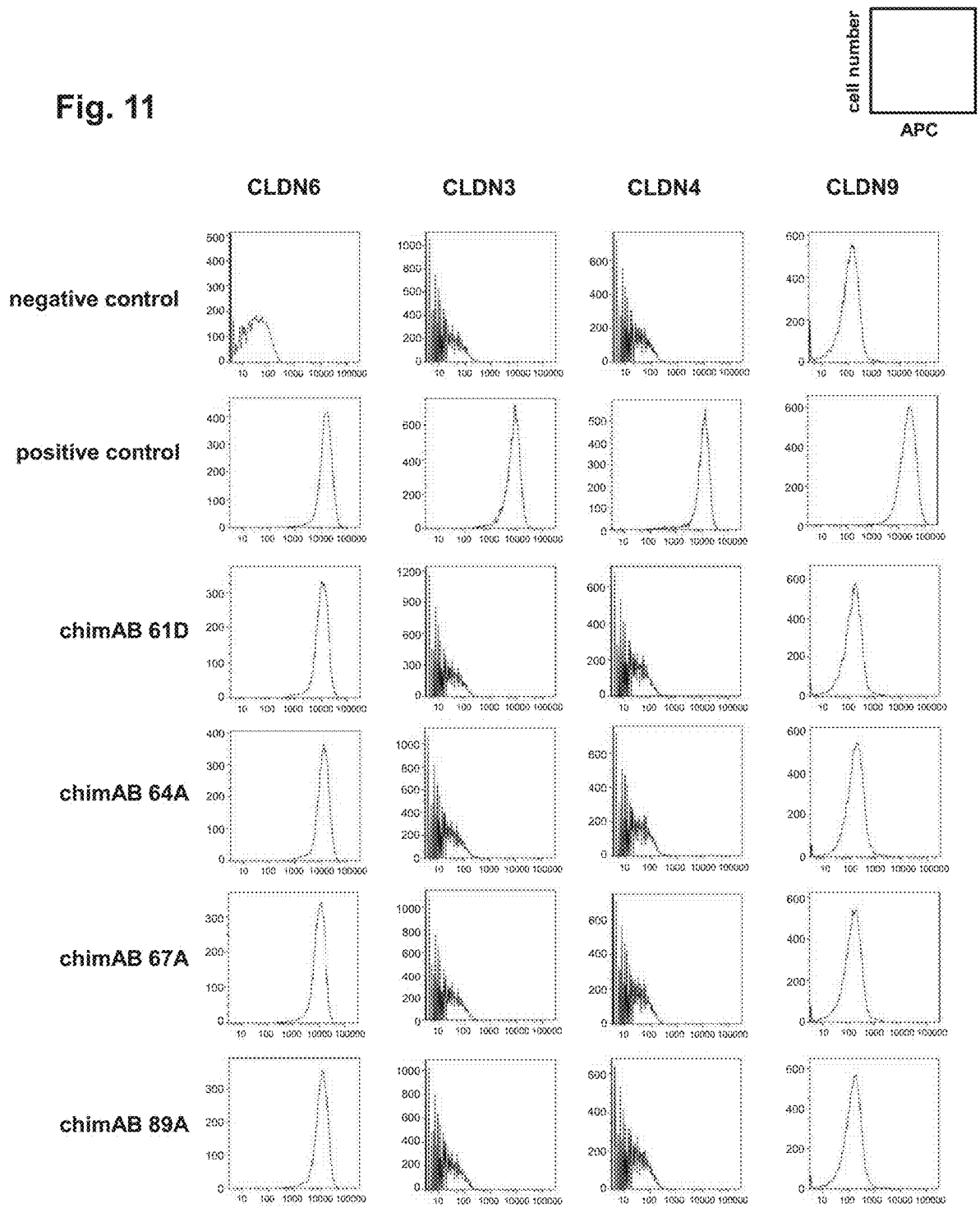

FIG. 11 shows binding specificity of anti-CLDN6 chimeric monoclonal antibodies chimAB 61D, 64A, 67A and 89A.

The binding of anti-CLDN6 antibodies to human CLDN6, 3, 4 and 9, respectively, was analyzed by flow cytometry using HEK293 cells stably expressing the corresponding human claudin. The antibody concentration used was the concentration that saturated binding (25 µg/ml). The expression of human CLDN3, 4, 6 and 9 was confirmed with commercially available monoclonal antibodies against human Claudin-3 (R&D Systems, MAB4620) and human Claudin-4 (R&D Systems, MAB 4219), and the CLDN6/9-reactive murine monoclonal antibody muMAB 5F2D2, respectively. The negative control was carried out under identical conditions without primary antibody.

Figure 12:
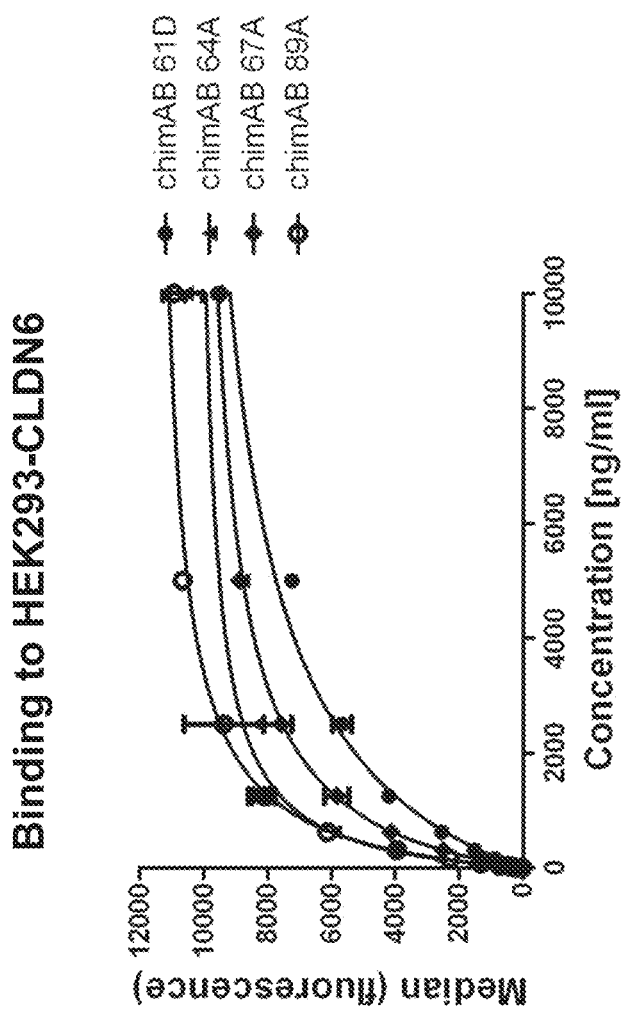

FIG. 12 shows relative affinities of anti-CLDN6 chimeric monoclonal antibodies chimAB 61D, 64A, 67A and 89A to 11EK293-CLDN6 cells.

To determine relative affinities the binding of anti-CLDN6 antibodies to human CLDN6 stably expressed on the surface of HEK293 cells was analyzed by flow cytometry. In the saturation binding experiment the concentration of the antibodies was plotted against the FACS signals (median of fluorescence intensity). The EC50 (antibody concentration that binds to half the binding sites at equilibrium) was calculated by nonlinear regression. The CLDN6-specific antibodies chimAB 64A and 89A exhibited very low EC50 values (EC50 450-600 ng/ml) and saturation of binding was achieved at low concentrations. ChimAB 67A and 61D showed low (EC50 1000 ng/ml) and medium (EC50 2300 ng/ml) EC50 values, respectively.

Figure 13:
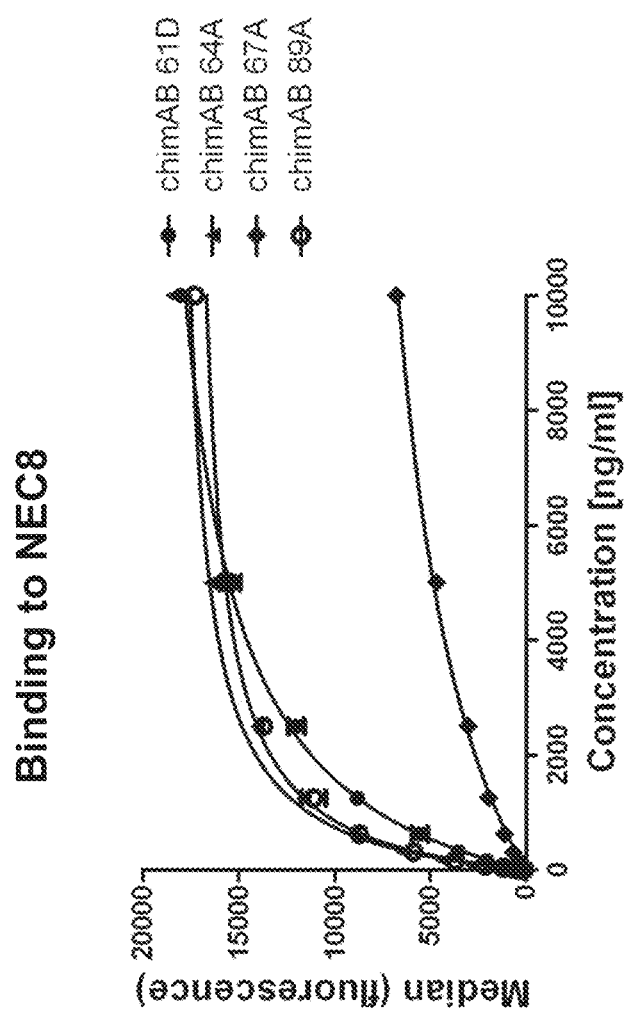

FIG. 13 shows relative affinities of anti-CLDN6 chimeric monoclonal antibodies chimAB 61D, 64A, 67A and 89A to NEC8 cells.

To determine the binding affinities of anti-CLDN6 antibodies to tumor cells that endogenously express human CLDN6 binding to the testicular cancer cell line NEC8 was analyzed by flow cytometry. The CLDN6-specific antibodies chimAB 64A and 89A exhibited very low EC50 values (EC50 600-650 ng/ml) and saturation of binding was achieved at low concentrations, whereas chimAB 61D and 67A showed medium (EC50 1700 ng/ml) and high (EC50 6100 ng/ml) EC50 values, respectively.

Figure 14:
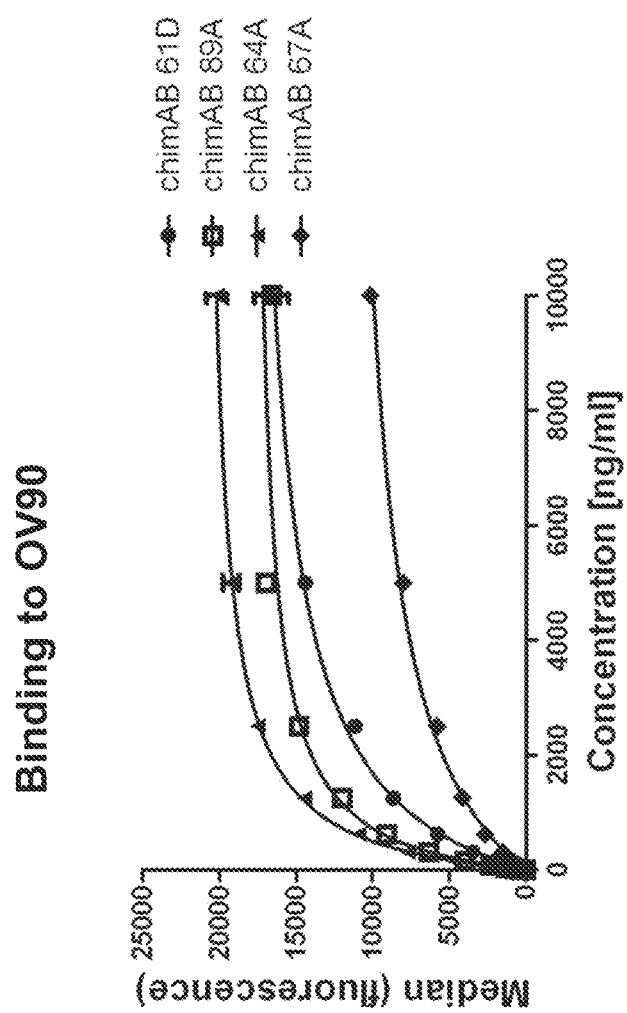

FIG. 14 shows relative affinities of anti-CLDN6 chimeric monoclonal antibodies chimAB 61D, 64A, 67A and 89A to OV90 cells.

To determine the binding affinities of anti-CLDN6 antibodies to tumor cells that endogenously express human CLDN6 binding to the ovarian cancer cell line OV90 was analyzed by flow cytometry. The CLDN6-specific antibodies chimAB 64A and 89A exhibited very low EC50 values (EC50 550-600 ng/ml) and saturation of binding was achieved at low concentrations. ChimAB 61D and 67A showed medium EC50 values (EC50 1500 ng/ml and EC50 2300 ng/ml, respectively).

Figure 15:
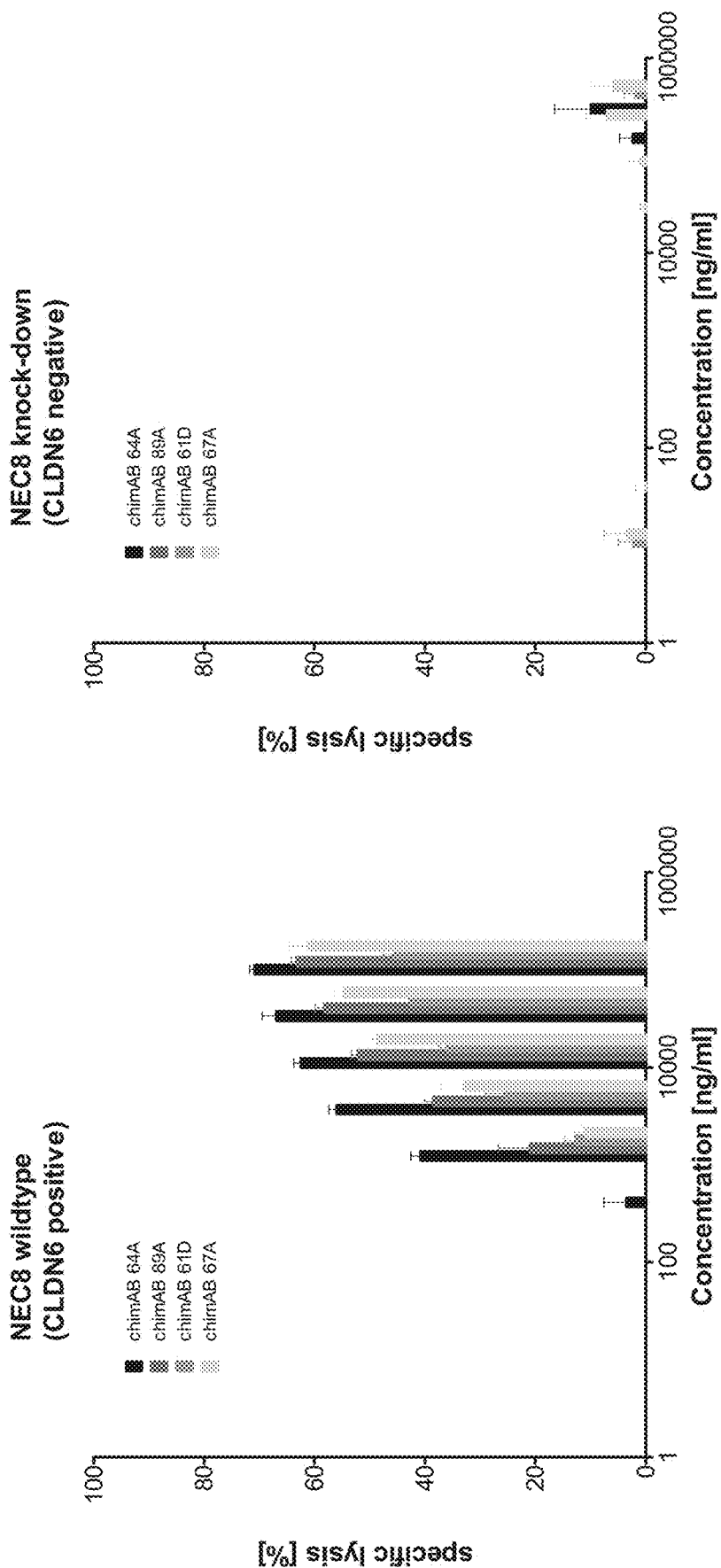

FIG. 15 shows complement-dependent cytotoxicity (CDC) activity of anti-CLDN6 chimeric monoclonal antibodies chimAB 61D, 64A, 67A and 89A on NEC8 wildtype and NEC8 knock-down cells.

The CDC activity of anti-CLDN6 antibodies was analyzed using a luciferase-dependent assay to detect endogenous ATP within non-lysed cells. Therefore, NEC8 wildtype cells (NEC8 LVTS2 77) ectopically expressing luciferase were treated with different concentrations of chimAB 61D, 64A, 67A and 89A. On NEC-8 cells chimAB 61D, 64A, 67A and 89A exhibited CDC activity in a dose-dependent manner, whereas on NEC-8 CLDN6 knock-down cells (NEC8 LVTS2 54) none of these antibodies induced unspecific cell lysis. This result demonstrated target specific effector functions of chimAB 61D, 64A, 67A and 89A.

Figure 16:
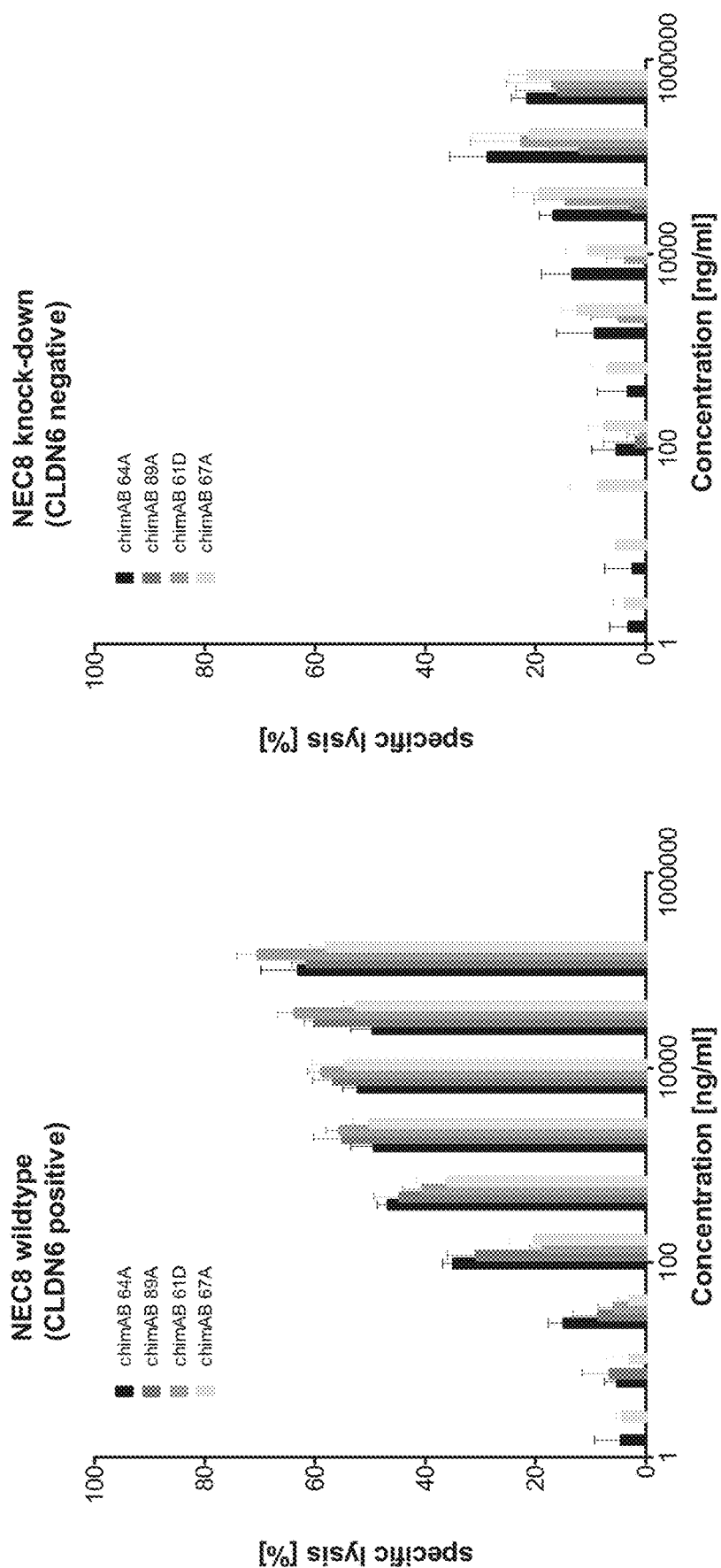

FIG. 16 shows antibody-dependent cellular cytotoxicity (ADCC) activity of anti-CLDN6 chimeric monoclonal antibodies chimAB 61D, 64A, 67A and 89A on NEC8 wildtype and NEC8 knock-down cells.

The ADCC activity of anti-CLDN6 antibodies was analyzed using a luciferase-dependent assay to detect endogenous ATP within non-lysed cells. Therefore, NEC-8 wildtype cells (NEC8 LVTS2 77) were treated with different concentrations of chimAB 61D, 64A, 67A and 89A. ChimAB 61D, 64A, 67A and 89A exhibited dose-dependent ADCC activity and induced ADCC even at low antibody concentrations. To demonstrate target specificity NEC8 cells with a stable CLDN6 knock-down (NEC8 LVTS2 54) were used.

Figure 17:
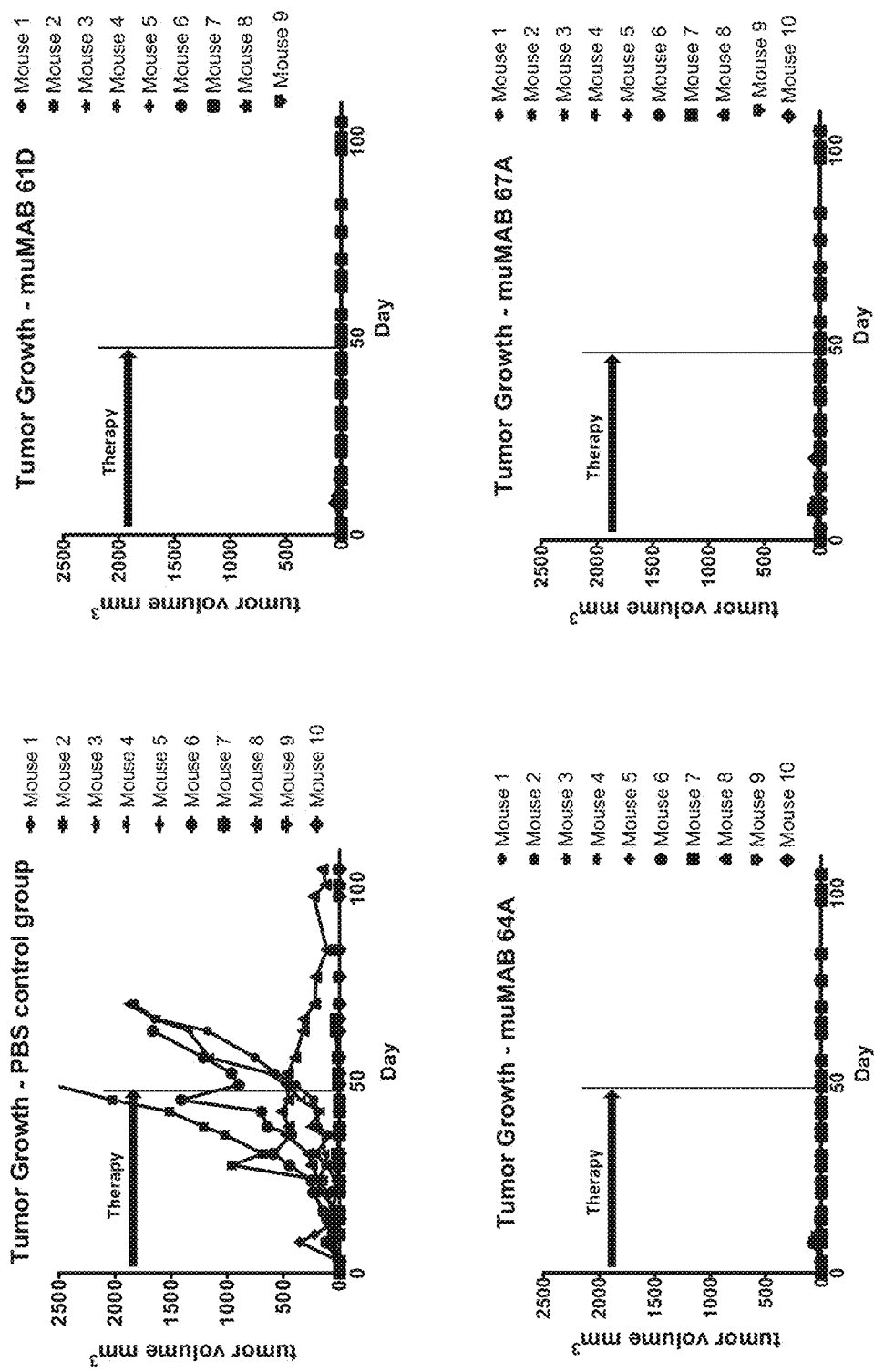

FIG. 17 shows therapeutic long term effect of anti-CLDN6 murine monoclonal antibodies muMAB 61D, 64A and 67A in an early treatment xenograft model using mice engrafted with the tumor cell line NEC8.

The model used endogenously CLDN6 expressing NEC8 xenografts in athymic Nude-Foxn1$^{nu}$ mice. Mice were treated for 46 days with CLDN6 specific antibodies. After treatment, the tumor growth was monitored for 60 days. Even after stopping the immunotherapy mice treated with murine monoclonal antibodies muMAB 61D, 64A and 67A did not show any tumor growth.

Figure 18A:
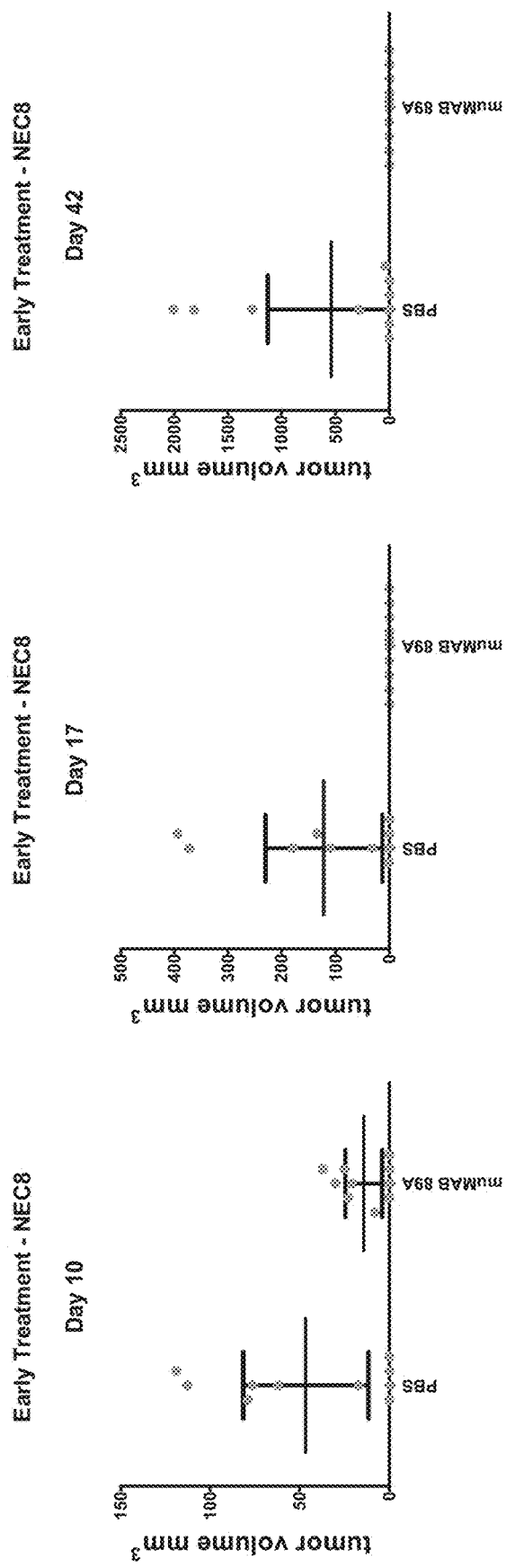
Figure 18B:
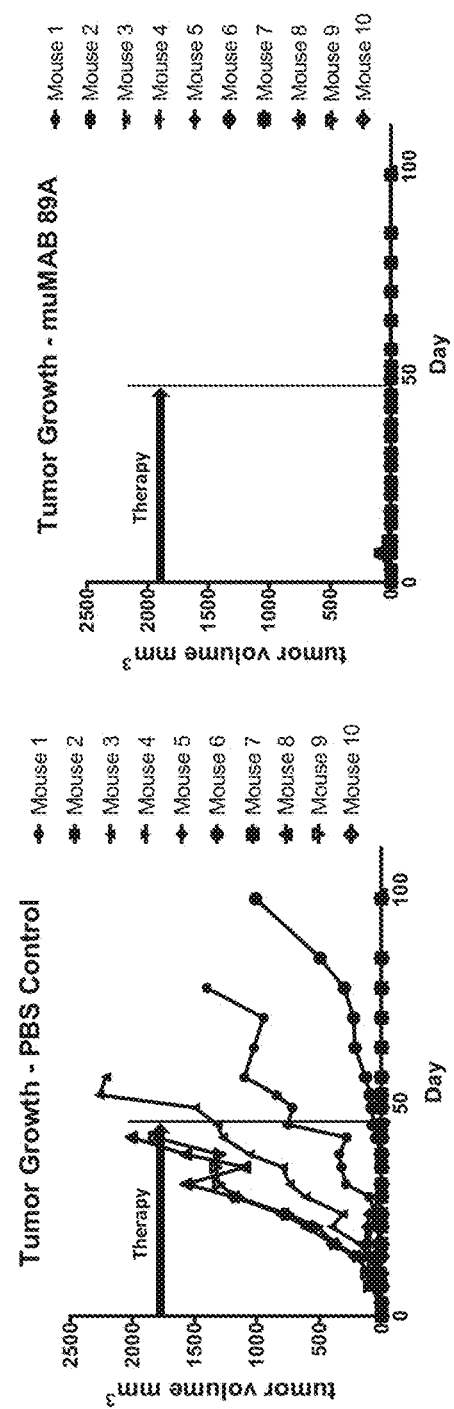

FIG. 18A and FIG. 18B show therapeutic effect of the anti-CLDN6 murine monoclonal antibody muMAB 89A in an early treatment xenograft model using mice engrafted with the tumor cell line NEC8.

The model used endogenously CLDN6 expressing NEC8 xenografts in athymic Nude-Foxn1$^{nu}$ mice. Scatter blots represent volumes of engrafted tumors at different time points during early treatment of NEC8 xenografts in athymic Nude-Foxn1$^{nu}$ mice. Compared to the saline control group muMAB 89A showed tumor growth inhibition in mice engrafted with NEC8 cells (FIG. 18A). Mice were treated for 47 days with PBS as a control and the CLDN6 specific antibody, respectively. The tumor growth was monitored for additional 51 days. Compared to the PBS control there were no tumors detectable in mice treated with muMAB89A at the end of the study (FIG. 18B).

Figure 19:
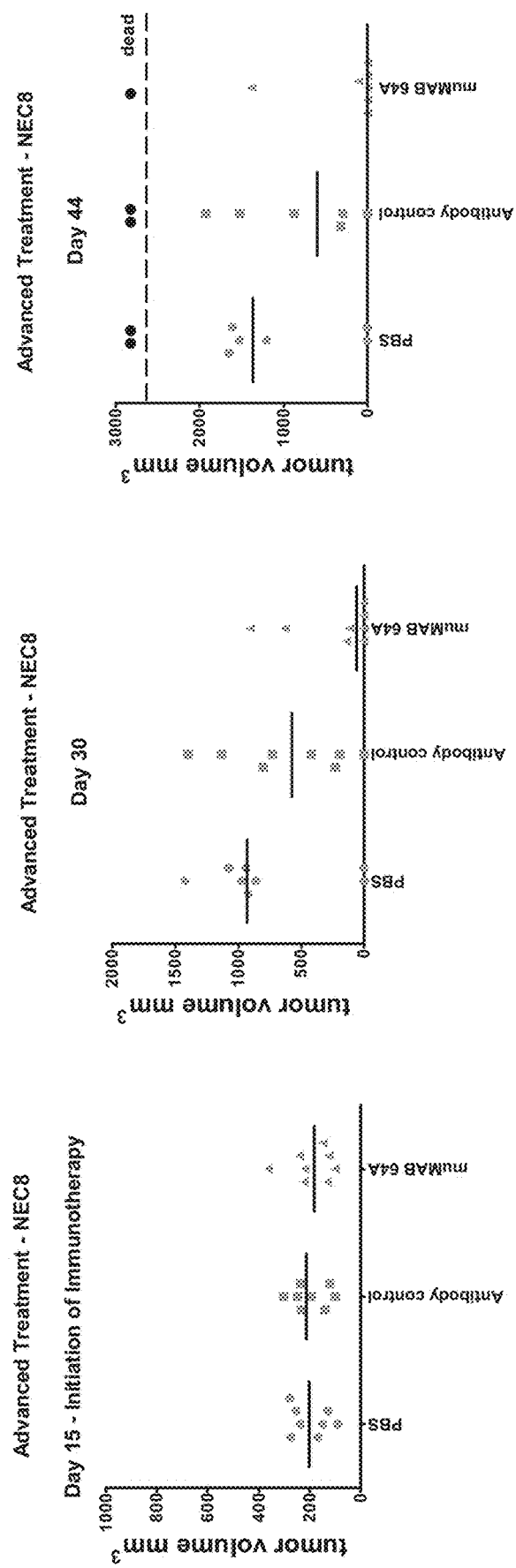

FIG. 19 shows therapeutic effect of the anti-CLDN6 murine monoclonal antibody muMAB 64A in an advanced treatment xenograft model using mice engrafted with the tumor cell line NEC8.

Scatter blots represent volumes of engrafted tumors at different time points during treatment of advanced NEC8 xenografts in athymic Nude-Foxn1$^{nu}$ mice. Immunotherapy with the murine monoclonal anti-CLDN6 antibody muMAB 64A showed an inhibition of tumor growth of solid NEC8 xenografts compared to both the antibody and saline control groups.

FIG. 20A and FIG. 20B show therapeutic long term effect of the anti-CLDN6 murine monoclonal antibody muMAB 64A in an advanced treatment xenograft model using mice engrafted with the tumor cell line NEC8.

15 days after engraftment mice were treated for 45 days with the CLDN6 specific antibody muMAB 64A. The tumor growth was monitored for additional 49 days (FIG. 20A). The survival plot showed prolonged survival of mice treated with the CLDN6 specific antibody muMAB 64A (FIG. 20B).

Figure 21:
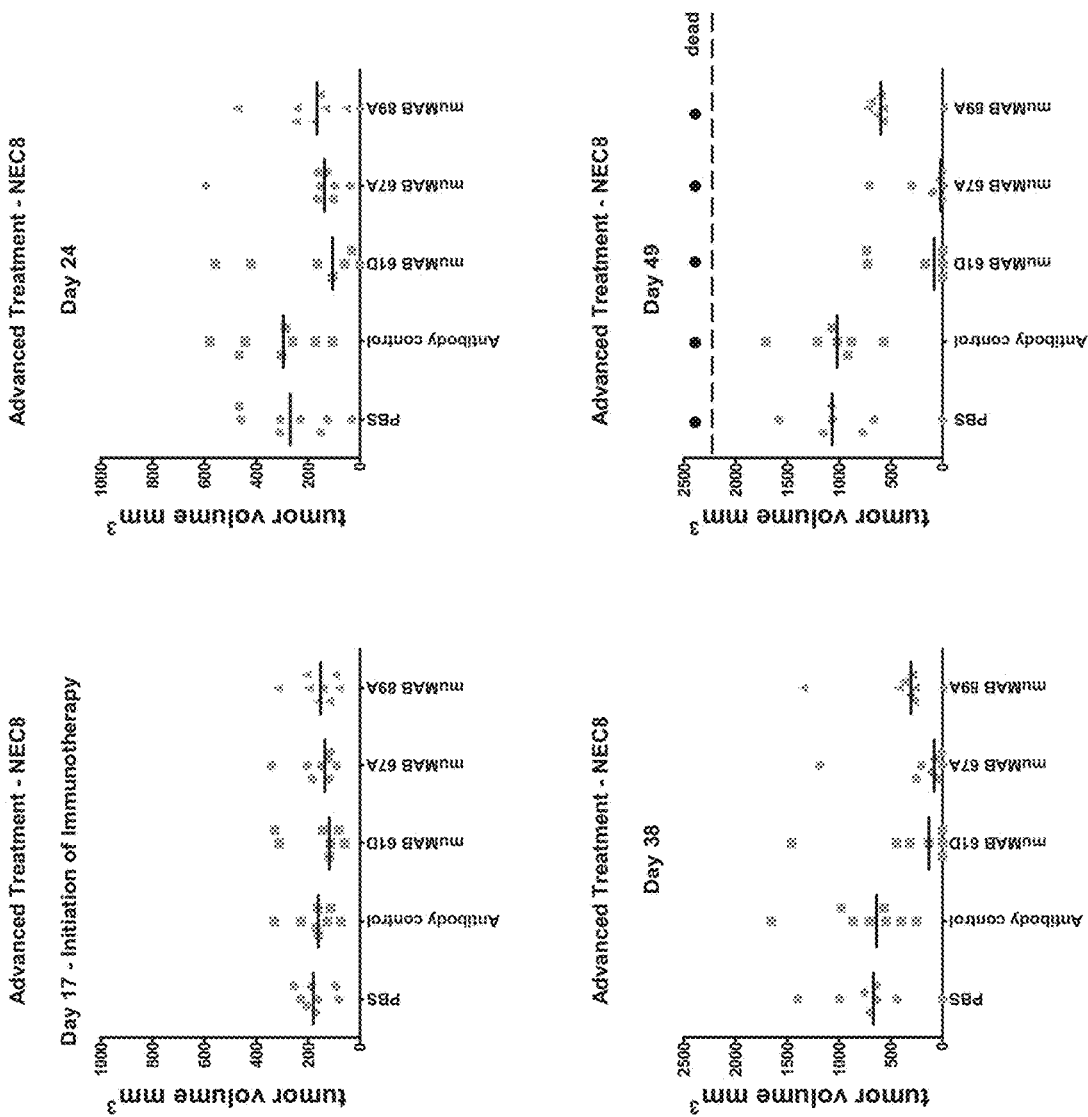

FIG. 21 shows therapeutic effect of anti-CLDN6 murine monoclonal antibodies muMAB 61D, 67A and 89A in an advanced treatment xenograft model using mice engrafted with the tumor cell line NEC8.

Scatter blots represent volumes of engrafted NEC8 tumors at different time points during treatment of advanced NEC8 xenografts. Compared to the saline and antibody control groups the inhibition of tumor growth was achieved with the murine monoclonal anti-CLDN6 antibodies muMAB 61D, 67A and 89A.

Figure 22A:
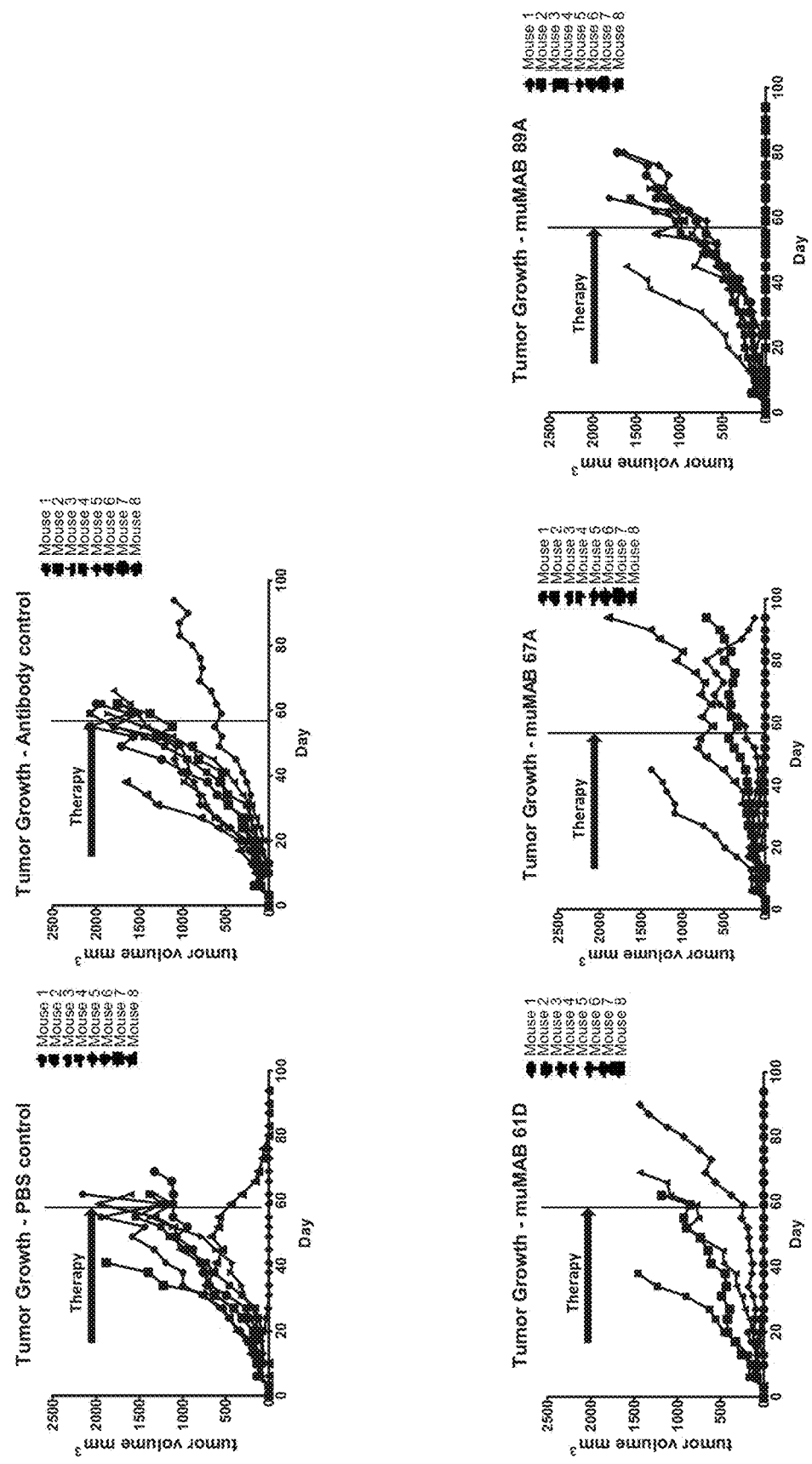
Figure 22B:
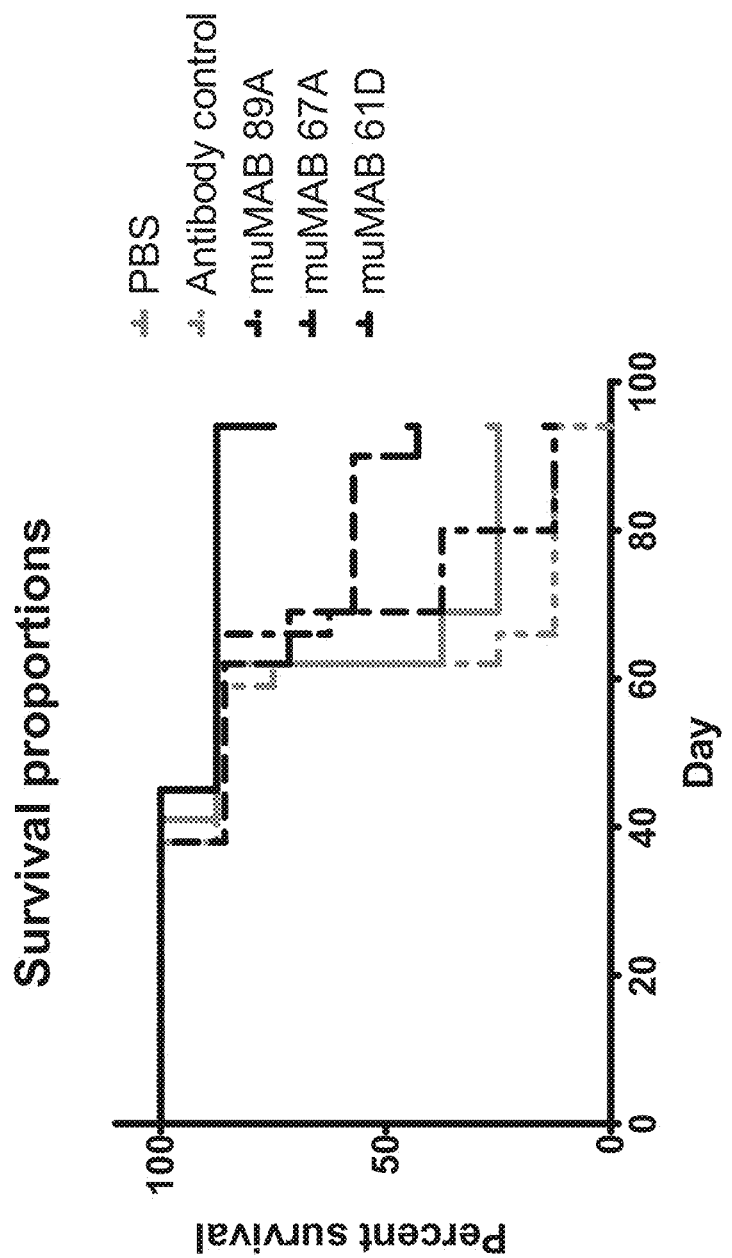

FIG. 22A and FIG. 22B show therapeutic long term effect of anti-CLDN6 murine monoclonal antibodies muMAB 61D, 67A and 89A in an advanced treatment xenograft model using mice engrafted with the tumor cell line NEC8.

17 days after engraftment mice were treated for 42 days with the CLDN6 specific antibodies muMAB 61D, 67A and 89A. The tumor growth has been monitored for additional 49 days (FIG. 22A). The survival plot showed prolonged survival of mice treated with the CLDN6 specific antibodies muMAB 61D and 67A (FIG. 22B).

Figure 23:
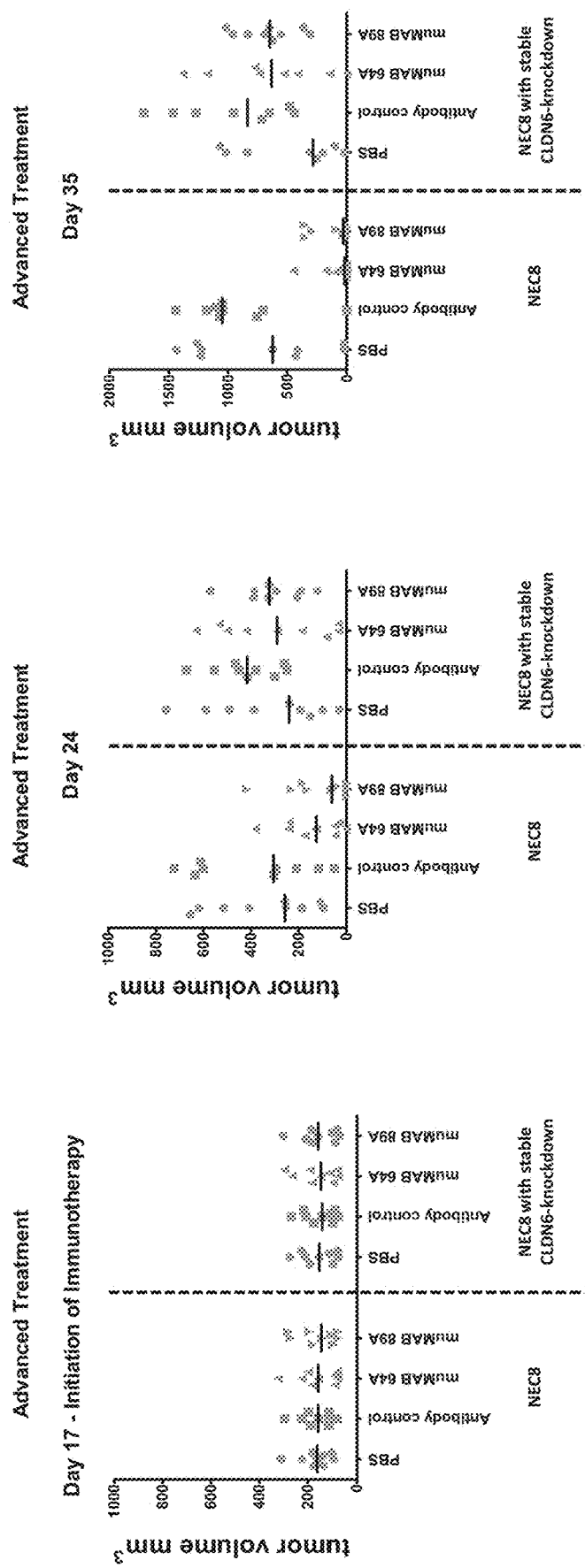

FIG. 23 shows therapeutic effect of anti-CLDN6 murine monoclonal antibodies muMAB 64A and 89A in an advanced treatment xenograft model using mice engrafted with NEC8 wildtype and NEC8 cells with a stable CLDN6 knock-down.

MuMAB 64A and 89A only show therapeutic effect in mice engrafted with NEC8 wildtype but not in mice engrafted with NEC8 CLDN6 knock-down cells demonstrating target-specificity of the antibodies in vivo.

FIG. 24 shows high resolution epitope-mapping of chimMAB 61D, 64A, 67A and 89A.

Alanine mutants are named as 'wildtype residue number alanine' or 'wildtype residue number glycine' in case of wildtype-alanine, where the amino acids are given in the single-letter code. The amino acids F35, G37, S39 and possibly T33 of the first extracellular domain of CLDN6 are important for the interaction with the CLDN6 specific chimeric antibodies chimAB 61D, 64A, 67A and 89A. Residue 140 is essential for the binding of chimAB 89A and it contributes to the binding of chimAB 61D and 67A. In addition, L151 of the second extracellular domain of CLDN6 contributes to the interaction with chimAB 67A. Although immunofluorescence experiments confirmed the expression of CLDN6 mutants P28A, W30A, G49A, L50A, W51A, C54A and C64A they did not show membraneous staining. For this reason we cannot exclude interaction of our antibodies with these amino acids. Altogether, the epitope as identified here is consistent with our immunization strategy using DNA and peptides of the EC1 domain of CLDN6.

Figure 25:
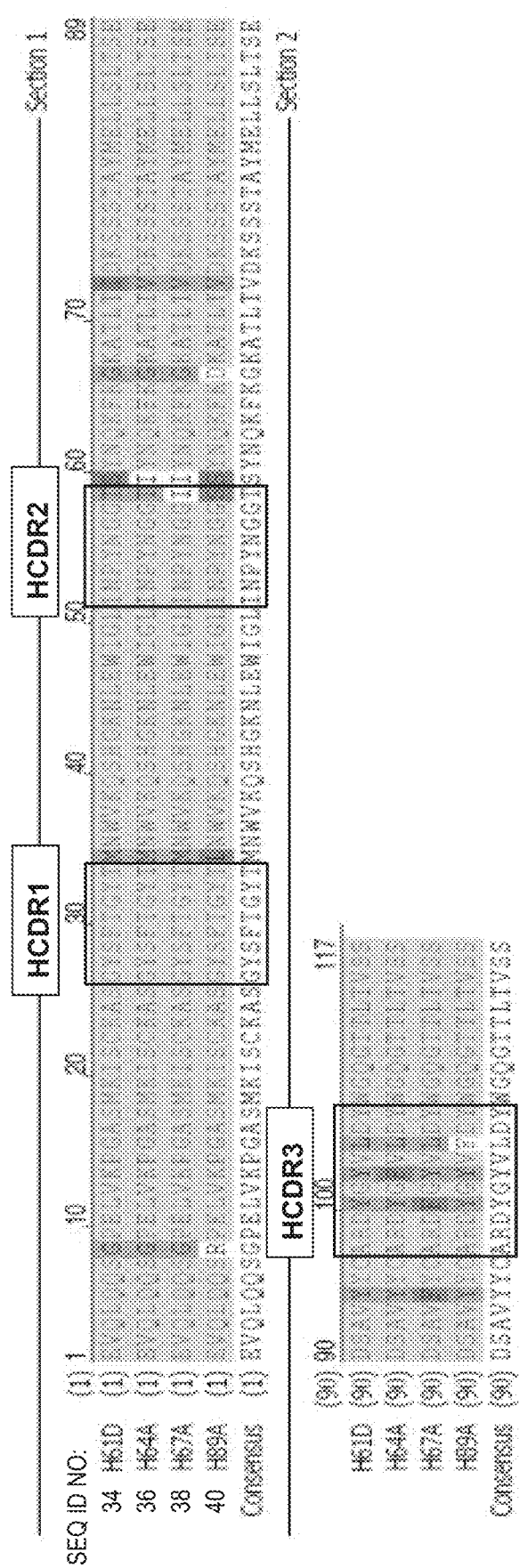

FIG. 25 shows alignment of heavy chain variable region amino acid sequences of CLDN6 specific antibodies of the invention.

The CDR sequences (HCDR1, HCDR2, and HCDR3) are outlined by a box.

Figure 26:
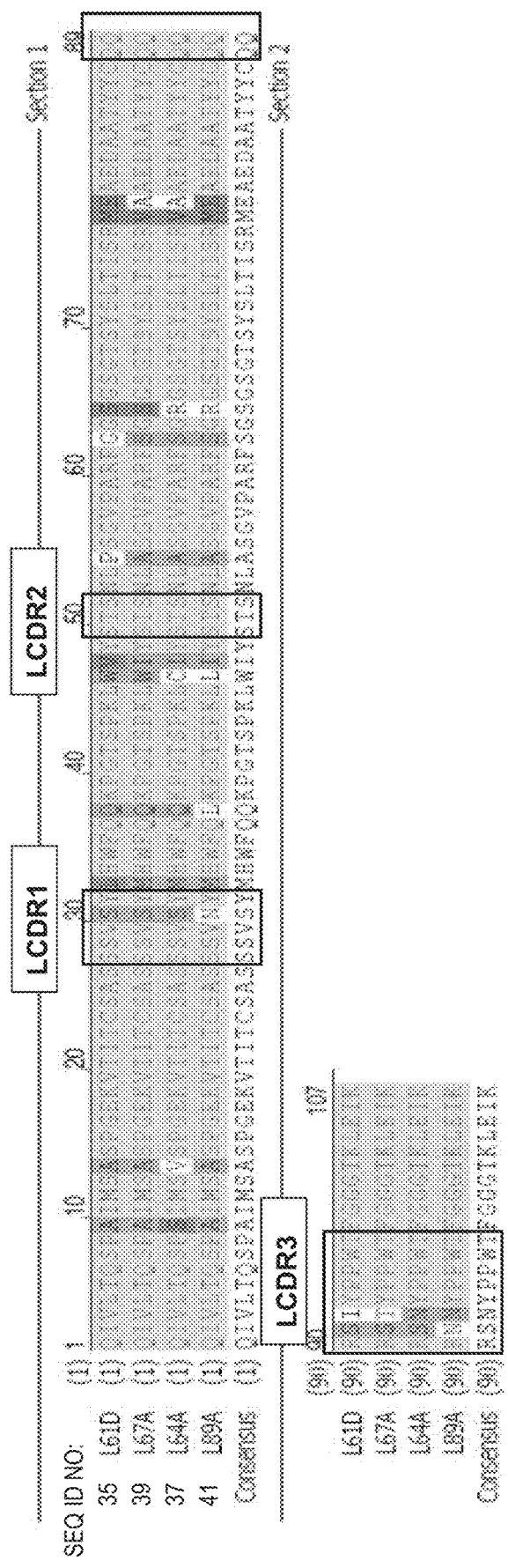

FIG. 26 shows alignment of light chain variable region amino acid sequences of CLDN6 specific antibodies of the invention.

The CDR sequences (LCDR1, LCDR2, and LCDR3) are outlined by a box.

DEFINITION OF TERMS

In order that the present invention may be more readily understood, certain terms are first defined. Additional definitions are set forth throughout the detailed description.

Throughout this specification and the claims which follow, unless the context requires otherwise, the word "comprise", and variations such as "comprises" and "comprising", will be understood to imply the inclusion of a stated member, integer or step or group of members, integers or steps but not the exclusion of any other member, integer or step or group of members, integers or steps. The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as"), provided herein is intended merely to better illustrate the invention and does not pose a limitation on the scope of the invention otherwise claimed. No language in the specification should be construed as indicating any non-claimed element essential to the practice of the invention.

Claudins are a family of proteins that are the most important components of tight junctions, where they establish the paracellular barrier that controls the flow of molecules in the intercellular space between cells of an epithelium. Claudins are transmembrane proteins spanning the membrane 4 times with the N-terminal and the C-terminal end both located in the cytoplasm. The first extracellular loop consists on average of 53 amino acids and the second one of around 24 amino acids. CLDN6 and CLDN9 are the most similar members of the CLDN family.

The term "CLDN" as used herein means claudin and includes CLDN6, CLDN9, CLDN4 and CLDN3. Preferably, a CLDN is a human CLDN.

The term "CLDN6" preferably relates to human CLDN6, and, in particular, to (i) a nucleic acid comprising a nucleic acid sequence encoding the amino acid sequence of SEQ ID NO: 2 or encoding the amino sequence of SEQ ID NO: 8 such as a nucleic acid comprising the nucleic acid sequence of SEQ ID NO: 1 or (ii) a protein comprising the amino acid sequence of SEQ ID NO: 2 or comprising the amino acid sequence of SEQ ID NO: 8. The first extracellular loop of CLDN6 preferably comprises amino acids 28 to 80, more preferably amino acids 28 to 76 of the amino acid sequence shown in SEQ ID NO: 2 or the amino acid sequence shown in SEQ ID NO: 8, such as the amino acid sequence shown in SEQ ID NO: 7. The second extracellular loop of CLDN6 preferably comprises amino acids 138 to 160, preferably amino acids 141 to 159, more preferably amino acids 145 to 157 of the amino acid sequence shown in SEQ ID NO: 2 or the amino acid sequence shown in SEQ ID NO: 8, such as the amino acid sequence shown in SEQ ID NO: 6. Said first and second extracellular loops preferably form the extracellular portion of CLDN6.

The term "CLDN9" preferably relates to human CLDN9, and, in particular, to (i) a nucleic acid comprising a nucleic acid sequence encoding the amino acid sequence of SEQ ID NO: 9 or (ii) a protein comprising the amino acid sequence of SEQ ID NO: 9. The first extracellular loop of CLDN9 preferably comprises amino acids 28 to 76 of the amino acid sequence shown in SEQ ID NO: 9. The second extracellular loop of CLDN9 preferably comprises amino acids 141 to 159 of the amino acid sequence shown in SEQ ID NO: 9. Said first and second extracellular loops preferably form the extracellular portion of CLDN9.

The term "CLDN4" preferably relates to human CLDN4, and, in particular, to (i) a nucleic acid comprising a nucleic acid sequence encoding the amino acid sequence of SEQ ID NO: 10 or (ii) a protein comprising the amino acid sequence of SEQ ID NO: 10. The first extracellular loop of CLDN4 preferably comprises amino acids 28 to 76 of the amino acid sequence shown in SEQ ID NO: 10. The second extracellular loop of CLDN4 preferably comprises amino acids 141 to 159 of the amino acid sequence shown in SEQ ID NO: 10. Said first and second extracellular loops preferably form the extracellular portion of CLDN4.

The term "CLDN3" preferably relates to human CLDN3, and, in particular, to (i) a nucleic acid comprising a nucleic acid sequence encoding the amino acid sequence of SEQ ID NO: 11 or (ii) a protein comprising the amino acid sequence of SEQ ID NO: 11. The first extracellular loop of CLDN3 preferably comprises amino acids 27 to 75 of the amino acid sequence shown in SEQ ID NO: 11. The second extracellular loop of CLDN3 preferably comprises amino acids 140 to 158 of the amino acid sequence shown in SEQ ID NO: 11. Said first and second extracellular loops preferably form the extracellular portion of CLDN3.

The above described CLDN sequences include any variants of said sequences, in particular mutants, splice variants, conformations, isoforms, allelic variants, species variants and species homologs, in particular those which are naturally present. An allelic variant relates to an alteration in the normal sequence of a gene, the significance of which is often unclear. Complete gene sequencing often identifies numerous allelic variants for a given gene. A species homolog is a nucleic acid or amino acid sequence with a different species of origin from that of a given nucleic acid or amino acid sequence. The term "CLDN" shall encompass (i) CLDN splice variants, (ii) CLDN-posttranslationally modified variants, particularly including variants with different glycosylation such as N-glycosylation status, (iii) CLDN conformation variants, (iv) CLDN cancer related and CLDN non-cancer related variants. Preferably, a CLDN is present in its native conformation.

CLDN6 has been found to be expressed, for example, in ovarian cancer, lung cancer, gastric cancer, breast cancer, hepatic cancer, pancreatic cancer, skin cancer, melanomas, head neck cancer, sarcomas, bile duct cancer, renal cell cancer, and urinary bladder cancer. CLDN6 is a particularly preferred target for the prevention and/or treatment of ovarian cancer, in particular ovarian adenocarcinoma and ovarian teratocarcinoma, lung cancer, including small cell lung cancer (SCLC) and non-small cell lung cancer (NSCLC), in particular squamous cell lung carcinoma and adenocarcinoma, gastric cancer, breast cancer, hepatic cancer, pancreatic cancer, skin cancer, in particular basal cell carcinoma and squamous cell carcinoma, malignant melanoma, head and neck cancer, in particular malignant pleomorphic adenoma, sarcoma, in particular synovial sarcoma and carcinosarcoma, bile duct cancer, cancer of the urinary bladder, in particular transitional cell carcinoma and papillary carcinoma, kidney cancer, in particular renal cell carcinoma including clear cell renal cell carcinoma and papillary renal cell carcinoma, colon cancer, small bowel cancer, including cancer of the ileum, in particular small bowel adenocarcinoma and adenocarcinoma of the ileum, testicular embryonal carcinoma, placental choriocarcinoma, cervical cancer, testicular cancer, in particular testicular seminoma, testicular teratoma and embryonic testicular cancer, uterine cancer, a germ cell tumor such as a teratocarcinoma or an embryonal carcinoma, in particular a germ cell tumor of the testis, and the metastatic forms thereof. In one embodiment, the cancer disease associated with CLDN6 expression is selected from the group consisting of ovarian cancer, lung cancer, metastatic ovarian cancer and metastatic lung cancer. Preferably, the ovarian cancer is a carcinoma or an adenocarcinoma. Preferably, the lung cancer is a carcinoma or an adenocarcinoma, and preferably is bronchiolar cancer such as a bronchiolar carcinoma or bronchiolar adenocarcinoma. In one embodiment, the tumor cell associated with CLDN6 expression is a cell of such a cancer.

The term "portion" refers to a fraction. With respect to a particular structure such as an amino acid sequence or protein the term "portion" thereof may designate a continuous or a discontinuous fraction of said structure. Preferably, a portion of an amino acid sequence comprises at least 1%, at least 5%, at least 10%, at least 20%, at least 30%, preferably at least 40%, preferably at least 50%, more preferably at least 60%, more preferably at least 70%, even more preferably at least 80%, and most preferably at least 90% of the amino acids of said amino acid sequence. Preferably, if the portion is a discontinuous fraction said discontinuous fraction is composed of 2, 3, 4, 5, 6, 7, 8, or more parts of a structure, each part being a continuous element of the structure. For example, a discontinuous fraction of an amino acid sequence may be composed of 2, 3, 4, 5, 6, 7, 8, or more, preferably not more than 4 parts of said amino acid sequence, wherein each part preferably comprises at least 5 continuous amino acids, at least 10 continuous amino acids, preferably at least 20 continuous amino acids, preferably at least 30 continuous amino acids of the amino acid sequence.

The terms "part" and "fragment" are used interchangeably herein and refer to a continuous element. For example, a part of a structure such as an amino acid sequence or protein refers to a continuous element of said structure. A portion, a part or a fragment of a structure preferably comprises one or more functional properties of said structure. For example, a portion, a part or a fragment of an epitope or peptide is preferably immunologically equivalent to the epitope or peptide it is derived from.

The term "an extracellular portion of a CLDN" in the context of the present invention refers to a part of a CLDN facing the extracellular space of a cell and preferably being accessible from the outside of said cell, e.g., by antibodies located outside the cell. Preferably, the term refers to one or more extracellular loops or a part thereof or any other extracellular part of a CLDN which is preferably specific for said CLDN. Preferably, said part comprises at least 5, at least 8, at least 10, at least 15, at least 20, at least 30, or at least 50 amino acids or more.

The term "CLDN associated with the surface of a cell" is to be understood to relate to native CLDN, i.e. CLDN in its non-denatured, preferably naturally folded state. Preferably, the term "CLDN associated with the surface of a cell" means that the CLDN is associated with and located at the plasma membrane of said cell, wherein at least a part of the CLDN, preferably the extracellular portion, faces the extracellular space of said cell and is accessible from the outside of said cell, e.g., by antibodies located outside the cell. The association may be direct or indirect. For example, the association may be by one or more transmembrane domains, one or more lipid anchors, and/or by the interaction with any other protein, lipid, saccharide, or other structure that can be found on the outer leaflet of the plasma membrane of a cell. For example, a CLDN associated with the surface of a cell may be a transmembrane protein, i.e. an integral membrane protein, having an extracellular portion or may be a protein associated with the surface of a cell by interacting with another protein that is a transmembrane protein.

CLDN6 is associated with the surface of a cell if it is located at the surface of said cell and is accessible to binding by CLDN6-specific antibodies added to the cell. In preferred embodiments, a cell being characterized by association of CLDN6 with its cell surface is a cell expressing CLDN6. It is to be understood that in the case where CLDN6 is expressed by cells, the CLDN6 associated with the surface of said cells may only be a portion of the expressed CLDN6.

The term "a cell carrying a CLDN" preferably means that said cell carries a CLDN on its surface, i.e., that the CLDN is associated with the surface of said cell.

"Cell surface" or "surface of a cell" is used in accordance with its normal meaning in the art, and thus includes the outside of the cell which is accessible to binding by proteins and other molecules.

The expression "CLDN expressed on the surface of a cell" means that the CLDN expressed by a cell is found in association with the surface of said cell.

According to the invention CLDN6 is not substantially expressed in a cell and is not substantially associated with a cell surface if the level of expression and association is lower compared to expression and association in placenta cells or placenta tissue. Preferably, the level of expression and association is less than 10%, preferably less than 5%, 3%, 2%, 1%, 0.5%, 0.1% or 0.05% of the expression and association in placenta cells or placenta tissue or even lower. Preferably, CLDN6 is not substantially expressed in a cell and is not substantially associated with a cell surface if the level of expression and association exceeds the level of expression and association in non-tumorigenic, non-cancerous tissue other than placenta tissue by no more than 2-fold, preferably 1,5-fold, and preferably does not exceed the level of expression and association in said non-tumorigenic, non-cancerous tissue. Preferably, CLDN6 is not substantially expressed in a cell and is not substantially associated with a cell surface if the level of expression or association is below the detection limit and/or if the level of expression or association is too low to allow binding by CLDN6-specific antibodies added to the cells.

According to the invention CLDN6 is expressed in a cell and is associated with a cell surface if the level of expression and association exceeds the level of expression and association in non-tumorigenic, non-cancerous tissue other than placenta tissue, preferably by more than 2-fold, preferably 10-fold, 100-fold, 1000-fold, or 10000-fold. Preferably, CLDN6 is expressed in a cell and is associated with a cell surface if the level of expression and association is above the detection limit and/or if the level of expression and association is high enough to allow binding by CLDN6-specific antibodies added to the cells. Preferably, CLDN6 expressed in a cell is expressed or exposed on the surface of said cell.

The term "raft" refers to the sphingolipid- and cholesterol-rich membrane microdomains located in the outer leaflet area of the plasma membrane of a cell. The ability of certain proteins to associate within such domains and their ability of forming "aggregates" or "focal aggregates" can effect the protein's function. For example, the translocation of CLDN6 molecules into such structures, after being bound by antibodies of the present invention, creates a high density of CLDN6 antigen-antibody complexes in the plasma membranes. Such a high density of CLDN6 antigen-antibody complexes can enable efficient activation of the complement system during CDC.

According to the invention, the term "disease" refers to any pathological state, including cancer, in particular those forms of cancer described herein.

"Diseases involving cells expressing CLDN6 and being characterized by association of CLDN6 with their cell surface" means according to the invention that expression and association in cells of a diseased tissue or organ is preferably increased compared to the state in a healthy tissue or organ. An increase refers to an increase by at least 10%, in particular at least 20%, at least 50%, at least 100%, at least 200%, at least 500%, at least 1000%, at least 10000% or even more. In one embodiment, expression and association with the cell surface is only found in a diseased tissue, while expression in a healthy tissue is repressed. According to the invention, diseases associated with cells expressing CLDN6 and being characterized by association of CLDN6 with their cell surface include tumor diseases such as cancer diseases. Furthermore, according to the invention, tumor diseases such as cancer diseases preferably are those wherein the tumor cells or cancer cells express CLDN6 and are characterized by association of CLDN6 with their cell surface.

As used herein, a "tumor disease", "tumor-related disease" or "tumorigenic disease" includes a disease characterized by aberrantly regulated cellular growth, proliferation, differentiation, adhesion, and/or migration, which may result in the production of or tendency to produce tumors and/or tumor metastasis. By "tumor cell" is meant an abnormal cell that grows by a rapid, uncontrolled cellular proliferation and continues to grow after the stimuli that initiated the new growth cease.

By "tumor" is meant an abnormal group of cells or a tissue growing by a rapid, uncontrolled cellular proliferation and continues to grow after the stimuli that initiated the new growth cease. Tumors show partial or complete lack of structural organization and functional coordination with the normal tissue, and usually form a distinct mass of tissue, which may be either benign, pre-malignant or malignant.

Preferably, a "tumor disease", "tumor-related disease" or "tumorigenic disease" according to the invention is a cancer disease, i.e. a malignant disease and a tumor cell is a cancer cell. Preferably, a "tumor disease", "tumor-related disease" or "tumorigenic disease" is characterized by cells expressing CLDN6 and being characterized by association of CLDN6 with their cell surface and a tumor cell expresses CLDN6 and is characterized by association of CLDN6 with its cell surface.

A cell expressing CLDN6 and being characterized by association of CLDN6 with its cell surface preferably is a tumor cell or cancer cell, preferably of the tumors and cancers described herein. Preferably, such cell is a cell other than a placental cell.

Preferred cancer diseases or cancers according to the invention are selected from the group consisting of ovarian cancer, in particular ovarian adenocarcinoma and ovarian teratocarcinoma, lung cancer, including small cell lung cancer (SCLC) and non-small cell lung cancer (NSCLC), in particular squamous cell lung carcinoma and adenocarcinoma, gastric cancer, breast cancer, hepatic cancer, pancreatic cancer, skin cancer, in particular basal cell carcinoma and squamous cell carcinoma, malignant melanoma, head and neck cancer, in particular malignant pleomorphic adenoma, sarcoma, in particular synovial sarcoma and carcinosarcoma, bile duct cancer, cancer of the urinary bladder, in particular transitional cell carcinoma and papillary carcinoma, kidney cancer, in particular renal cell carcinoma including clear cell renal cell carcinoma and papillary renal cell carcinoma, colon cancer, small bowel cancer, including cancer of the ileum, in particular small bowel adenocarcinoma and adenocarcinoma of the ileum, testicular embryonal carcinoma, placental choriocarcinoma, cervical cancer, testicular cancer, in particular testicular seminoma, testicular teratoma and embryonic testicular cancer, uterine cancer, a germ cell tumor such as a teratocarcinoma or an embryonal carcinoma, in particular a germ cell tumor of the testis, and the metastatic forms thereof.

The main types of lung cancer are small cell lung carcinoma (SCLC) and non-small cell lung carcinoma (NSCLC). There are three main sub-types of the non-small cell lung carcinomas: squamous cell lung carcinoma, adenocarcinoma, and large cell lung carcinoma. Adenocarcinomas account for approximately 10% of lung cancers. This cancer usually is seen peripherally in the lungs, as opposed to small cell lung cancer and squamous cell lung cancer, which both tend to be more centrally located.

Skin cancer is a malignant growth on the skin. The most common skin cancers are basal cell cancer, squamous cell cancer, and melanoma. Malignant melanoma is a serious type of skin cancer. It is due to uncontrolled growth of pigment cells, called melanocytes.

According to the invention, a "carcinoma" is a cancer that begins in the lining layer (epithelial cells) of organs.

"Bronchiolar carcinoma" is a carcinoma of the lung, thought to be derived from epithelium of terminal bronchioles, in which the neoplastic tissue extends along the alveolar walls and grows in small masses within the alveoli. Mucin may be demonstrated in some of the cells and in the material in the alveoli, which also includes denuded cells.

"Adenocarcinoma" is a cancer that originates in glandular tissue. This tissue is also part of a larger tissue category known as epithelial tissue. Epithelial tissue includes skin, glands and a variety of other tissue that lines the cavities and organs of the body. Epithelium is derived embryologically from ectoderm, endoderm and mesoderm. To be classified as adenocarcinoma, the cells do not necessarily need to be part of a gland, as long as they have secretory properties. This form of carcinoma can occur in some higher mammals, including humans. Well differentiated adenocarcinomas tend to resemble the glandular tissue that they are derived from, while poorly differentiated may not. By staining the cells from a biopsy, a pathologist will determine whether the tumor is an adenocarcinoma or some other type of cancer. Adenocarcinomas can arise in many tissues of the body due to the ubiquitous nature of glands within the body. While each gland may not be secreting the same substance, as long as there is an exocrine function to the cell, it is considered glandular and its malignant form is therefore named adenocarcinoma. Malignant adenocarcinomas invade other tissues and often metastasize given enough time to do so. Ovarian adenocarcinoma is the most common type of ovarian carcinoma. It includes the serous and mucinous adenocarcinomas, the clear cell adenocarcinoma and the endometrioid adenocarcinoma.

"Cystadenocarcinoma" is a malignant form of a surface epithelial-stromal tumor, a type of ovarian cancer.

Surface epithelial-stromal tumors are a class of ovarian neoplasms that are thought to be derived from the ovarian surface epithelium (modified peritoneum) or from ectopic endometrial or Fallopian tube (tubal) tissue. This group of tumors accounts for the majority of all ovarian tumors.

Teratocarcinoma refers to a germ cell tumor that is a mixture of teratoma with embryonal carcinoma, or with choriocarcinoma, or with both. Choriocarcinoma is a malignant, trophoblastic and aggressive cancer, usually of the placenta. It is characterized by early hematogenous spread to the lungs.

A sarcoma is a cancer of the connective tissue (bone, cartilage, fat) resulting in mesoderm proliferation. This is in contrast to carcinomas, which are of epithelial origin. A synovial sarcoma is a rare form of cancer which usually occurs near to the joints of the arm or leg. It is one of the soft tissue sarcomas.

Renal cell carcinoma also known as renal cell cancer or renal cell adenocarcinoma is a kidney cancer that originates in the lining of the proximal convoluted tubule, the very small tubes in the kidney that filter the blood and remove waste products. Renal cell carcinoma is by far the most common type of kidney cancer in adults and the most lethal of all the genitourinary tumors. Distinct subtypes of renal cell carcinoma are clear cell renal cell carcinoma and papillary renal cell carcinoma. Clear cell renal cell carcinoma is the most common form of renal cell carcinoma. When seen under a microscope, the cells that make up clear cell renal cell carcinoma appear very pale or clear. Papillary renal cell carcinoma is the second most common subtype. These cancers form little finger-like projections (called papillae) in some, if not most, of the tumors.

A germ cell tumor is a neoplasm derived from germ cells. Germ cell tumors can be cancerous or non-cancerous tumors. Germ cells normally occur inside the gonads (ovary and testis). Germ cell tumors that originate outside the gonads (e.g. in head, inside the mouth, neck, pelvis; in fetuses, babies, and young children most often found on the body midline, particularly at the tip of the tailbone) may be birth defects resulting from errors during development of the embryo.

The two major classes of germ cell tumors are the seminomas and non-seminomas, wherein non-seminomas include: teratocarcinoma, embryonal carcinoma, yolk sac tumors, choriocarcinoma and differentiated teratoma. Most cell lines from non-seminomas are equivalent to embryonal carcinomas, that is, they are composed almost entirely of stem cells which do not differentiate under basal conditions, though some may respond to inducers of differentiation such as retinoic acid.

By "metastasis" is meant the spread of cancer cells from its original site to another part of the body. The formation of metastasis is a very complex process and depends on detachment of malignant cells from the primary tumor, invasion of the extracellular matrix, penetration of the endothelial basement membranes to enter the body cavity and vessels, and then, after being transported by the blood, infiltration of target organs. Finally, the growth of a new tumor at the target site depends on angiogenesis. Tumor metastasis often occurs even after the removal of the primary tumor because tumor cells or components may remain and develop metastatic potential. In one embodiment, the term "metastasis" according to the invention relates to "distant metastasis" which relates to a metastasis which is remote from the primary tumor and the regional lymph node system.

The cells of a secondary or metastatic tumor are like those in the original tumor. This means, for example, that, if ovarian cancer metastasizes to the liver, the secondary tumor is made up of abnormal ovarian cells, not of abnormal liver cells. The tumor in the liver is then called metastatic ovarian cancer, not liver cancer.

By "treat" is meant to administer a compound or composition as described herein to a subject in order to prevent or eliminate a disease, including reducing the size of a tumor or the number of tumors in a subject; arrest or slow a disease in a subject; inhibit or slow the development of a new disease in a subject; decrease the frequency or severity of symptoms and/or recurrences in a subject who currently has or who previously has had a disease; and/or prolong, i.e. increase the lifespan of the subject.

The term "treatment of a disease" includes curing, shortening the duration, ameliorating, preventing, slowing down or inhibiting progression or worsening, or preventing or delaying the onset of a disease or the symptoms thereof.

By "being at risk" is meant a subject, i.e. a patient, that is identified as having a higher than normal chance of developing a disease, in particular cancer, compared to the general population. In addition, a subject who has had, or who currently has, a disease, in particular cancer is a subject who has an increased risk for developing a disease, as such a subject may continue to develop a disease. Subjects who currently have, or who have had, a cancer also have an increased risk for cancer metastases.

The term "immunotherapy" relates to a treatment involving a specific immune reaction. In the context of the present invention, terms such as "protect", "prevent", "prophylactic", "preventive", or "protective" relate to the prevention or treatment or both of the occurrence and/or the propagation of a tumor in an individual. The term "immunotherapy" in the context of the present invention preferably refers to active tumor immunization or tumor vaccination. A prophylactic administration of an immunotherapy, for example, a prophylactic administration of the composition of the invention, preferably protects the recipient from the development of tumor growth. A therapeutic administration of an immunotherapy, for example, a therapeutic administration of the composition of the invention, may lead to the inhibition of the progress/growth of the tumor. This comprises the deceleration of the progress/growth of the tumor, in particular a disruption of the progression of the tumor, which preferably leads to elimination of the tumor. A therapeutic administration of an immunotherapy may protect the individual, for example, from the dissemination or metastasis of existing tumors.

The term "immunization" or "vaccination" describes the process of administering antigen to a subject with the purpose of inducing an immune response for therapeutic or prophylactic reasons.

The terms "subject", "individual", "organism" or "patient" are used interchangeably and relate to vertebrates, preferably mammals. For example, mammals in the context of the present invention are humans, non-human primates, domesticated animals such as dogs, cats, sheep, cattle, goats, pigs, horses etc., laboratory animals such as mice, rats, rabbits, guinea pigs, etc. as well as animals in captivity such as animals of zoos. The term "animal" as used herein also includes humans. The term "subject" may also include a patient, i.e., an animal, preferably a human having a disease, preferably a disease associated with expression of CLDN6, preferably a tumorigenic disease such as a cancer.

The term "adjuvant" relates to compounds which prolongs or enhances or accelerates an immune response. The composition of the present invention preferably exerts its effect without addition of adjuvants. Still, the composition of the present application may contain any known adjuvant. Adjuvants comprise a heterogeneous group of compounds such as oil emulsions (e.g., Freund's adjuvants), mineral compounds (such as alum), bacterial products (such as *Bordetella pertussis* toxin), liposomes, and immune-stimulating complexes. Examples for adjuvants are monophosphoryl-lipid-A (MPL SmithKline Beecham). Saponins such as QS21 (SmithKline Beecham), DQS21 (SmithKline Beecham; WO 96/33739), QS7, QS17, QS18, and QS-L1 (So et al., 1997, Mol. Cells 7: 178-186), incomplete Freund's adjuvants, complete Freund's adjuvants, vitamin E, montanid, alum, CpG oligonucleotides (Krieg et al., 1995, Nature 374: 546-549), and various water-in-oil emulsions which are prepared from biologically degradable oils such as squalene and/or tocopherol.

According to the invention, a sample may be any sample useful according to the present invention, in particular a biological sample such a tissue sample, including bodily fluids, and/or a cellular sample and may be obtained in the conventional manner such as by tissue biopsy, including punch biopsy, and by taking blood, bronchial aspirate, sputum, urine, feces or other body fluids. According to the invention, the term "biological sample" also includes fractions of biological samples.

The term "antibody" refers to a glycoprotein comprising at least two heavy (H) chains and two light (L) chains inter-connected by disulfide bonds, and includes any molecule comprising an antigen binding portion thereof. The term "antibody" includes monoclonal antibodies and fragments or derivatives thereof, including, without limitation, human monoclonal antibodies, humanized monoclonal antibodies, chimeric monoclonal antibodies, single chain antibodies, e.g., scFv's and antigen-binding antibody fragments such as Fab and Fab' fragments and also includes all recombinant forms of antibodies, e.g., antibodies expressed in prokaryotes, unglycosylated antibodies, and any antigen-binding antibody fragments and derivatives as described herein. Each heavy chain is comprised of a heavy chain variable region (abbreviated herein as VH) and a heavy chain constant region. Each light chain is comprised of a light chain variable region (abbreviated herein as VL) and a light chain constant region. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxyterminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

According to the invention, the term "at least one of the CDR sequences" preferably means at least the CDR3 sequence. The term "CDR sequences of an antibody chain" preferably relates to CDR1, CDR2 and CDR3 of the heavy chain or light chain of an antibody.

According to the invention, a reference to an antibody chain comprising a particular CDR sequence such as a particular CDR3 sequence means that said particular CDR sequence either forms the CDR region such as the CDR3 region of said antibody chain, i.e. the CDR region consists of said particular CDR sequence, or forms a part of the CDR region such as the CDR3 region of said antibody chain, i.e. the CDR region comprises said particular CDR sequence.

If according to the invention reference is made to an antibody comprising a particular antibody heavy chain and/or a particular antibody light chain, such as a chain comprising particular CDR sequences, it is preferred that both heavy chains and/or both light chains of the antibody are each composed of the particular antibody heavy chain and/or the particular antibody light chain.

The term "humanized antibody" refers to a molecule having an antigen binding site that is substantially derived from an immunoglobulin from a non-human species, wherein the remaining immunoglobulin structure of the molecule is based upon the structure and/or sequence of a human immunoglobulin. The antigen binding site may either comprise complete variable domains fused onto constant domains or only the complementarity determining regions (CDR) grafted onto appropriate framework regions in the variable domains. Antigen binding sites may be wild-type or modified by one or more amino acid substitutions, e.g. modified to resemble human immunoglobulins more closely. Some forms of humanized antibodies preserve all CDR sequences (for example a humanized mouse antibody which contains all six CDRs from the mouse antibody). Other forms have one or more CDRs which are altered with respect to the original antibody.

The term "chimeric antibody" refers to those antibodies wherein one portion of each of the amino acid sequences of heavy and light chains is homologous to corresponding sequences in antibodies derived from a particular species or belonging to a particular class, while the remaining segment of the chain is homologous to corresponding sequences in another. Typically the variable region of both light and heavy chains mimics the variable regions of antibodies derived from one species of mammals, while the constant portions are homologous to sequences of antibodies derived from another. One clear advantage to such chimeric forms is that the variable region can conveniently be derived from presently known sources using readily available B-cells or hybridomas from non-human host organisms in combination with constant regions derived from, for example, human cell preparations. While the variable region has the advantage of ease of preparation and the specificity is not affected by the source, the constant region being human, is less likely to elicit an immune response from a human subject when the antibodies are injected than would the constant region from a non human source. However the definition is not limited to this particular example.

The term "antigen-binding portion" of an antibody (or simply "binding portion"), as used herein, refers to one or more fragments of an antibody that retain the ability to specifically bind to an antigen. It has been shown that the antigen-binding function of an antibody can be performed by fragments of a full-length antibody. Examples of binding fragments encompassed within the term "antigen-binding portion" of an antibody include (i) Fab fragments, monovalent fragments consisting of the VL, VH, CL and CH domains; (ii) F(ab)$_2$ fragments, bivalent fragments comprising two Fab fragments linked by a disulfide bridge at the hinge region; (iii) Fd fragments consisting of the VH and CH domains; (iv) Fv fragments consisting of the VL and VH domains of a single arm of an antibody, (v) dAb fragments (Ward et al., (1989) Nature 341: 544-546), which consist of a VH domain; (vi) isolated complementarity determining regions (CDR), and (vii) combinations of two or more isolated CDRs which may optionally be joined by a synthetic linker. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242: 423-426; and Huston et al. (1988) Proc. Natl. Acad. Sci. USA 85: 5879-5883). Such single chain antibodies are also intended to be encompassed within the term "antigen-binding portion" of an antibody. A further example is binding-domain immunoglobulin fusion proteins comprising (i) a binding domain polypeptide that is fused to an immunoglobulin hinge region polypeptide, (ii) an immunoglobulin heavy chain CH2 constant region fused to the hinge region, and (iii) an immunoglobulin heavy chain CH3 constant region fused to the CH2 constant region. The binding domain polypeptide can be a heavy chain variable region or a light chain variable region. The binding-domain immunoglobulin fusion proteins are further disclosed in US 2003/0118592 and US 2003/0133939. These antibody fragments are obtained using conventional techniques known to those with skill in the art, and the fragments are screened for utility in the same manner as are intact antibodies.

The term "epitope" refers to an antigenic determinant in a molecule, i.e., to the part in a molecule that is recognized by the immune system, for example, that is recognized by an antibody. For example, epitopes are the discrete, three-dimensional sites on an antigen, which are recognized by the immune system. In the context of the present invention, the epitope is preferably derived from a CLDN protein. Epitopes usually consist of chemically active surface groupings of molecules such as amino acids or sugar side chains and usually have specific three dimensional structural characteristics, as well as specific charge characteristics. Conformational and non-conformational epitopes are distinguished in that the binding to the former but not the latter is lost in the presence of denaturing solvents. An epitope of a protein such as a CLDN preferably comprises a continuous or discontinuous portion of said protein and is preferably between 5 and 100, preferably between 5 and 50, more preferably between 8 and 30, most preferably between 10 and 25 amino acids in length, for example, the epitope may be preferably 8, 9, 10, 11, 12, 13, 14, 15, 16, 17, 18, 19, 20, 21, 22, 23, 24, or 25 amino acids in length.

The term "discontinuous epitope" as used herein, means a conformational epitope on a protein antigen which is formed from at least two separate regions in the primary sequence of the protein.

The term "bispecific molecule" is intended to include any agent, e.g., a protein, peptide, or protein or peptide complex, which has two different binding specificities. For example, the molecule may bind to, or interact with (a) a cell surface antigen, and (b) an Fc receptor on the surface of an effector cell. The term "multispecific molecule" or "heterospecific molecule" is intended to include any agent, e.g., a protein, peptide, or protein or peptide complex, which has more than two different binding specificities. For example, the molecule may bind to, or interact with (a) a cell surface antigen, (b) an Fc receptor on the surface of an effector cell, and (c) at least one other component. Accordingly, the invention includes, but is not limited to, bispecific, trispecific, tetraspecific, and other multispecific molecules which are directed to CLDN6, and to other targets, such as Fc receptors on effector cells. The term "bispecific antibodies" also includes diabodies. Diabodies are bivalent, bispecific antibodies in which the VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) Proc. Natl. Acad. Sci. USA 90: 6444-6448; Poljak, R. J., et al. (1994) Structure 2: 1121-1123).

As used herein, the term "heteroantibodies" refers to two or more antibodies, derivatives thereof, or antigen binding regions linked together, at least two of which have different specificities. These different specificities include a binding specificity for an Fc receptor on an effector cell, and a binding specificity for an antigen or epitope on a target cell, e.g., a tumor cell.

The antibodies described herein may be human antibodies. The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo).

The term "monoclonal antibody" as used herein refers to a preparation of antibody molecules of single molecular composition. A monoclonal antibody displays a single binding specificity and affinity for a particular epitope. In one embodiment, the monoclonal antibodies are produced by a hybridoma which includes a B cell obtained from a non-human animal, e.g., mouse, fused to an immortalized cell.

The term "recombinant antibody", as used herein, includes all antibodies that are prepared, expressed, created or isolated by recombinant means, such as (a) antibodies isolated from an animal (e.g., a mouse) that is transgenic or transchromosomal with respect to the immunoglobulin genes or a hybridoma prepared therefrom, (b) antibodies isolated from a host cell transformed to express the antibody, e.g., from a transfectoma, (c) antibodies isolated from a recombinant, combinatorial antibody library, and (d) antibodies prepared, expressed, created or isolated by any other means that involve splicing of immunoglobulin gene sequences to other DNA sequences.

The term "transfectoma", as used herein, includes recombinant eukaryotic host cells expressing an antibody, such as CHO cells, NS/0 cells, HEK293 cells, HEK293T cells, plant cells, or fungi, including yeast cells.

As used herein, a "heterologous antibody" is defined in relation to a transgenic organism producing such an antibody. This term refers to an antibody having an amino acid sequence or an encoding nucleic acid sequence corresponding to that found in an organism not consisting of the transgenic organism, and being generally derived from a species other than the transgenic organism.

As used herein, a "heterohybrid antibody" refers to an antibody having light and heavy chains of different organismal origins. For example, an antibody having a human heavy chain associated with a murine light chain is a heterohybrid antibody.

The invention includes all antibodies and derivatives of antibodies as described herein which for the purposes of the invention are encompassed by the term "antibody". The term "antibody derivatives" refers to any modified form of an antibody, e.g., a conjugate of the antibody and another agent or antibody, or an antibody fragment.

The antibodies described herein are preferably isolated. An "isolated antibody" as used herein, is intended to refer to an antibody which is substantially free of other antibodies having different antigenic specificities (e.g., an isolated antibody that specifically binds to CLDN6 is substantially free of antibodies that specifically bind antigens other than CLDN6). An isolated antibody that specifically binds to an epitope, isoform or variant of human CLDN6 may, however, have cross-reactivity to other related antigens, e.g., from other species (e.g., CLDN6 species homologs). Moreover, an isolated antibody may be substantially free of other cellular material and/or chemicals. In one embodiment of the invention, a combination of "isolated" monoclonal antibodies relates to antibodies having different specificities and being combined in a well defined composition.

According to the present invention, an antibody is capable of binding to a predetermined target if it has a significant affinity for said predetermined target and binds to said predetermined target in standard assays such as the assays described herein. Preferably, an antibody is capable of binding to a target if it detectably binds to said target in a flow cytometry analysis (FACS analysis) wherein binding of said antibody to said target expressed on the surface of intact cells is determined. Preferably, the antibody detectably binds to said target if present in a concentration of 10 µg/ml or lower, 5 µg/ml or lower or 2 µg/ml or lower. Preferably, the antibody detectably binds to said target if present in a concentration of 50 nM or lower, 30 nM or lower or 15 nM or lower. "Affinity" or "binding affinity" is often measured by equilibrium dissociation constant ($K_D$). Preferably, the term "significant affinity" refers to the binding to a predetermined target with a dissociation constant ($K_D$) of $10^{-5}$ M or lower, $10^{-6}$ M or lower, $10^{-7}$ M or lower, $10^{-8}$ M or lower, $10^{-9}$ M or lower, $10^{-10}$ M or lower, $10^{-11}$ M or lower, or $10^{-12}$ M or lower. Antibodies of the present invention preferably have EC50 values for binding to CLDN6 of 6500 ng/ml or lower, 3000 ng/ml or lower, 2500 ng/ml or lower, 2000 ng/ml or lower, 1500 ng/ml or lower, 1000 ng/ml or lower, 500 ng/ml or lower, 400 ng/ml or lower, 300 ng/ml or lower, 200 ng/ml or lower, or 100 ng/ml or lower.

An antibody is not (substantially) capable of binding to a target if it has no significant affinity for said target and does not bind significantly to said target in standard assays. Preferably, an antibody is not (substantially) capable of binding to a target if it does not detectably bind to said target in a flow cytometry analysis (FACS analysis) wherein binding of said antibody to said target expressed on the surface of intact cells is determined. Preferably, the antibody does not detectably bind to said target if present in a concentration of up to 2 µg/ml, preferably up to 5 µg/ml, preferably up to 10 µg/ml, preferably up to 20 µg/ml, more preferably up to 50 µg/ml, in particular up to 100 µg/ml, or up to 150 µg/ml, up to 200 µg/ml or higher. Preferably, the antibody does not detectably bind to said target if present in a concentration of up to 15 nM, preferably up to 30 nM, preferably up to 50 nM, preferably up to 100 nM, preferably up to 150 nM, or up to 170 nM, up to 300 mM, up to 600 nM, up to 1000 nM, up to 1300 nM or higher. Preferably, the antibody does not detectably bind to said target if present in a concentration that saturates binding to the target to which the antibody binds, i.e. CLDN6. Preferably, an antibody has no significant affinity for a target if it binds to said target with a $K_D$ that is at least 10-fold, 100-fold, $10^3$-fold, $10^4$-fold, $10^5$-fold, or $10^6$-fold higher than the $K_D$ for binding to the predetermined target to which the antibody is capable of binding. For example, if the $K_D$ for binding of an antibody to the target to which the antibody is capable of binding is $10^{-7}$ M, the $K_D$ for binding to a target for which the antibody has no significant affinity would be is at least $10^{-6}$ M, $10^{-5}$ M, $10^{-4}$ M, $10^{-3}$ M, $10^{-2}$ M, or $10^{-1}$ M.

An antibody is specific for a predetermined target if it is capable of binding to said predetermined target while it is not capable of binding to other targets, i.e. has no significant affinity for other targets and does not significantly bind to other targets in standard assays. According to the invention, an antibody is specific for CLDN6 if it is capable of binding to CLDN6 but is not capable of binding to other targets, in particular claudin proteins other than CLDN6 such as CLDN9, CLDN4, CLDN3 and CLDN1. Preferably, an antibody is specific for CLDN6 if the affinity for and the binding to a claudin protein other than CLDN6 such as CLDN9, CLDN4, CLDN3 and CLDN1 does not significantly exceed the affinity for or binding to claudin-unrelated proteins such as bovine serum albumin (BSA), casein, human serum albumin (HSA) or non-claudin transmembrane proteins such as MHC molecules or transferrin receptor or any other specified polypeptide. Preferably, an antibody is specific for a predetermined target if it binds to said target with a $K_D$ that is at least 10-fold, 100-fold, $10^3$-fold, $10^4$-fold, $10^5$-fold, or $10^6$-fold lower than the $K_D$ for binding to a target for which it is not specific. For example, if the $K_D$ for binding of an antibody to the target for which it is specific is $10^{-7}$ M, the $K_D$ for binding to a target for which it is not specific would be at least $10^{-6}$ M, $10^{-5}$ M, $10^{-4}$ M, $10^{-3}$ M, $10^{-2}$ M, or $10^{-1}$ M.

Binding of an antibody to a target can be determined experimentally using any suitable method; see, for example, Berzofsky et al., "Antibody-Antigen Interactions" In Fundamental Immunology, Paul, W. E., Ed., Raven Press New York, N Y (1984), Kuby, Janis Immunology, W. H. Freeman and Company New York, N Y (1992), and methods described herein. Affinities may be readily determined using conventional techniques, such as by equilibrium dialysis; by using the BIAcore 2000 instrument, using general procedures outlined by the manufacturer; by radioimmunoassay using radiolabeled target antigen; or by another method known to the skilled artisan. The affinity data may be analyzed, for example, by the method of Scatchard et al., Ann N.Y. Acad. ScL, 51:660 (1949). The measured affinity of a particular antibody-antigen interaction can vary if measured under different conditions, e.g., salt concentration, pH. Thus, measurements of affinity and other antigen-binding parameters, e.g., $K_D$, $IC_{50}$, are preferably made with standardized solutions of antibody and antigen, and a standardized buffer.

A unique feature of the antibody of the present invention is the ability to bind cell surface claudin 6. This is demonstrated by flow cytometry analysis of cells expressing claudin 6.

To test the binding of monoclonal antibodies to live cells expressing claudins, flow cytometry can be used. Briefly, cell lines expressing membrane-associated claudins (grown under standard growth conditions) are mixed with various concentrations of antibodies in PBS containing 2% heat inactivated FCS and 0.1% $NaN_3$ at 4° C. for 30 min. After washing, the cells are reacted with a fluorescently labeled secondary antibody under the same conditions as the primary antibody staining. The samples can be analyzed by FACS using light and side scatter properties to gate on single cells and binding of the labeled antibodies is determined.

The term "binding" according to the invention preferably relates to a specific binding as defined herein.

As used herein, "isotype" refers to the antibody class (e.g., IgM or IgG1) that is encoded by heavy chain constant region genes.

As used herein, "isotype switching" refers to the phenomenon by which the class, or isotype, of an antibody changes from one Ig class to one of the other Ig classes.

The term "naturally occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally occurring.

The term "rearranged" as used herein refers to a configuration of a heavy chain or light chain immunoglobulin locus wherein a V segment is positioned immediately adjacent to a D-J or J segment in a conformation encoding essentially a complete VH or VL domain, respectively. A rearranged immunoglobulin (antibody) gene locus can be identified by comparison to germline DNA; a rearranged locus will have at least one recombined heptamer/nonamer homology element.

The term "unrearranged" or "germline configuration" as used herein in reference to a V segment refers to the configuration wherein the V segment is not recombined so as to be immediately adjacent to a D or J segment.

The term "nucleic acid molecule", as used herein, is intended to include DNA molecules and RNA molecules. A nucleic acid molecule may be single-stranded or double-stranded, but preferably is double-stranded DNA. A nucleic acid molecule can be employed for introduction into, i.e. transfection of, cells, for example, in the form of RNA which can be prepared by in vitro transcription from a DNA template. The RNA can moreover be modified before application by stabilizing sequences, capping, and polyadenylation.

The nucleic acids described according to the invention have preferably been isolated. The term "isolated nucleic acid" means according to the invention that the nucleic acid was (i) amplified in vitro, for example by polymerase chain reaction (PCR), (ii) recombinantly produced by cloning, (iii) purified, for example by cleavage and gel-electrophoretic fractionation, or (iv) synthesized, for example by chemical synthesis. An isolated nucleic acid is a nucleic acid which is available for manipulation by recombinant DNA techniques.

Nucleic acids may, according to the invention, be present alone or in combination with other nucleic acids, which may be homologous or heterologous. In preferred embodiments, a nucleic acid is functionally linked to expression control sequences which may be homologous or heterologous with respect to said nucleic acid wherein the term "homologous" means that the nucleic acid is also functionally linked to the expression control sequence naturally and the term "heterologous" means that the nucleic acid is not functionally linked to the expression control sequence naturally.

A nucleic acid, such as a nucleic acid expressing RNA and/or protein or peptide, and an expression control sequence are "functionally" linked to one another, if they are covalently linked to one another in such a way that expression or transcription of said nucleic acid is under the control or under the influence of said expression control sequence. If the nucleic acid is to be translated into a functional protein, then, with an expression control sequence functionally linked to a coding sequence, induction of said expression control sequence results in transcription of said nucleic acid, without causing a frame shift in the coding sequence or said coding sequence not being capable of being translated into the desired protein or peptide.

The term "expression control sequence" comprises according to the invention promoters, ribosome binding sites, enhancers and other control elements which regulate transcription of a gene or translation of a mRNA. In particular embodiments of the invention, the expression control sequences can be regulated. The exact structure of expression control sequences may vary as a function of the species or cell type, but generally comprises 5'-untranscribed and 5'- and 3'-untranslated sequences which are involved in initiation of transcription and translation, respectively, such as TATA box, capping sequence, CAAT sequence, and the like. More specifically, 5'-untranscribed expression control sequences comprise a promoter region which includes a promoter sequence for transcriptional control of the functionally linked nucleic acid. Expression control sequences may also comprise enhancer sequences or upstream activator sequences.

According to the invention the term "promoter" or "promoter region" relates to a nucleic acid sequence which is located upstream (5') to the nucleic acid sequence being expressed and controls expression of the sequence by providing a recognition and binding site for RNA-polymerase. The "promoter region" may include further recognition and binding sites for further factors which are involved in the regulation of transcription of a gene. A promoter may control the transcription of a prokaryotic or eukaryotic gene. Furthermore, a promoter may be "inducible" and may initiate transcription in response to an inducing agent or may be "constitutive" if transcription is not controlled by an inducing agent. A gene which is under the control of an inducible promoter is not expressed or only expressed to a small extent if an inducing agent is absent. In the presence of the inducing agent the gene is switched on or the level of transcription is increased. This is mediated, in general, by binding of a specific transcription factor.

Promoters which are preferred according to the invention include promoters for SP6, T3 and T7 polymerase, human U6 RNA promoter, CMV promoter, and artificial hybrid promoters thereof (e.g. CMV) where a part or parts are fused to a part or parts of promoters of genes of other cellular proteins such as e.g. human GAPDH (glyceraldehyde-3-phosphate dehydrogenase), and including or not including (an) additional intron(s).

According to the invention, the term "expression" is used in its most general meaning and comprises the production of RNA or of RNA and protein/peptide. It also comprises partial expression of nucleic acids. Furthermore, expression may be carried out transiently or stably. According to the invention, the term expression also includes an "aberrant expression" or "abnormal expression".

"Aberrant expression" or "abnormal expression" means according to the invention that expression is altered, preferably increased, compared to a reference, preferably compared to the state in a non-tumorigenic normal cell or a healthy individual. An increase in expression refers to an increase by at least 10%, in particular at least 20%, at least 50% or at least 100%. In one embodiment, expression is only found in a diseased tissue, while expression in a healthy tissue is repressed.

In a preferred embodiment, a nucleic acid molecule is according to the invention present in a vector, where appropriate with a promoter, which controls expression of the nucleic acid. The term "vector" is used here in its most general meaning and comprises any intermediary vehicle for a nucleic acid which enables said nucleic acid, for example, to be introduced into prokaryotic and/or eukaryotic cells and, where appropriate, to be integrated into a genome. Vectors of this kind are preferably replicated and/or expressed in the cells. Vectors comprise plasmids, phagemids, bacteriophages or viral genomes. The term "plasmid" as used herein generally relates to a construct of extrachromosomal genetic material, usually a circular DNA duplex, which can replicate independently of chromosomal DNA.

As the vector for expression of an antibody, either of a vector type in which the antibody heavy chain and light chain are present in different vectors or a vector type in which the heavy chain and light chain are present in the same vector can be used.

The teaching given herein with respect to specific nucleic acid and amino acid sequences, e.g. those shown in the sequence listing, is to be construed so as to also relate to modifications, i.e. variants, of said specific sequences resulting in sequences which are functionally equivalent to said specific sequences, e.g. amino acid sequences exhibiting properties identical or similar to those of the specific amino acid sequences and nucleic acid sequences encoding amino acid sequences exhibiting properties identical or similar to those of the amino acid sequences encoded by the specific nucleic acid sequences. One important property is to retain binding of an antibody to its target or to sustain effector functions of an antibody such as CDC and/or ADCC. Preferably, a sequence modified with respect to a specific sequence, when it replaces the specific sequence in an antibody retains binding of said antibody to the target and preferably functions of said antibody as described herein.

Similarly, the teaching given herein with respect to specific antibodies or hybridomas producing specific antibodies is to be construed so as to also relate to antibodies characterized by an amino acid sequence and/or nucleic acid sequence which is modified compared to the amino acid sequence and/or nucleic acid sequence of the specific antibodies but being functionally equivalent. One important property is to retain binding of an antibody to its target or to sustain effector functions of an antibody. Preferably, a sequence modified with respect to a specific sequence, when it replaces the specific sequence in an antibody retains binding of said antibody to the target and preferably functions of said antibody as described herein, e.g. CDC mediated lysis or ADCC mediated lysis.

It will be appreciated by those skilled in the art that in particular the sequences of the CDR, hypervariable and variable regions can be modified without losing the ability to bind to a target. For example, CDR regions will be either identical or highly homologous to the regions of antibodies specified herein. By "highly homologous" it is contemplated that from 1 to 5, preferably from 1 to 4, such as 1 to 3 or 1 or 2 substitutions may be made in the CDRs. In addition, the hypervariable and variable regions may be modified so that they show substantial homology with the regions of antibodies specifically disclosed herein.

It is to be understood that the specific nucleic acids described herein also include nucleic acids modified for the sake of optimizing the codon usage in a particular host cell or organism. Differences in codon usage among organisms can lead to a variety of problems concerning heterologous gene expression. Codon optimization by changing one or more nucleotides of the original sequence can result in an optimization of the expression of a nucleic acid, in particular in optimization of translation efficacy, in a homologous or heterologous host in which said nucleic acid is to be expressed.

According to the invention, a variant, derivative, modified form or fragment of a nucleic acid sequence, amino acid sequence, or peptide preferably has a functional property of the nucleic acid sequence, amino acid sequence, or peptide, respectively, from which it has been derived. Such functional properties comprise the interaction with or binding to other molecules. In one embodiment, a variant, derivative, modified form or fragment of a nucleic acid sequence, amino acid sequence, or peptide is immunologically equivalent to the nucleic acid sequence, amino acid sequence, or peptide, respectively, from which it has been derived.

Preferably the degree of identity between a specific nucleic acid sequence and a nucleic acid sequence which is modified with respect to or which is a variant of said specific nucleic acid sequence will be at least 70%, preferably at least 75%, more preferably at least 80%, even more preferably at least 90% or most preferably at least 95%, 96%, 97%, 98% or 99%. Regarding CLDN6 nucleic acid variants, the degree of identity is preferably given for a region of at least about 300, at least about 400, at least about 450, at least about 500, at least about 550, at least about 600 or at least about 630 nucleotides. In preferred embodiments, the degree of identity is given for the entire length of the reference nucleic acid sequence, such as the nucleic acid sequences given in the sequence listing. Preferably, the two sequences are capable of hybridizing and forming a stable duplex with one another, with hybridization preferably being carried out under conditions which allow specific hybridization between polynucleotides (stringent conditions). Stringent conditions are described, for example, in Molecular Cloning: A Laboratory Manual, J. Sambrook et al., Editors, 2nd Edition, Cold Spring Harbor Laboratory press, Cold Spring Harbor, N.Y., 1989 or Current Protocols in Molecular Biology, F. M. Ausubel et al., Editors, John Wiley & Sons, Inc., New York and refer, for example, to hybridization at 65° C. in hybridization buffer (3.5×SSC, 0.02% Ficoll, 0.02% polyvinylpyrrolidone, 0.02% bovine serum albumin, 2.5 mM $NaH_2PO_4$ (pH 7), 0.5% SDS, 2 mM EDTA). SSC is 0.15 M sodium chloride/0.15 M sodium citrate, pH 7. After hybridization, the membrane to which the DNA has been transferred is washed, for example, in 2×SSC at room temperature and then in 0.1-0.5×SSC/0.1×SDS at temperatures of up to 68° C.

The term "variant" according to the invention also includes mutants, splice variants, conformations, isoforms, allelic variants, species variants and species homologs, in particular those which are naturally present. An allelic variant relates to an alteration in the normal sequence of a gene, the significance of which is often unclear. Complete gene sequencing often identifies numerous allelic variants for a given gene. A species homolog is a nucleic acid or amino acid sequence with a different species of origin from that of a given nucleic acid or amino acid sequence.

For the purposes of the present invention, "variants" of an amino acid sequence comprise amino acid insertion variants, amino acid addition variants, amino acid deletion variants and/or amino acid substitution variants. Amino acid deletion variants that comprise the deletion at the N-terminal and/or C-terminal end of the protein are also called N-terminal and/or C-terminal truncation variants.

Amino acid insertion variants comprise insertions of single or two or more amino acids in a particular amino acid sequence. In the case of amino acid sequence variants having an insertion, one or more amino acid residues are inserted into a particular site in an amino acid sequence, although random insertion with appropriate screening of the resulting product is also possible.

Amino acid addition variants comprise amino- and/or carboxy-terminal fusions of one or more amino acids, such as 1, 2, 3, 5, 10, 20, 30, 50, or more amino acids.

Amino acid deletion variants are characterized by the removal of one or more amino acids from the sequence, such as by removal of 1, 2, 3, 5, 10, 20, 30, 50, or more amino acids. The deletions may be in any position of the protein.

Amino acid substitution variants are characterized by at least one residue in the sequence being removed and another residue being inserted in its place. Preference is given to the modifications being in positions in the amino acid sequence which are not conserved between homologous proteins or peptides and/or to replacing amino acids with other ones having similar properties. Preferably, amino acid changes in protein variants are conservative amino acid changes, i.e., substitutions of similarly charged or uncharged amino acids. A conservative amino acid change involves substitution of one of a family of amino acids which are related in their side chains. Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cysteine, serine, threonine, tyrosine) amino acids. Phenylalanine, tryptophan, and tyrosine are sometimes classified jointly as aromatic amino acids.

Preferably the degree of similarity, preferably identity between a specific amino acid sequence and an amino acid sequence which is modified with respect to or which is a variant of said specific amino acid sequence such as between amino acid sequences showing substantial homology will be at least 70%, preferably at least 80%, even more preferably at least 90% or most preferably at least 95%, 96%, 97%, 98% or 99%. The degree of similarity or identity is given preferably for an amino acid region which is at least about 10%, at least about 20%, at least about 30%, at least about 40%, at least about 50%, at least about 60%, at least about 70%, at least about 80%, at least about 90% or about 100% of the entire length of the reference amino acid sequence. For example, if the reference amino acid sequence consists of 200 amino acids, the degree of similarity or identity is given preferably for at least about 20, at least about 40, at least about 60, at least about 80, at least about 100, at least about 120, at least about 140, at least about 160, at least about 180, or about 200 amino acids, preferably continuous amino acids. Regarding CLDN6 polypeptide variants, the degree of similarity or identity is given preferably for a region of at least about 100, at least about 120, at least about 140, at least about 160, at least about 180, at least about 200, or at least about 210 amino acids. In preferred embodiments, the degree of similarity or identity is given for the entire length of the reference amino acid sequence such as the amino acid sequences given in the sequence listing. The alignment for determining sequence similarity, preferably sequence identity can be done with art known tools, preferably using the best sequence alignment, for example, using Align, using standard settings, preferably EMBOSS::needle, Matrix: Blosum62, Gap Open 10.0, Gap Extend 0.5.

"Sequence similarity" indicates the percentage of amino acids that either are identical or that represent conservative amino acid substitutions. "Sequence identity" between two polypeptide or nucleic acid sequences indicates the percentage of amino acids or nucleotides that are identical between the sequences.

The "percentage identity" is obtained after the best alignment, this percentage being purely statistical and the differences between the two sequences being distributed randomly and over their entire length. Sequence comparisons between two nucleotide or amino acid sequences are conventionally carried out by comparing these sequences after having aligned them optimally, said comparison being carried out by segment or by "window of comparison" in order to identify and compare local regions of sequence similarity. The optimal alignment of the sequences for comparison may be produced, besides manually, by means of the local homology algorithm of Smith and Waterman, 1981, Ads App. Math. 2, 482, by means of the local homology algorithm of Neddleman and Wunsch, 1970, J. Mol. Biol. 48, 443, by means of the similarity search method of Pearson and Lipman, 1988, Proc. Natl Acad. Sci. USA 85, 2444, or by means of computer programs which use these algorithms (GAP, BESTFIT, FASTA, BLAST P, BLAST N and TFASTA in Wisconsin Genetics Software Package, Genetics Computer Group, 575 Science Drive, Madison, Wis.).

The percentage identity is calculated by determining the number of identical positions between the two sequences being compared, dividing this number by the number of positions compared and multiplying the result obtained by 100 so as to obtain the percentage identity between these two sequences.

"Conservative substitutions," may be made, for instance, on the basis of similarity in polarity, charge, solubility, hydrophobicity, hydrophilicity, and/or the amphipathic nature of the residues involved. For example: (a) nonpolar (hydrophobic) amino acids include alanine, leucine, isoleucine, valine, proline, phenylalanine, tryptophan, and methionine; (b) polar neutral amino acids include glycine, serine, threonine, cysteine, tyrosine, asparagine, and glutamine; (c) positively charged (basic) amino acids include arginine, lysine, and histidine; and (d) negatively charged (acidic) amino acids include aspartic acid and glutamic acid. Substitutions typically may be made within groups (a)-(d). In addition, glycine and proline may be substituted for one another based on their ability to disrupt α-helices. Some preferred substitutions may be made among the following groups: (i) S and T; (ii) P and G; and (iii) A, V, L and I. Given the known genetic code, and recombinant and synthetic DNA techniques, the skilled scientist readily can construct DNAs encoding the conservative amino acid variants.

The present invention comprises antibodies in which alterations have been made in the Fc region in order to change the functional or pharmacokinetic properties of the antibodies. Such alterations may result in a decrease or increase of C1q binding and CDC or of FcγR binding and ADCC. Substitutions can, for example, be made in one or more of the amino acid residues of the heavy chain constant region, thereby causing an alteration in an effector function while retaining the ability to bind to the antigen as compared with the modified antibody, cf. U.S. Pat. Nos. 5,624,821 and 5,648,260.

The in vivo half-life of antibodies can be improved by modifying the salvage receptor epitope of the Ig constant domain or an Ig-like constant domain such that the molecule does not comprise an intact CH2 domain or an intact Ig Fc region, cf. U.S. Pat. Nos. 6,121,022 and 6,194,551. The in vivo half-life can furthermore be increased by making mutations in the Fc region, e.g., by substituting threonine for leucine at position 252, by substituting threonine for serine at position 254, or by substituting threonine for phenylalanine at position 256, cf. U.S. Pat. No. 6,277,375.

Furthermore, the glycosylation pattern of antibodies can be modified in order to change the effector function of the antibodies. For example, the antibodies can be expressed in a transfectoma which does not add the fucose unit normally attached to Asn at position 297 of the Fc region in order to enhance the affinity of the Fc region for Fc-Receptors which, in turn, will result in an increased ADCC of the antibodies in the presence of NK cells, cf. Shield et al. (2002) JBC, 277: 26733. Furthermore, modification of galactosylation can be made in order to modify CDC.

Alternatively, in another embodiment, mutations can be introduced randomly along all or part of a anti-CLDN6 antibody coding sequence, such as by saturation mutagenesis, and the resulting modified anti-CLDN6 antibodies can be screened for binding activity.

According to the invention the term "cell" or "host cell" preferably relates to an intact cell, i.e. a cell with an intact membrane that has not released its normal intracellular components such as enzymes, organelles, or genetic material. An intact cell preferably is a viable cell, i.e. a living cell capable of carrying out its normal metabolic functions. Preferably said term relates according to the invention to any cell which can be transformed or transfected with an exogenous nucleic acid. The term "cell" includes according to the invention prokaryotic cells (e.g., E. coli) or eukaryotic cells (e.g., dendritic cells, B cells, CHO cells, COS cells, K562 cells, HEK293 cells, HELA cells, yeast cells, and insect cells). The exogenous nucleic acid may be found inside the cell (i) freely dispersed as such, (ii) incorporated in a recombinant vector, or (iii) integrated into the host cell genome or mitochondrial DNA. Mammalian cells are particularly preferred, such as cells from humans, mice, hamsters, pigs, goats, and primates. The cells may be derived from a large number of tissue types and include primary cells and cell lines. Specific examples include keratinocytes, peripheral blood leukocytes, bone marrow stem cells, and embryonic stem cells. In further embodiments, the cell is an antigen-presenting cell, in particular a dendritic cell, a monocyte, or macrophage. The term "host cell", as used herein, preferably is intended to refer to a cell into which a recombinant expression vector has been introduced.

A cell which comprises a nucleic acid molecule preferably express the peptide or protein encoded by the nucleic acid.

The terms "transgenic animal" refers to an animal having a genome comprising one or more transgenes, preferably heavy and/or light chain transgenes, or transchromosomes (either integrated or non-integrated into the animal's natural genomic DNA) and which is preferably capable of expressing the transgenes. For example, a transgenic mouse can have a human light chain transgene and either a human heavy chain transgene or human heavy chain transchromosome, such that the mouse produces human anti-CLDN6 antibodies when immunized with CLDN6 antigen and/or cells expressing CLDN6. The human heavy chain transgene can be integrated into the chromosomal DNA of the mouse, as is the case for transgenic mice, e.g., HuMAb mice, such as HCo7 or HCol2 mice, or the human heavy chain transgene can be maintained extrachromosomally, as is the case for transchromosomal (e.g., KM) mice as described in WO 02/43478. Such transgenic and transchromosomal mice may be capable of producing multiple isotypes of human monoclonal antibodies to CLDN6 (e.g., IgG, IgA and/or IgE) by undergoing V-D-J recombination and isotype switching.

"Reduce" or "inhibit" as used herein means the ability to cause an overall decrease, preferably of 5% or greater, 10% or greater, 20% or greater, more preferably of 50% or greater, and most preferably of 75% or greater, in the level, e.g. in the level of proliferation of cells. The term "inhibit" or similar phrases includes a complete or essentially complete inhibition, i.e. a reduction to zero or essentially to zero.

Terms such as "increasing" or "enhancing" preferably relate to an increase or enhancement by about at least 10%, preferably at least 20%, preferably at least 30%, more preferably at least 40%, more preferably at least 50%, even more preferably at least 80%, and most preferably at least 100%. These terms may also relate to circumstances, wherein at time zero there is no detectable signal for a certain compound or condition and at a particular time point later than time zero there is a detectable signal for a certain compound or condition.

The term "immunologically equivalent" means that the immunologically equivalent molecule such as the immunologically equivalent amino acid sequence exhibits the same or essentially the same immunological properties and/or exerts the same or essentially the same immunological effects, e.g., with respect to the type of the immunological effect such as induction of a humoral and/or cellular immune response, the strength and/or duration of the induced immune reaction, or the specificity of the induced immune reaction. In the context of the present invention, the term "immunologically equivalent" is preferably used with respect to the immunological effects or properties of a peptide or peptide variant used for immunization. A particular immunological property is the ability to bind to antibodies and, where appropriate, generate an immune response, preferably by stimulating the generation of antibodies. For example, an amino acid sequence is immunologically equivalent to a reference amino acid sequence if said amino acid sequence when exposed to the immune system of a subject induces an immune reaction, preferably antibodies, having a specificity of reacting with the reference amino acid sequence, such as the reference amino acid sequence forming part of CLDN6.

The term "immune effector functions" in the context of the present invention includes any functions mediated by components of the immune system that result in the inhibition of tumor growth and/or inhibition of tumor development, including inhibition of tumor dissemination and metastasis. Preferably, immune effector functions result in killing of tumor cells. Preferably, the immune effector functions in the context of the present invention are antibody-mediated effector functions. Such functions comprise complement dependent cytotoxicity (CDC), antibody-dependent cell-mediated cytotoxicity (ADCC), induction of apoptosis in the cells carrying the tumor-associated antigen, for example, by binding of the antibody to a surface antigen, and/or inhibition of proliferation of the cells carrying the tumor-associated antigen, preferably ADCC and/or CDC. Thus, antibodies that are capable of mediating one or more immune effector functions are preferably able to mediate killing of cells by inducing CDC-mediated lysis, ADCC-mediated lysis, apoptosis, homotypic adhesion, and/or phagocytosis, preferably by inducing CDC-mediated lysis and/or ADCC-mediated lysis. Antibodies may also exert an effect simply by binding to tumor-associated antigens on the surface of a tumor cell. For example, antibodies may block the function of the tumor-associated antigen or induce apoptosis just by binding to the tumor-associated antigen on the surface of a tumor cell.

DETAILED DESCRIPTION OF THE INVENTION

Mechanisms of mAb Action

Although the following provides considerations regarding the mechanism underlying the therapeutic efficacy of antibodies of the invention it is not to be considered as limiting to the invention in any way.

The antibodies described herein may interact with components of the immune system, preferably through ADCC or CDC. Antibodies of the invention can also be used to target payloads (e.g., radioisotopes, drugs or toxins) to directly kill tumor cells or can be used synergistically with traditional chemotherapeutic agents, attacking tumors through complementary mechanisms of action that may include anti-tumor immune responses that may have been compromised owing to a chemotherapeutic's cytotoxic side effects on T lymphocytes. However, antibodies of the invention may also exert an effect simply by binding to CLDN6 on the cell surface, thus, e.g. blocking proliferation of the cells.

Antibody-Dependent Cell-Mediated Cytotoxicity

ADCC describes the cell-killing ability of effector cells as described herein, in particular lymphocytes, which preferably requires the target cell being marked by an antibody.

ADCC preferably occurs when antibodies bind to antigens on tumor cells and the antibody Fc domains engage Fc receptors (FcR) on the surface of immune effector cells. Several families of Fc receptors have been identified, and specific cell populations characteristically express defined Fc receptors. ADCC can be viewed as a mechanism to directly induce a variable degree of immediate tumor destruction that leads to antigen presentation and the induction of tumor-directed T-cell responses. Preferably, in vivo induction of ADCC will lead to tumor-directed T-cell responses and host-derived antibody responses.

Complement-Dependent Cytotoxicity

CDC is another cell-killing method that can be directed by antibodies. IgM is the most effective isotype for complement activation. IgG1 and IgG3 are also both very effective at directing CDC via the classical complement-activation pathway. Preferably, in this cascade, the formation of antigen-antibody complexes results in the uncloaking of multiple C1q binding sites in close proximity on the $C_H2$ domains of participating antibody molecules such as IgG molecules (C1q is one of three subcomponents of complement C1). Preferably these uncloaked C1q binding sites convert the previously low-affinity C1q-IgG interaction to one of high avidity, which triggers a cascade of events involving a series of other complement proteins and leads to the proteolytic release of the effector-cell chemotactic/activating agents C3a and C5a. Preferably, the complement cascade ends in the formation of a membrane attack complex, which creates pores in the cell membrane that facilitate free passage of water and solutes into and out of the cell.

Production of Antibodies

Antibodies of the invention can be produced by a variety of techniques, including conventional monoclonal antibody methodology, e.g., the standard somatic cell hybridization technique of Kohler and Milstein, Nature 256: 495 (1975). Although somatic cell hybridization procedures are preferred, in principle, other techniques for producing monoclonal antibodies can be employed, e.g., viral or oncogenic transformation of B-lymphocytes or phage display techniques using libraries of antibody genes.

The preferred animal system for preparing hybridomas that secrete monoclonal antibodies is the murine system. Hybridoma production in the mouse is a very well established procedure. Immunization protocols and techniques for isolation of immunized splenocytes for fusion are known in the art. Fusion partners (e.g., murine myeloma cells) and fusion procedures are also known.

Other preferred animal systems for preparing hybridomas that secrete monoclonal antibodies are the rat and the rabbit system (e.g. described in Spieker-Polet et al., Proc. Natl. Acad. Sci. U.S.A. 92:9348 (1995), see also Rossi et al., Am. J. Clin. Pathol. 124: 295 (2005)).

In yet another preferred embodiment, human monoclonal antibodies directed against CLDN6 can be generated using transgenic or transchromosomal mice carrying parts of the human immune system rather than the mouse system. These transgenic and transchromosomic mice include mice known as HuMAb mice and KM mice, respectively, and are collectively referred to herein as "transgenic mice." The production of human antibodies in such transgenic mice can be performed as described in detail for CD20 in WO2004 035607

Yet another strategy for generating monoclonal antibodies is to directly isolate genes encoding antibodies from lymphocytes producing antibodies of defined strategy e.g. see Babcock et al., 1996; A novel strategy for generating monoclonal antibodies from single, isolated lymphocytes producing antibodies of defined strategy. For details of recombinant antibody engineering see also Welschof and Kraus, Recombinant antibodes for cancer therapy ISBN-0-89603-918-8 and Benny K. C. Lo Antibody Engineering ISBN 1-58829-092-1.

Immunizations

To generate antibodies to CLDN6, mice can be immunized with carrier-conjugated peptides derived from the CLDN6 sequence, an enriched preparation of recombinantly expressed CLDN6 antigen or fragments thereof and/or cells expressing CLDN6 or fragments thereof, as described. Alternatively, mice can be immunized with DNA encoding full length human CLDN6 or fragments thereof. In the event that immunizations using a purified or enriched preparation of the CLDN6 antigen do not result in antibodies, mice can also be immunized with cells expressing CLDN6, e.g., a cell line, to promote immune responses.

The immune response can be monitored over the course of the immunization protocol with plasma and serum samples being obtained by tail vein or retroorbital bleeds. Mice with sufficient titers of anti-CLDN6 immunoglobulin can be used for fusions. Mice can be boosted intraperitoneally or intravenously with CLDN6 expressing cells 3-5 days before sacrifice and removal of the spleen to increase the rate of specific antibody secreting hybridomas.

Generation of Hybridomas Producing Monoclonal Antibodies

To generate hybridomas producing monoclonal antibodies to CLDN6, cells from lymph nodes or spleens obtained from immunized mice can be isolated and fused to an appropriate immortalized cell line, such as a mouse myeloma cell line. The resulting hybridomas can then be screened for the production of antigen-specific antibodies. Individual wells can then be screened by ELISA for antibody secreting hybridomas. By Immunofluorescence and FACS analysis using CLDN6 expressing cells, antibodies with specificity for CLDN6 can be identified. The antibody secreting hybridomas can be replated, screened again, and if still positive for anti-CLDN6 monoclonal antibodies can be subcloned by limiting dilution. The stable subclones can then be cultured in vitro to generate antibody in tissue culture medium for characterization.

Generation of Transfectomas Producing Monoclonal Antibodies

Antibodies of the invention also can be produced in a host cell transfectoma using, for example, a combination of recombinant DNA techniques and gene transfection methods as are well known in the art (Morrison, S. (1985) Science 229: 1202).

For example, in one embodiment, the gene(s) of interest, e.g., antibody genes, can be ligated into an expression vector such as a eukaryotic expression plasmid such as used by the GS gene expression system disclosed in WO 87/04462, WO 89/01036 and EP 338 841 or other expression systems well known in the art. The purified plasmid with the cloned antibody genes can be introduced in eukaryotic host cells such as CHO cells, NS/0 cells, HEK293T cells or HEK293 cells or alternatively other eukaryotic cells like plant derived cells, fungal or yeast cells. The method used to introduce these genes can be methods described in the art such as electroporation, lipofectine, lipofectamine or others. After introduction of these antibody genes in the host cells, cells expressing the antibody can be identified and selected. These cells represent the transfectomas which can then be amplified for their expression level and upscaled to produce antibodies. Recombinant antibodies can be isolated and purified from these culture supernatants and/or cells.

Alternatively, the cloned antibody genes can be expressed in other expression systems, including prokaryotic cells, such as microorganisms, e.g. E. coli. Furthermore, the antibodies can be produced in transgenic non-human animals, such as in milk from sheep and rabbits or in eggs from hens, or in transgenic plants; see e.g. Verma, R., et al. (1998) J. Immunol. Meth. 216: 165-181; Pollock, et al. (1999) J. Immunol. Meth. 231: 147-157; and Fischer, R., et al. (1999) Biol. Chem. 380: 825-839.

Use of Partial Antibody Sequences to Express Intact Antibodies (i.e. Humanization and Chimerization).

a) Chimerization

Murine monoclonal antibodies can be used as therapeutic antibodies in humans when labeled with toxins or radioactive isotopes. Nonlabeled murine antibodies are highly immunogenic in man when repetitively applied leading to reduction of the therapeutic effect. The main immunogenicity is mediated by the heavy chain constant regions. The immunogenicity of murine antibodies in man can be reduced or completely avoided if respective antibodies are chimerized or humanized. Chimeric antibodies are antibodies, the different portions of which are derived from different animal species, such as those having a variable region derived from a murine antibody and a human immunoglobulin constant region. Chimerization of antibodies is achieved by joining of the variable regions of the murine antibody heavy and light chain with the constant region of human heavy and light chain (e.g. as described by Kraus et al., in Methods in Molecular Biology series, Recombinant antibodies for cancer therapy ISBN-0-89603-918-8). In a preferred embodiment chimeric antibodies are generated by joining human kappa-light chain constant region to murine light chain variable region. In an also preferred embodiment chimeric antibodies can be generated by joining human lambda-light chain constant region to murine light chain variable region. The preferred heavy chain constant regions for generation of chimeric antibodies are IgG1, IgG3 and IgG4. Other preferred heavy chain constant regions for generation of chimeric antibodies are IgG2, IgA, IgD and IgM.

b) Humanization

Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al. (1998) Nature 332: 323-327; Jones, P. et al. (1986) Nature 321: 522-525; and Queen, C. et al. (1989) Proc. Natl. Acad. Sci. U.S.A 86: 10029-10033). Such framework sequences can be obtained from public DNA databases that include germline antibody gene sequences. These germline sequences will differ from mature antibody gene sequences because they will not include completely assembled variable genes, which are formed by V (D) J joining during B cell maturation. Germline gene sequences will also differ from the sequences of a high affinity secondary repertoire antibody at individual evenly across the variable region. For example, somatic mutations are relatively infrequent in the amino terminal portion of framework region 1 and in the carboxy-terminal portion of framework region 4. Furthermore, many somatic mutations do not significantly alter the binding properties of the antibody. For this reason, it is not necessary to obtain the entire DNA sequence of a particular antibody in order to recreate an intact recombinant antibody having binding properties similar to those of the original antibody (see WO 99/45962). Partial heavy and light chain sequences spanning the CDR regions are typically sufficient for this purpose. The partial sequence is used to determine which germline variable and joining gene segments contributed to the recombined antibody variable genes. The germline sequence is then used to fill in missing portions of the variable regions. Heavy and light chain leader sequences are cleaved during protein maturation and do not contribute to the properties of the final antibody. To add missing sequences, cloned cDNA sequences can be combined with synthetic oligonucleotides by ligation or PCR amplification. Alternatively, the entire variable region can be synthesized as a set of short, overlapping, oligonucleotides and combined by PCR amplification to create an entirely synthetic variable region clone. This process has certain advantages such as elimination or inclusion or particular restriction sites, or optimization of particular codons.

The nucleotide sequences of heavy and light chain transcripts from hybridomas are used to design an overlapping set of synthetic oligonucleotides to create synthetic V sequences with identical amino acid coding capacities as the natural sequences. The synthetic heavy and kappa chain sequences can differ from the natural sequences in three ways: strings of repeated nucleotide bases are interrupted to facilitate oligonucleotide synthesis and PCR amplification; optimal translation initiation sites are incorporated according to Kozak's rules (Kozak, 1991, J. Biol. Chem. 266: 19867-19870); and HindIII sites are engineered upstream of the translation initiation sites.

For both the heavy and light chain variable regions, the optimized coding and corresponding non-coding, strand sequences are broken down into 30-50 nucleotides approximately at the midpoint of the corresponding non-coding oligonucleotide. Thus, for each chain, the oligonucleotides can be assembled into overlapping double stranded sets that span segments of 150-400 nucleotides. The pools are then used as templates to produce PCR amplification products of 150-400 nucleotides. Typically, a single variable region oligonucleotide set will be broken down into two pools which are separately amplified to generate two overlapping PCR products. These overlapping products are then combined by PCR amplification to form the complete variable region. It may also be desirable to include an overlapping fragment of the heavy or light chain constant region in the PCR amplification to generate fragments that can easily be cloned into the expression vector constructs.

The reconstructed chimerized or humanized heavy and light chain variable regions are then combined with cloned promoter, leader, translation initiation, constant region, 3' untranslated, polyadenylation, and transcription termination sequences to form expression vector constructs. The heavy and light chain expression constructs can be combined into a single vector, co-transfected, serially transfected, or separately transfected into host cells which are then fused to form a host cell expressing both chains. Plasmids for use in construction of expression vectors for human IgGκ are described. The plasmids can be constructed so that PCR amplified V heavy and V kappa light chain cDNA sequences can be used to reconstruct complete heavy and light chain minigenes. These plasmids can be used to express completely human, or chimeric IgG1, Kappa or IgG4, Kappa antibodies. Similar plasmids can be constructed for expression of other heavy chain isotypes, or for expression of antibodies comprising lambda light chains.

Thus, in another aspect of the invention, the structural features of the anti-CLDN6 antibodies of the invention, are used to create structurally related humanized anti-CLDN6 antibodies that retain at least one functional property of the antibodies of the invention, such as binding to CLDN6. More specifically, one or more CDR regions of mouse monoclonal antibodies can be combined recombinantly with known human framework regions and CDRs to create additional, recombinantly-engineered, humanized anti-CLDN6 antibodies of the invention.

Binding to Antigen Expressing Cells

The ability of the antibody to bind CLDN6 can be determined using standard binding assays, such as those set forth in the examples (e.g., ELISA, Western Blot, Immunofluorescence and flow cytometric analysis)

Isolation and Characterization of Antibodies

To purify anti-CLDN6 antibodies, selected hybridomas can be grown in two-liter spinner-flasks for monoclonal antibody purification. Alternatively, anti-CLDN6 antibodies can be produced in dialysis based bioreactors. Supernatants can be filtered and, if necessary, concentrated before affinity chromatography with protein G-sepharose or protein A-sepharose. Eluted IgG can be checked by gel electrophoresis and high performance liquid chromatography to ensure purity. The buffer solution can be exchanged into PBS, and the concentration can be determined by OD280 using 1.43 extinction coefficient. The monoclonal antibodies can be aliquoted and stored at −80° C.

To determine if the selected anti-CLDN6 monoclonal antibodies bind to unique epitopes, site-directed or multi-site directed mutagenesis can be used.

Isotype Determination

To determine the isotype of purified antibodies, isotype ELISAs with various commercial kits (e.g. Zymed, Roche Diagnostics) can be performed. Wells of microtiter plates can be coated with anti-mouse Ig. After blocking, the plates are reacted with monoclonal antibodies or purified isotype controls, at ambient temperature for two hours. The wells can then be reacted with either mouse IgG1, IgG2a, IgG2b or IgG3, IgA or mouse IgM-specific peroxidase-conjugated probes. After washing, the plates can be developed with ABTS substrate (1 mg/ml) and analyzed at OD of 405-650. Alternatively, the IsoStrip Mouse Monoclonal Antibody Isotyping Kit (Roche, Cat. No. 1493027) may be used as described by the manufacturer.

Flow Cytometric Analysis

In order to demonstrate presence of anti-CLDN6 antibodies in sera of immunized mice or binding of monoclonal antibodies to living cells expressing CLDN6, flow cytometry can be used. Cell lines expressing naturally or after transfection CLDN6 and negative controls lacking CLDN6 expression (grown under standard growth conditions) can be mixed with various concentrations of monoclonal antibodies in hybridoma supernatants or in PBS containing 1% FBS, and can be incubated at 4° C. for 30 min. After washing, the APC- or Alexa647-labeled anti IgG antibody can bind to CLDN6-bound monoclonal antibody under the same conditions as the primary antibody staining. The samples can be analyzed by flow cytometry with a FACS instrument using light and side scatter properties to gate on single, living cells. In order to distinguish CLDN6-specific monoclonal antibodies from non-specific binders in a single measurement, the method of co-transfection can be employed. Cells transiently transfected with plasmids encoding CLDN6 and a fluorescent marker can be stained as described above. Transfected cells can be detected in a different fluorescence channel than antibody-stained cells. As the majority of transfected cells express both transgenes, CLDN6-specific monoclonal antibodies bind preferentially to fluorescence marker expressing cells, whereas non-specific antibodies bind in a comparable ratio to non-transfected cells. An alternative assay using fluorescence microscopy may be used in addition to or instead of the flow cytometry assay. Cells can be stained exactly as described above and examined by fluorescence microscopy.

Immunofluorescence Microscopy

In order to demonstrate presence of anti-CLDN6 antibodies in sera of immunized mice or binding of monoclonal antibodies to living cells expressing CLDN6, immunofluorescence microscopy analysis can be used. For example, cell lines expressing either spontaneously or after transfection CLDN6 and negative controls lacking CLDN6 expression are grown in chamber slides under standard growth conditions in DMEM/F12 medium, supplemented with 10% fetal calf serum (FCS), 2 mM L-glutamine, 100 IU/ml penicillin and 100 µg/ml streptomycin. Cells can then be fixed with methanol or paraformaldehyde or left untreated. Cells can then be reacted with monoclonal antibodies against CLDN6 for 30 min. at 25° C. After washing, cells can be reacted with an Alexa555-labelled anti-mouse IgG secondary antibody (Molecular Probes) under the same conditions. Cells can then be examined by fluorescence microscopy.

Total CLDN6 levels in cells can be observed when cells are methanol fixed or paraformaldehyde fixed and permeabilized with Triton X-100. In living cells and non-permeabilized, paraformaldehyde fixed cells surface localization of CLDN6 can be examined. Additionally targeting of CLDN6 to tight junctions can be analyzed by co-staining with tight junction markers such as ZO-1. Furthermore, effects of antibody binding and CLDN6 localization within the cell membrane can be examined.

Western Blot

Anti-CLDN6 IgG can be further tested for reactivity with CLDN6 antigen by Western Blotting. Briefly, cell extracts from cells expressing CLDN6 and appropriate negative controls can be prepared and subjected to sodium dodecyl sulfate (SDS) polyacrylamide gel electrophoresis. After electrophoresis, the separated antigens will be transferred to nitrocellulose membranes, blocked, and probed with the monoclonal antibodies to be tested. IgG binding can be detected using anti-mouse IgG peroxidase and developed with ECL substrate.

Immunohistochemistry

Anti-CLDN6 mouse IgGs can be further tested for reactivity with CLDN6 antigen by Immunohistochemistry in a manner well known to the skilled person, e.g. using paraformaldehyde or acetone fixed cryosections or paraffin embedded tissue sections fixed with paraformaldehyde from non-cancer tissue or cancer tissue samples obtained from patients during routine surgical procedures or from mice carrying xenografted tumors inoculated with cell lines expressing spontaneously or after transfection CLDN6. For immunostaining, antibodies reactive to CLDN6 can be incubated followed by horseradish-peroxidase conjugated goat anti-mouse or goat anti-rabbit antibodies (DAKO) according to the vendor's instructions.

Phagocytic and Cell Killing Activities of Antibodies In Vitro

In addition to binding specifically to CLDN6, anti-CLDN6 antibodies can be tested for their ability to mediate phagocytosis and killing of cells expressing CLDN6 and being characterized by association of CLDN6 with their cell surface. The testing of monoclonal antibody activity in vitro will provide an initial screening prior to testing in vivo models.

Antibody Dependent Cell-Mediated Cytotoxicity (ADCC):

Briefly, polymorphonuclear cells (PMNs), NK cells, monocytes, mononuclear cells or other effector cells, from healthy donors can be purified by Ficoll Hypaque density centrifugation, followed by lysis of contaminating erythrocytes. Washed effector cells can be suspended in RPMI supplemented with 10% heat-inactivated fetal calf serum or, alternatively with 5% heat-inactivated human serum and mixed with $^{51}$Cr labeled target cells expressing CLDN6 and being characterized by association of CLDN6 with their cell surface, at various ratios of effector cells to target cells. Alternatively, the target cells may be labeled with a fluorescence enhancing ligand (BATDA). A highly fluorescent chelate of Europium with the enhancing ligand which is released from dead cells can be measured by a fluorometer. Another alternative technique may utilize the transfection of target cells with luciferase. Added lucifer yellow may then be oxidated by viable cells only. Purified anti-CLDN6 IgGs can then be added at various concentrations. Irrelevant human IgG can be used as negative control. Assays can be carried out for 4 to 20 hours at 37° C. depending on the effector cell type used. Samples can be assayed for cytolysis by measuring $^{51}$Cr release or the presence of the EuTDA chelate in the culture supernatant. Alternatively, luminescence resulting from the oxidation of lucifer yellow can be a measure of viable cells.

Anti-CLDN6 monoclonal antibodies can also be tested in various combinations to determine whether cytolysis is enhanced with multiple monoclonal antibodies.

Complement Dependent Cytotoxicity (CDC):

Monoclonal anti-CLDN6 antibodies can be tested for their ability to mediate CDC using a variety of known techniques. For example, serum for complement can be obtained from blood in a manner known to the skilled person. To determine the CDC activity of mAbs, different methods can be used. $^{51}$Cr release can for example be measured or elevated membrane permeability can be assessed using a propidium iodide (PI) exclusion assay. Briefly, target cells can be washed and $5\times10^5$/ml can be incubated with various concentrations of mAb for 10-30 min. at room temperature or at 37° C. Serum or plasma can then be added to a final concentration of 20% (v/v) and the cells incubated at 37° C. for 20-30 min. All cells from each sample can be added to the PI solution in a FACS tube. The mixture can then be analyzed immediately by flow cytometry analysis using FACSArray.

In an alternative assay, induction of CDC can be determined on adherent cells. In one embodiment of this assay, cells are seeded 24 h before the assay with a density of $3\times10^4$/well in tissue-culture flat-bottom microtiter plates. The next day growth medium is removed and the cells are incubated in triplicates with antibodies. Control cells are incubated with growth medium or growth medium containing 0.2% saponin for the determination of background lysis and maximal lysis, respectively. After incubation for 20 min. at room temperature supernatant is removed and 20% (v/v) human plasma or serum in DMEM (prewarmed to 37° C.) is added to the cells and incubated for another 20 min. at 37° C. All cells from each sample are added to propidium iodide solution (10 μg/ml). Then, supernatants are replaced by PBS containing 2.5 μg/ml ethidium bromide and fluorescence emission upon excitation at 520 nm is measured at 600 nm using a Tecan Safire. The percentage specific lysis is calculated as follows: % specific lysis=(fluorescence sample-fluorescence background)/(fluorescence maximal lysis-fluorescence background)×100.

Inhibition of Cell Proliferation by Monoclonal Antibodies:

To test for the ability to initiate apoptosis, monoclonal anti-CLDN6 antibodies can, for example, be incubated with CLDN6 positive tumor cells or CLDN6 transfected tumor cells at 37° C. for about 20 hours. The cells can be harvested, washed in Annexin-V binding buffer (BD biosciences), and incubated with Annexin V conjugated with FITC or APC (BD biosciences) for 15 min. in the dark. All cells from each sample can be added to PI solution (10 μg/ml in PBS) in a FACS tube and assessed immediately by flow cytometry (as above). Alternatively, a general inhibition of cell-proliferation by monoclonal antibodies can be detected with commercially available kits. The DELFIA Cell Proliferation Kit (Perkin-Elmer, Cat. No. AD0200) is a non-isotopic immunoassay based on the measurement of 5-bromo-2'-deoxyuridine (BrdU) incorporation during DNA synthesis of proliferating cells in microplates. Incorporated BrdU is detected using europium labelled monoclonal antibody. To allow antibody detection, cells are fixed and DNA denatured using Fix solution. Unbound antibody is washed away and DELFIA inducer is added to dissociate europium ions from the labelled antibody into solution, where they form highly fluorescent chelates with components of the DELFIA Inducer. The fluorescence measured—utilizing time-resolved fluorometry in the detection—is proportional to the DNA synthesis in the cell of each well.

Preclinical Studies

Monoclonal antibodies which bind to CLDN6 also can be tested in an in vivo model (e.g. in immune deficient mice carrying xenografted tumors inoculated with cell lines expressing CLDN6, possibly after transfection) to determine their efficacy in controlling growth of CLDN6-expressing tumor cells.

In vivo studies after xenografting CLDN6 expressing tumor cells into immunocompromised mice or other animals can be performed using antibodies of the invention. Antibodies can be adminstered to tumor free mice followed by injection of tumor cells to measure the effects of the antibodies to prevent formation of tumors or tumor-related symptoms. Antibodies can be adminstered to tumor-bearing mice to determine the therapeutic efficacy of respective antibodies to reduce tumor growth, metastasis or tumor related symptoms. Antibody application can be combined with application of other substances as cystostatic drugs, growth factor inhibitors, cell cycle blockers, angiogenesis inhibitors or other antibodies to determine synergistic efficacy and potential toxicity of combinations. To analyze toxic side effects mediated by antibodies of the invention animals can be inoculated with antibodies or control reagents and thoroughly investigated for symptoms possibly related to CLDN6-antibody therapy. Possible side effects of in vivo application of CLDN6 antibodies particularly include toxicity at CLDN6 expressing tissues including placenta. Antibodies recognizing CLDN6 in human and in other species, e.g. mice, are particularly useful to predict potential side effects mediated by application of monoclonal CLDN6 antibodies in humans.

Epitope Mapping

Mapping of epitopes recognized by antibodies of invention can be performed as described in detail in "Epitope Mapping Protocols (Methods in Molecular Biology) by Glenn E. Morris ISBN-089603-375-9 and in "Epitope Mapping: A Practical Approach" Practical Approach Series, 248 by Olwyn M. R. Westwood, Frank C. Hay.

I. Bispecific/Multispecific Molecules which Bind to CLDN6

In yet another embodiment of the invention, antibodies to CLDN6 can be derivatized or linked to another functional molecule, e.g., another peptide or protein (e.g., an Fab' fragment) to generate a bispecific or multispecific molecule which binds to multiple binding sites or target epitopes. For example, an antibody of the invention can be functionally linked (e.g. by chemical coupling, genetic fusion, noncovalent association or otherwise) to one or more other binding molecules, such as another antibody, peptide or binding mimetic.

Accordingly, the present invention includes bispecific and multispecific molecules comprising at least one first binding specificity for CLDN6 and a second binding specificity for a second target epitope. In a particular embodiment of the invention, the second target epitope is an Fc receptor, e.g. human Fc-gammaRI (CD64) or a human Fc-alpha receptor (CD89), or a T cell receptor, e.g. CD3. Therefore, the invention includes bispecific and multispecific molecules capable of binding both to Fc-gammaR, Fc-alphaR or Fc-epsilonR expressing effector cells (e.g. monocytes, macrophagesor polymorphonuclear cells (PMNs)), and to target cells expressing CLDN6 and being characterized by association of CLDN6 with their cell surface. These bispecific and multispecific molecules may target cells expressing CLDN6 and being characterized by association of CLDN6 with their cell surface to effector cells and may trigger Fc receptor-mediated effector cell activities, such as phagocytosis of cells expressing CLDN6 and being characterized by association of CLDN6 with their cell surface, antibody dependent cellular cytotoxicity (ADCC), cytokine release, or generation of superoxide anion.

Bispecific and multispecific molecules of the invention can further include a third binding specificity, in addition to an anti-Fc binding specificity and an anti-CLDN6 binding specificity. In one embodiment, the third binding specificity is an anti-enhancement factor (EF) portion, e.g. a molecule which binds to a surface protein involved in cytotoxic activity and thereby increases the immune response against the target cell. The "anti-enhancement factor portion" can be an antibody, functional antibody fragment or a ligand that binds to a given molecule, e.g., an antigen or a receptor, and thereby results in an enhancement of the effect of the binding determinants for the Fc receptor or target cell antigen. The "anti-enhancement factor portion" can bind an Fc receptor or a target cell antigen. Alternatively, the anti-enhancement factor portion can bind to an entity that is different from the entity to which the first and second binding specificities bind. For example, the anti-enhancement factor portion can bind a cytotoxic T cell (e.g., via CD2, CD3, CD8, CD28, CD4, CD40, ICAM-1 or other immune cell that results in an increased immune response against the target cell).

In one embodiment, the bispecific and multispecific molecules of the invention comprise as a binding specificity at least one antibody, including, e.g., an Fab, Fab', F(ab')$_2$, Fv, or a single chain Fv. The antibody may also be a light chain or heavy chain dimer, or any minimal fragment thereof such as a Fv or a single chain construct as described in Ladner et al., U.S. Pat. No. 4,946,778. The antibody may also be a binding-domain immunoglobulin fusion protein as disclosed in US2003/0118592 and US 2003/0133939.

In one embodiment bispecific and multispecific molecules of the invention comprise a binding specificity for an Fc-gammaR or an Fc-alphaR present on the surface of an effector cell, and a second binding specificity for a target cell antigen, e.g., CLDN6.

In one embodiment, the binding specificity for an Fc receptor is provided by a monoclonal antibody, the binding of which is not blocked by human immunoglobulin G (IgG). As used herein, the term "IgG receptor" refers to any of the eight gamma-chain genes located on chromosome 1. These genes encode a total of twelve transmembrane or soluble receptor isoforms which are grouped into three Fc-gamma receptor classes: Fc-gammaRI (CD64), Fc-gammaRII (CD32), and Fc-gammaRIII (CD16). In one preferred embodiment, the Fc-gamma receptor is a human high affinity Fc-gammaRI.

In still other preferred embodiments, the binding specificity for an Fc receptor is provided by an antibody that binds to a human IgA receptor, e.g., an Fc-alpha receptor (Fc-alphaRI (CD89)), the binding of which is preferably not blocked by human immunoglobulin A (IgA). The term "IgA receptor" is intended to include the gene product of one alpha-gene (Fc-alphaRI) located on chromosome 19. This gene is known to encode several alternatively spliced transmembrane isoforms of 55 to 110 kDa. Fc-alphaRI (CD89) is constitutively expressed on monocytes/macrophages, eosinophilic and neutrophilic granulocytes, but not on non-effector cell populations. Fc-alphaRI has medium affinity for both IgA1 and IgA2, which is increased upon exposure to cytokines such as G-CSF or GM-CSF (Morton, H. C. et al. (1996) Critical Reviews in Immunology 16: 423-440). Four Fc-alphaRI-specific monoclonal antibodies, identified as A3, A59, A62 and A77, which bind Fc-alphaRI outside the IgA ligand binding domain, have been described (Monteiro, R. C. et al. (1992) J. Immunol. 148: 1764).

In another embodiment the bispecific molecule is comprised of two monoclonal antibodies according to the invention which have complementary functional activities, such as one antibody predominately working by inducing CDC and the other antibody predominately working by inducing apoptosis.

An "effector cell specific antibody" as used herein refers to an antibody or functional antibody fragment that binds the Fc receptor of effector cells. Preferred antibodies for use in the subject invention bind the Fc receptor of effector cells at a site which is not bound by endogenous immunoglobulin.

As used herein, the term "effector cell" refers to an immune cell which is involved in the effector phase of an immune response, as opposed to the cognitive and activation phases of an immune response. Exemplary immune cells include cells of myeloid or lymphoid origin, e.g, lymphocytes (e.g., B cells and T cells including cytolytic T cells (CTLs), killer cells, natural killer cells, macrophages, monocytes, eosinophils, neutrophils, polymorphonuclear cells, granulocytes, mast cells, and basophils. Some effector cells express specific Fc receptors and carry out specific immune functions. In preferred embodiments, an effector cell is capable of inducing antibody-dependent cellular cytotoxicity (ADCC), e.g., a neutrophil capable of inducing ADCC. For example, monocytes, macrophages, which express FcR are involved in specific killing of target cells and presenting antigens to other components of the immune system, or binding to cells that present antigens. In other embodiments, an effector cell can phagocytose a target antigen, target cell, or microorganism. The expression of a particular FcR on an effector cell can be regulated by humoral factors such as cytokines. For example, expression of Fc-gammaRI has been found to be up-regulated by interferon gamma (IFN-γ). This enhanced expression increases the cytotoxic activity of Fc-gammaRI-bearing cells against targets. An effector cell can phagocytose or lyse a target antigen or a target cell.

"Target cell" shall mean any undesirable cell in a subject (e.g., a human or animal) that can be targeted by an antibody of the invention. In preferred embodiments, the target cell is a cell expressing or overexpressing CLDN6 and being characterized by association of CLDN6 with its cell surface. Cells expressing CLDN6 and being characterized by association of CLDN6 with their cell surface typically include tumor cells.

II. Immunoconjugates

In another aspect, the present invention features an anti-CLDN6 antibody conjugated to a therapeutic moiety or agent, such as a cytotoxin, a drug (e.g., an immunosuppressant) or a radioisotope. Such conjugates are referred to herein as "immunoconjugates". Immunoconjugates which include one or more cytotoxins are referred to as "immunotoxins". A cytotoxin or cytotoxic agent includes any agent that is detrimental to and, in particular, kills cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

Suitable therapeutic agents for forming immunoconjugates of the invention include, but are not limited to, antimetabolites (e.g., methotrexate, 6-mercaptopurine, 6-thioguanine, cytarabine, fludarabin, 5-fluorouracil decarbazine), alkylating agents (e.g., mechlorethamine, thioepa chlorambucil, melphalan, carmustine (BSNU) and lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC), and anti-mitotic agents (e.g., vincristine and vinblastine). In a preferred embodiment, the therapeutic agent is a cytotoxic agent or a radiotoxic agent. In another embodiment, the therapeutic agent is an immunosuppressant. In yet another embodiment, the therapeutic agent is GM-CSF. In a preferred embodiment, the therapeutic agent is doxorubicin, cisplatin, bleomycin, sulfate, carmustine, chlorambucil, cyclophosphamide or ricin A.

Antibodies of the present invention also can be conjugated to a radioisotope, e.g., iodine-131, yttrium-90 or indium-111, to generate cytotoxic radiopharmaceuticals for treating a CLDN6-related disorder, such as a cancer. The antibody conjugates of the invention can be used to modify a given biological response, and the drug moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, pseudomonas exotoxin, or diphtheria toxin; a protein such as tumor necrosis factor or interferon-γ; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62: 119-58 (1982).

In a further embodiment, the antibodies according to the invention are attached to a linker-chelator, e.g., tiuxetan, which allows for the antibody to be conjugated to a radioisotope.

III. Pharmaceutical Compositions

In another aspect, the present invention provides a composition, e.g., a pharmaceutical composition, containing one or a combination of antibodies of the present invention. The pharmaceutical compositions may be formulated with pharmaceutically acceptable carriers or diluents as well as any other known adjuvants and excipients in accordance with conventional techniques such as those disclosed in Remington: The Science and Practice of Pharmacy, 19th Edition, Gennaro, Ed., Mack Publishing Co., Easton, Pa., 1995. In one embodiment, the compositions include a combination of multiple (e.g., two or more) isolated antibodies of the invention which act by different mechanisms, e.g., one antibody which predominately acts by inducing CDC in combination with another antibody which predominately acts by inducing apoptosis.

Pharmaceutical compositions of the invention also can be administered in combination therapy, i.e., combined with other agents. For example, the combination therapy can include a composition of the present invention with at least one anti-inflammatory agent or at least one immunosuppressive agent. In one embodiment such therapeutic agents include one or more anti-inflammatory agents, such as a steroidal drug or a NSAID (nonsteroidal anti-inflammatory drug). Preferred agents include, for example, aspirin and other salicylates, Cox-2 inhibitors, such as rofecoxib (Vioxx) and celecoxib (Celebrex), NSAIDs such as ibuprofen (Motrin, Advil), fenoprofen (Nalfon), naproxen (Naprosyn), sulindac (Clinoril), diclofenac (Voltaren), piroxicam (Feldene), ketoprofen (Orudis), diflunisal (Dolobid), nabumetone (Relafen), etodolac (Lodine), oxaprozin (Daypro), and indomethacin (Indocin).

In another embodiment, such therapeutic agents include agents leading to the depletion or functional inactivation of regulatory T cells like low dose cyclophosphamid, anti-CTLA4 antibodies, anti-IL2 or anti-IL2-receptor antibodies.

In yet another embodiment, such therapeutic agents include one or more chemotherapeutics, such as Taxol derivatives, taxotere, gemcitabin, 5-Fluoruracil, doxorubicin (Adriamycin), cisplatin (Platinol), cyclophosphamide (Cytoxan, Procytox, Neosar). In another embodiment, antibodies of the present invention may be administered in combination with chemotherapeutic agents, which preferably show therapeutic efficacy in patients suffering from cancer, e.g. cancer types as described herein.

In yet another embodiment, the antibodies of the invention may be administered in conjunction with radiotherapy and/or autologous peripheral stem cell or bone marrow transplantation.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, e.g., antibody, bispecific and multispecific molecule, may be coated in a material to protect the compound from the action of acids and other natural conditions that may inactivate the compound.

A "pharmaceutically acceptable salt" refers to a salt that retains the desired biological activity of the parent compound and does not impart any undesired toxicological effects (see e.g., Berge, S. M., et al. (1977) J. Pharm. Sci. 66: 1-19).

Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A composition of the present invention can be administered by a variety of methods known in the art. As will be appreciated by the skilled artisan, the route and/or mode of administration will vary depending upon the desired results. The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Methods for the preparation of such formulations are generally known to those skilled in the art. See, e.g., Sustained and Controlled Release Drug Delivery Systems, J. R. Robinson, ed., Marcel Dekker, Inc., New York, 1978.

To administer a compound of the invention by certain routes of administration, it may be necessary to coat the compound with, or co-administer the compound with, a material to prevent its inactivation. For example, the compound may be administered to a subject in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan et al. (1984) J. Neuroimmunol. 7: 27).

Pharmaceutically acceptable carriers include sterile aqueous solutions or dispersions and sterile powders for the extemporaneous preparation of sterile injectable solutions or dispersions. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration.

Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

For the therapeutic compositions, formulations of the present invention include those suitable for oral, nasal, topical (including buccal and sublingual), rectal, vaginal and/or parenteral administration. The formulations may conveniently be presented in unit dosage form and may be prepared by any methods known in the art of pharmacy. The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect.

Formulations of the present invention which are suitable for vaginal administration also include pessaries, tampons, creams, gels, pastes, foams or spray formulations containing such carriers as are known in the art to be appropriate. Dosage forms for the topical or transdermal administration of compositions of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the presence of microorganisms may be ensured both by sterilization procedures, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved. In general, a suitable daily dose of a composition of the invention will be that amount of the compound which is the lowest dose effective to produce a therapeutic effect. Such an effective dose will generally depend upon the factors described above. It is preferred that administration be intravenous, intramuscular, intraperitoneal, or subcutaneous, preferably administered proximal to the site of the target. If desired, the effective daily dose of a therapeutic composition may be administered as two, three, four, five, six or more sub-doses administered separately at appropriate intervals throughout the day, optionally, in unit dosage forms. While it is possible for a compound of the present invention to be administered alone, it is preferable to administer the compound as a pharmaceutical formulation (composition).

In one embodiment, the antibodies of the invention may be administered by infusion, preferably slow continuous infusion over a long period, such as more than 24 hours, in order to reduce toxic side effects. The administration may also be performed by continuous infusion over a period of from 2 to 24 hours, such as of from 2 to 12 hours. Such regimen may be repeated one or more times as necessary, for example, after 6 months or 12 months. The dosage can be determined or adjusted by measuring the amount of circulating monoclonal anti-CLDN6 antibodies upon administration in a biological sample by using anti-idiotypic antibodies which target the anti-CLDN6 antibodies.

In yet another embodiment, the antibodies are administered by maintenance therapy, such as, e.g., once a week for a period of 6 months or more.

In still another embodiment, the antibodies according to the invention may be administered by a regimen including one infusion of an antibody against CLDN6 followed by an infusion of an antibody against CLDN6 conjugated to a radioisotope. The regimen may be repeated, e.g., 7 to 9 days later.

In one embodiment of the invention, the therapeutic compounds of the invention are formulated in liposomes. In a more preferred embodiment, the liposomes include a targeting moiety. In a most preferred embodiment, the therapeutic compounds in the liposomes are delivered by bolus injection to a site proximal to the desired area, e.g., the site of a tumor. The composition must be fluid to the extent that easy syringability exists. It must be stable under the conditions of manufacture and storage and must be preserved against the contaminating action of microorganisms such as bacteria and fungi.

In a further embodiment, antibodies of the invention can be formulated to prevent or reduce their transport across the placenta. This can be done by methods known in the art, e.g., by PEGylation of the antibodies or by use of F(ab)2' fragments. Further references can be made to "Cunningham-Rundles C, Zhuo Z, Griffith B, Keenan J. (1992) Biological activities of polyethylene-glycol immunoglobulin conjugates. Resistance to enzymatic degradation. J. Immunol. Methods, 152: 177-190; and to "Landor M. (1995) Maternal-fetal transfer of immunoglobulins, Ann. Allergy Asthma Immunol. 74: 279-283.

A "therapeutically effective dosage" for tumor therapy can be measured by objective tumor responses which can either be complete or partial. A complete response (CR) is defined as no clinical, radiological or other evidence of disease. A partial response (PR) results from a reduction in aggregate tumor size of greater than 50%. Median time to progression is a measure that characterizes the durability of the objective tumor response.

A "therapeutically effective dosage" for tumor therapy can also be measured by its ability to stabilize the progression of disease. The ability of a compound to inhibit cancer can be evaluated in an animal model system predictive of efficacy in human tumors. Alternatively, this property of a composition can be evaluated by examining the ability of the compound to inhibit cell growth or apoptosis by in vitro assays known to the skilled practitioner. A therapeutically effective amount of a therapeutic compound can decrease tumor size, or otherwise ameliorate symptoms in a subject. One of ordinary skill in the art would be able to determine such amounts based on such factors as the subject's size, the severity of the subject's symptoms, and the particular composition or route of administration selected.

The composition must be sterile and fluid to the extent that the composition is deliverable by syringe. In addition to water, the carrier can be an isotonic buffered saline solution, ethanol, polyol (for example, glycerol, propylene glycol, and liquid polyetheylene glycol, and the like), and suitable mixtures thereof. Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition. Long-term absorption of the injectable compositions can be brought about by including in the composition an agent which delays absorption, for example, aluminum monostearate or gelatin.

When the active compound is suitably protected, as described above, the compound may be orally administered, for example, with an inert diluent or an assimilable edible carrier.

IV. Uses and Methods of the Invention

The antibodies (including immunoconjugates, bispecifics/multispecifics, compositions and other derivatives described herein) of the present invention have numerous therapeutic utilities involving the treatment of disorders involving cells expressing CLDN6 and being characterized by association of CLDN6 with their cell surface. For example, the antibodies can be administered to cells in culture, e.g., in vitro or ex vivo, or to human subjects, e.g., in vivo, to treat or prevent a variety of disorders such as those described herein. Preferred subjects include human patients having disorders that can be corrected or ameliorated by killing diseased cells, in particular cells characterized by an altered expression pattern of CLDN6 and/or an altered pattern of association of CLDN6 with their cell surface compared to normal cells.

For example, in one embodiment, antibodies of the present invention can be used to treat a subject with a tumorigenic disorder, e.g., a disorder characterized by the presence of tumor cells expressing CLDN6 and being characterized by association of CLDN6 with their cell surface. Examples of tumorigenic diseases which can be treated and/or prevented encompass all CLDN6 expressing cancers and tumor entities including those described herein.

The pharmaceutical compositions and methods of treatment described according to the invention may also be used for immunization or vaccination to prevent a disease described herein.

In another embodiment, antibodies of the invention can be used to detect levels of CLDN6 or particular forms of CLDN6, or levels of cells which contain CLDN6 on their membrane surface, which levels can then be linked to certain diseases or disease symptoms such as described above. Alternatively, the antibodies can be used to deplete or interact with the function of cells expressing CLDN6 and being characterized by association of CLDN6 with their cell surface, thereby implicating these cells as important mediators of the disease. This can be achieved by contacting a sample and a control sample with the anti-CLDN6 antibody under conditions that allow for the formation of a complex between the antibody and CLDN6. Any complexes formed between the antibody and CLDN6 are detected and compared in the sample and a control sample, i.e. a reference sample.

Antibodies of the invention can be initially tested for their binding activity associated with therapeutic or diagnostic uses in vitro. For example, the antibodies can be tested using flow cytometric assays as described herein.

The antibodies of the invention can be used to elicit in vivo or in vitro one or more of the following biological activities: to inhibit the growth of and/or differentiation of a cell expressing CLDN6 and being characterized by association of CLDN6 with its cell surface; to kill a cell expressing CLDN6 and being characterized by association of CLDN6 with its cell surface; to mediate phagocytosis or ADCC of a cell expressing CLDN6 and being characterized by association of CLDN6 with its cell surface in the presence of effector cells; to mediate CDC of a cell expressing CLDN6 and being characterized by association of CLDN6 with its cell surface in the presence of complement; to mediate apoptosis of a cell expressing CLDN6 and being characterized by association of CLDN6 with its cell surface; to induce homotypic adhesion; and/or to induce translocation into lipid rafts upon binding CLDN6.

In a particular embodiment, the antibodies are used in vivo or in vitro to treat, prevent or diagnose a variety of CLDN6-related diseases. Examples of CLDN6-related diseases include, among others, cancers such as those described herein.

As described above, anti-CLDN6 antibodies of the invention can be co-administered with one or other more therapeutic agents, e.g., a cytotoxic agent, a radiotoxic agent, antiangiogeneic agent or and immunosuppressive agent to reduce the induction of immune responses against the antibodies of invention. The antibody can be linked to the agent (as an immunocomplex) or can be administered separate from the agent. In the latter case (separate administration), the antibody can be administered before, after or concurrently with the agent or can be co-administered with other known therapies, e.g., an anti-cancer therapy, e.g., radiation. Such therapeutic agents include, among others, anti-neoplastic agents such as listed above. Co-administration of the anti-CLDN6 antibodies of the present invention with chemotherapeutic agents provides two anti-cancer agents which operate via different mechanisms yielding a cytotoxic effect to tumor cells. Such co-administration can solve problems due to development of resistance to drugs or a change in the antigenicity of the tumor cells which would render them unreactive with the antibody.

The compositions (e.g., antibodies, multispecific and bispecific molecules and immunoconjugates) of the invention which have complement binding sites, such as portions from IgG1, -2, or -3 or IgM which bind complement, can also be used in the presence of complement. In one embodiment, ex vivo treatment of a population of cells comprising target cells with a binding agent of the invention and appropriate effector cells can be supplemented by the addition of complement or serum containing complement. Phagocytosis of target cells coated with a binding agent of the invention can be improved by binding of complement proteins. In another embodiment target cells coated with the compositions of the invention can also be lysed by complement. In yet another embodiment, the compositions of the invention do not activate complement.

The compositions of the invention can also be administered together with complement. Accordingly, within the scope of the invention are compositions comprising antibodies, multispecific or bispecific molecules and serum or complement. These compositions are advantageous in that the complement is located in close proximity to the antibodies, multispecific or bispecific molecules.

Alternatively, the antibodies, multispecific or bispecific molecules of the invention and the complement or serum can be administered separately. Binding of the compositions of the present invention to target cells may cause translocation of the CLDN6 antigen-antibody complex into lipid rafts of the cell membrane. Such translocation creates a high density of antigen-antibody complexes which may efficiently activate and/or enhance CDC.

Also within the scope of the present invention are kits comprising the antibody compositions of the invention (e.g., antibodies and immunoconjugates) and instructions for use. The kit can further contain one or more additional reagents, such as an immunosuppressive reagent, a cytotoxic agent or a radiotoxic agent, or one or more additional antibodies of the invention (e.g., an antibody having a complementary activity).

Accordingly, patients treated with antibody compositions of the invention can be additionally administered (prior to, simultaneously with, or following administration of a antibody of the invention) with another therapeutic agent, such as a cytotoxic or radiotoxic agent, which enhances or augments the therapeutic effect of the antibodies of the invention.

In other embodiments, the subject can be additionally treated with an agent that modulates, e.g., enhances or inhibits, the expression or activity of Fc-gamma or Fc-alpha receptors by, for example, treating the subject with a cytokine. Preferred cytokines include granulocyte colony-stimulating factor (G-CSF), granulocyte-macrophage colony-stimulating factor (GM-CSF), interferon-γ (IFN-γ), and tumor necrosis factor (TNF). Other important agents for increasing the therapeutic efficacy of the antibodies and pharmaceutical compositions described herein are β-glucans which are homopolysaccharides of branched glucose residues and are produced by a variety of plants and microorganisms, for example, bacteria, algae, fungi, yeast and grains. Fragments of β-glucans produced by organisms may be also be used. Preferably, the β-glucan is a polymer of β(1,3) glucose wherein at least some of the backbone glucose units, e.g. 3-6% of the backbone glucose units, possess branches such as β(1,6) branches.

In a particular embodiment, the invention provides methods for detecting the presence of CLDN6 antigen in a sample, or measuring the amount of CLDN6 antigen, comprising contacting the sample, and a control sample, with an antibody which specifically binds to CLDN6, under conditions that allow for formation of a complex between the antibody or portion thereof and CLDN6. The formation of a complex is then detected, wherein a difference complex formation between the sample compared to the control sample is indicative for the presence of CLDN6 antigen in the sample.

In still another embodiment, the invention provides a method for detecting the presence or quantifying the amount of cells expressing CLDN6 and being characterized by association of CLDN6 with their cell surface in vivo or in vitro. The method comprises (i) administering to a subject a composition of the invention conjugated to a detectable marker; and (ii) exposing the subject to a means for detecting said detectable marker to identify areas containing cells expressing CLDN6 and being characterized by association of CLDN6 with their cell surface.

Methods as described above are useful, in particular, for diagnosing CLDN6-related diseases and/or the localization of CLDN6-related diseases such as cancer diseases. Preferably an amount of CLDN6 in a sample which is higher than the amount of CLDN6 in a control sample is indicative for the presence of a CLDN6-related disease in a subject, in particular a human, from which the sample is derived.

When used in methods as described above, an antibody described herein may be provided with a label that functions to: (i) provide a detectable signal; (ii) interact with a second label to modify the detectable signal provided by the first or second label, e.g. FRET (Fluorescence Resonance Energy Transfer); (iii) affect mobility, e.g. electrophoretic mobility, by charge, hydrophobicity, shape, or other physical parameters, or (iv) provide a capture moiety, e.g., affinity, antibody/antigen, or ionic complexation. Suitable as label are structures, such as fluorescent labels, luminescent labels, chromophore labels, radioisotopic labels, isotopic labels, preferably stable isotopic labels, isobaric labels, enzyme labels, particle labels, in particular metal particle labels, magnetic particle labels, polymer particle labels, small organic molecules such as biotin, ligands of receptors or binding molecules such as cell adhesion proteins or lectins, label-sequences comprising nucleic acids and/or amino acid residues which can be detected by use of binding agents, etc. Labels comprise, in a nonlimiting manner, barium sulfate, iocetamic acid, iopanoic acid, calcium ipodate, sodium diatrizoate, meglumine diatrizoate, metrizamide, sodium tyropanoate and radio diagnostic, including positron emitters such as fluorine-18 and carbon-11, gamma emitters such as iodine-123, technetium-99m, iodine-131 and indium-111, nuclides for nuclear magnetic resonance, such as fluorine and gadolinium.

In yet another embodiment immunoconjugates of the invention can be used to target compounds (e.g., therapeutic agents, labels, cytotoxins, radiotoxins immunosuppressants, etc.) to cells which have CLDN6 associated with their surface by linking such compounds to the antibody. Thus, the invention also provides methods for localizing ex vivo or in vitro cells expressing CLDN6 and being characterized by association of CLDN6 with their cell surface, such as circulating tumor cells.

The present invention is further illustrated by the following examples which are not be construed as limiting the scope of the invention.

EXAMPLES

The techniques and methods used herein are described herein or carried out in a manner known per se and as described, for example, in Sambrook et al., Molecular Cloning: A Laboratory Manual, 2nd Edition (1989) Cold Spring Harbor Laboratory Press, Cold Spring Harbor, N.Y. All methods including the use of kits and reagents are carried out according to the manufacturer's information unless specifically indicated.

Example 1: Quantification of CLDN6 Expression in Normal Tissues, Cancerous Tissues and Cell Lines Using Real-Time RT-PCR Total cellular RNA was extracted from frozen tissue specimens and cancer cell lines using RNeasy Mini Kit (Qiagen), primed with a $dT_{18}$ oligonucleotide and reverse-transcribed with Superscript II (GIBCO/Lifetech) according to the manufacturer's instructions. Integrity of the obtained cDNA was tested by amplification of p53 transcripts in a 30 cycle PCR. After normalization to HPRT expression of CLDN6 was quantified using ΔΔCT calculation.

Tissues from three individuals were tested for each normal tissue type. Only trace amounts of CLDN6 transcripts could be detected in normal tissues after 40 cycles of RT-PCR. The only normal tissue slightly exceeding the expression cutoff was placenta.

In contrast to normal tissues, we found high expression of CLDN6 in samples from ovarian cancer (adenocarcinomas), lung cancer (NSCLC, with highest frequency and expression levels in adenocarcinomas), gastric cancer, breast cancer, hepatic cancer, pancreatic cancer, skin cancer (basal cell carcinoma and squamous cell carcinoma), malignant melanoma, head and neck cancer (malignant pleomorphic adenoma), sarcoma (synovial sarcoma and carcinosarcoma), bile duct cancer, renal cell cancer (clear cell carcinoma and papillary carcinoma), uterine cancer and cancer cell lines A2780 (ovarian cancer), NIH-OVCAR3 (ovarian cancer), HCT-116 (colon cancer), EFO-27 (ovarian cancer), CPC-N (SCLC), NCI-H552 (NSCLC), SNU-1 (gastric cancer), KATOIII (gastric cancer), YAPC (pancreatic cancer), AGS (gastric cancer), FU97 (gastric cancer), MKN7 (gastric cancer).

Example 2: Quantification of CLDN6 Expression in Normal Tissues, Cancerous Tissues and Cell Lines Using Western Blot Analysis For Western blot analysis 20 µg of total protein extracted from cells lyzed with Laemmli-lysis buffer was used. Extracts were diluted in reducing sample buffer (Roth), subjected to SDS-PAGE and subsequently electrotransferred onto PVDF membrane (Pall). Immunostaining was performed with polyclonal antibodies reactive to CLDN6 (ARP) and beta-Actin (Abcam) followed by detection of primary antibodies with horseradish-peroxidase conjugated goat anti-mouse and goat anti-rabbit secondary antibodies (Dako).

Tissue lysates from up to five individuals were tested for each normal tissue type. No CLDN6 protein expression was detected in any of the normal tissues analyzed. In contrast to normal tissues, high expression of CLDN6 protein was detected in samples from ovarian cancer and lung cancer. CLDN6 expression was detected in NIH-OVCAR3 (ovarian cancer), MKN7 (gastric cancer), AGS (gastric cancer), CPC-N(SCLC), HCT-116 (colon cancer), FU97 (gastric cancer), NEC8 (testicular embryonal carcinoma), JAR (placental choriocarcinoma), JEG3 (placental choriocarcinoma), BEWO (placental choriocarcinoma), and PA-1 (ovarian teratocarcinoma).

Example 3: Immunohistochemical (IHC) Analysis of CLDN6 Expression in Normal Tissues and Cancerous Tissues Paraffin-embedded tissue sections (4 µm) were incubated for 1 hour at 58° C. on a heating plate (HI 1220, Leica). Paraffin was removed from the sections by incubating the slides in Roticlear (Roth) for 2×10 min at RT. Afterwards the sections were rehydrated in graded alcohol (99%, 2×96%, 80% and 70%, 5 min each). Antigen retrieval was performed by boiling slides at 120° C. (15 psi) for 15 min in 10 mM citrate buffer (pH 6.0)+0.05% Tween-20. Directly after boiling slides were incubated in PBS for 5 min. Endogenous peroxidase activity was blocked with 0.3% hydrogen peroxide in MeOH for 15 min at RT. To avoid non-specific binding the slides were blocked with 10% goat serum in PBS for 30 min at RT. Thereafter, the slides were incubated with CLDN6-specific polyclonal antibody (1 µg/ml) (ARP) overnight at 4° C. On the next day the slides were washed with PBS at RT (3×5 min) and incubated with 100 µl of the secondary antibodies (PowerVision poly HRP-Anti-Rabbit IgG ready-to-use (ImmunoLogic)) for one hour at RT. Afterwards, slides were washed with PBS at RT (3×5 min). Final staining was performed by using the VECTOR Nova-RED Substrate Kit SK-4800 from Vector Laboratories (Burlingame). Sections were counterstained with haematoxylin for 90 sec at RT. After dehydration with graded alcohol (70%, 80%, 2×96% and 99%, 5 min each) and 10 min incubation in xylol slides were mounted with X-tra Kit (Medite Histotechnic).

No CLDN6 protein expression was detectable in normal tissues from lung, ovary, stomach, colon, pancreas, liver, duodenum or kidney. In contrast to normal tissues, strong or at least significant staining was observed on tissue sections from ovarian cancer, lung cancer, skin cancer, pancreatic cancer, gastric cancer, breast cancer, urinary bladder cancer (transitional cell carcinoma), cervical cancer, testicular cancer (seminoma) and uterine cancer. Staining was clearly accentuated at the plasma membrane of the malignant epithelial cell populations, whereas adjacent stromal and non-malignant epithelial cells were negative. These results indicate that CLDN6 protein is localized at the plasma membrane of malignant cells.

Example 4: Generation of Murine Antibodies Against CLDN6 a. Generation of Expression Vectors Encoding Full Length CLDN6 and CLDN6 Fragments A non-natural, codon-optimized DNA sequence (SEQ ID NO: 3) encoding full length CLDN6 (NCBI accession number NP_067018.2, SEQ ID NO: 2) was prepared by chemical synthesis (GENEART AG, Germany) and cloned into the pcDNA3.1/myc-His vector (Invitrogen, USA) yielding the vector p3953. Insertion of a stop codon allowed the expression of CLDN6 protein without being fused to the vector encoded myc-His tag. Expression of CLDN6 was tested by Western blot, flow cytometry and immunofluorescence analyzes using commercially available anti-CLDN6 antibodies (ARP, 01-8865; R&D Systems, MAB3656).

In addition, a codon-optimized DNA sequence (SEQ ID NO: 4) coding for the putative extracellular domain 2 (EC2) fragment of CLDN6 (SEQ ID NO: 6) as a fusion with an N-terminal Ig kappa leader derived signal peptide followed by 4 additional amino acids to ensure a correct signal peptidase cleavage site (SEQ ID NO: 5) was prepared and cloned into the pcDNA3.1/myc-His vector yielding the vector p3974. Prior to immunization, expression of the EC2 fragment was confirmed by immunofluorescence microscopy on transiently transfected and paraformaldehyde (PFA)-fixed CHO-K1 cells using a commercially available anti-myc antibody (Cell Signaling, MAB 2276).

b. Generation of Cell Lines Stably Expressing CLDN6

HEK293 and P3X63Ag8U.1 cell lines stably expressing CLDN6 were generated by standard techniques using the vector p3953.

c. Immunizations

Balb/c mice were immunized with 25 µg of p3974 plasmid DNA together with 4 µl PEI-mannose (PEI-Man; in vivo-jetPEI™-Man from PolyPlus Transfection) (150 mM PEI-Man in $H_2O$ with 5% glucose) by intraperitoneal injection on days 0, 16 and 36. On days 48 and 62 mice were immunized by intraperitoneal injection with P3X63Ag8U.1 myeloma cells transfected with p3953 vector to stably express CLDN6. The cells administered on day 62 had been irradiated with 3000 rad prior to injection. The presence of antibodies directed against CLDN6 in sera of mice was monitored by immunofluorescence microscopy between days 20 and 70 using CHO-K1 cells co-transfected with nucleic acids encoding CLDN6 and GFP. To this end, 24 h following transfection, PFA-fixed or non-fixed cells were incubated with a 1:100 dilution of sera from immunized mice for 45 min at room temperature (RT). Cells were washed, incubated with an Alexa555-labeled anti-mouse Ig antibody (Molecular Probes) and subjected to fluorescence microscopy.

Figure 2A:
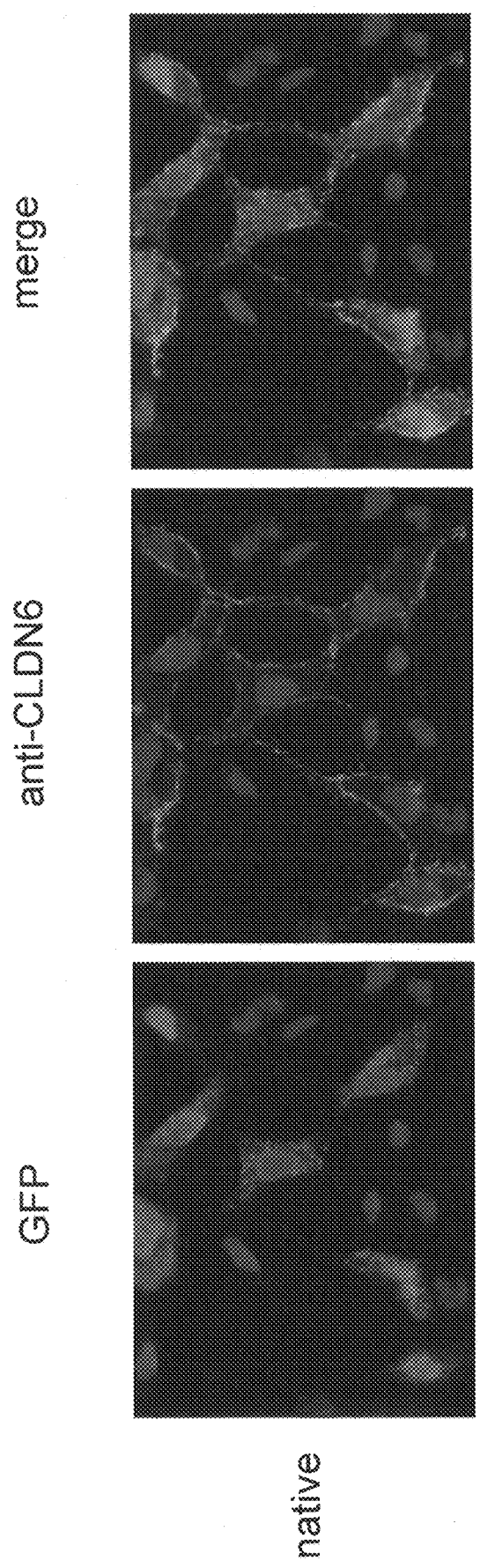
FIG. 2A and FIG. 2B show immunofluorescence analysis of sera obtained from mice immunized to produce CLDN6-specific antibodies.
Figure 2B:
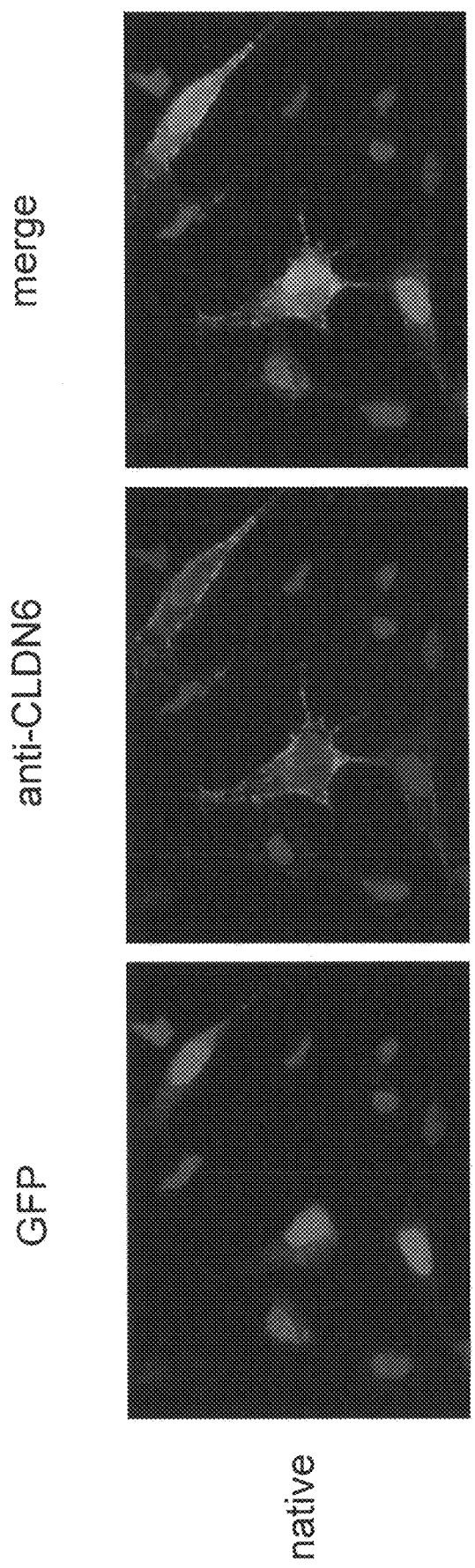

Anti-CLDN6 specific antibodies were detected in serum samples obtained from a mouse on the basis of which the hybridoma F3-6C3-H8 was produced; see FIG. 2.

For generation of monoclonal antibodies, mice with detectable anti-CLDN6 immune responses were boosted four days prior to splenectomy by intraperitonal injection of $2 \times 10^7$ HEK293 cells stably transfected with p3953 vector.

d. Generation of Hybridomas Producing Murine Monoclonal Antibodies Against CLDN6

$6 \times 10^7$ splenocytes isolated from an immunized mouse were fused with $3 \times 10^7$ cells of the mouse myeloma cell line P3X63Ag8.653 (ATCC, CRL 1580) using PEG 1500 (Roche, CRL 10783641001). Cells were seeded at approximately 5×10$^4$ cells per well in flat bottom microtiter plates and cultivated for about two weeks in RPMI selective medium containing 10% heat inactivated fetal bovine serum, 1% hybridoma fusion and cloning supplement (HFCS, Roche, CRL 11363735), 10 mM HEPES, 1 mM sodium pyruvate, 4.5% glucose, 0.1 mM 2-mercaptoethanol, 1× penicillin/streptomycin and 1×HAT supplement (Invitrogen, CRL 21060). After 10 to 14 days, individual wells were screened by flow cytometry for anti-CLDN6 monoclonal antibodies. Antibody secreting hybridomas were subcloned by limiting dilution and again tested for anti-CLDN6 monoclonal antibodies. The stable subclones were cultured to generate small amounts of antibody in tissue culture medium for characterization. At least one clone from each hybridoma which retained the reactivity of the parent cells (tested by flow cytometry) was selected. Nine-vial-cell banks were generated for each clone and stored in liquid nitrogen.

Figure 3:
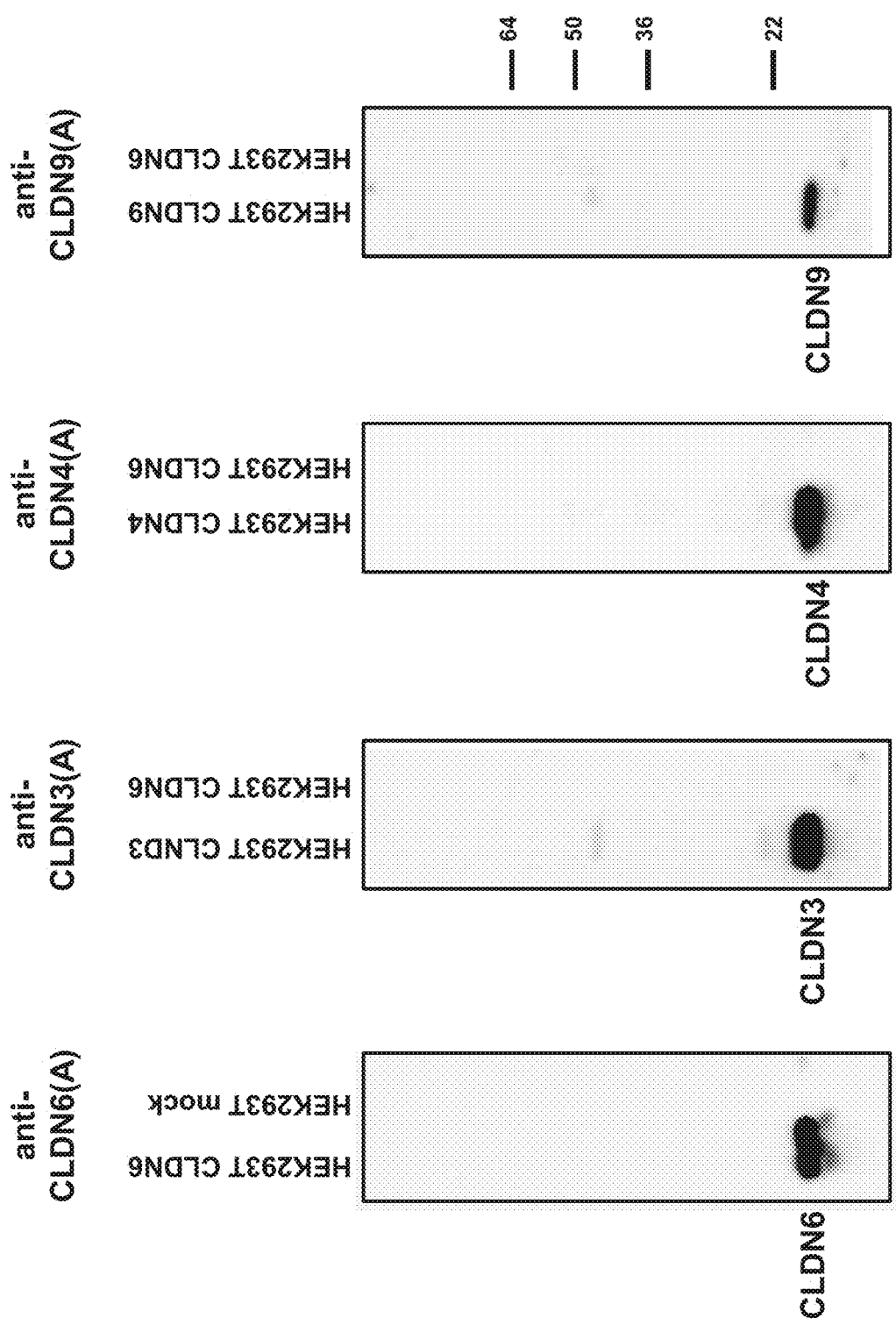
FIG. 3 shows Western blot analysis for assaying endogenous expression of claudin proteins in HEK293T cells.

Example 5: Binding Characteristics of Hybridoma Supernatants and Monoclonal Antibodies a. Quality Control of Transiently Transfected HEK293T Cells by (i) Western Blot and (ii) Flow Cytometry Analyzes (i) HEK293T cells were transfected with nucleic acids encoding CLDN3, CLDN4, CLDN6, and CLDN9, respectively, or mock-transfected. Expression of CLDN3, CLDN4, CLDN6 or CLDN9 in HEK293T cells was determined by Western blotting. To this end, cells were harvested 24 hours post transfection and subjected to lysis. The lysate was subjected to SDS-PAGE, blotted onto nitrocellulose membrane and stained with anti-CLDN3(A) (Invitrogen, 34-1700), anti-CLDN4(A) (Zymed, 32-9400), anti-CDLN6 (A) (ARP, 01-8865) or anti-CLDN9(A) (Santa Cruz, sc-17672) antibodies which specifically bind to the C-terminus of the corresponding claudin under denaturing conditions. Following incubation with a peroxidase-labeled secondary antibody and developing with ECL reagent, a LAS-3000 imager (Fuji) was used for visualization. Bands of the expected molecular weights of CLDN3, CLDN4, CLDN6 and CLDN9, respectively, were observed only in the transfected cells but not in the control cells (FIG. 3) demonstrating that HEK293T cells do not endogenously express any of the claudins investigated and thus, are a suitable tool for determining the cross reactivity of CLDN6 antibodies.

(ii) The HEK293T cells of (i) were further analyzed by flow cytometry using anti-CLDN antibodies recognizing native epitopes (mouse anti-CLDN3 IgG2a (R&D, MAB4620), mouse anti-CLDN4 IgG2a (R&D, MAB4219), mouse anti-CLDN6 IgG2b (R&D, MAB3656)). The antibodies obtainable from Sigma under the product numbers M9144 and M8894 served as isotype controls. Specificity of these anti-CLDN antibodies was analyzed using HEK293T cells transiently transfected with nucleic acids encoding CLDN3, CLDN4, CLDN6, and CLDN9, respectively. The anti-CLDN6 antibody shows cross-reactivity with CLDN3, CLDN4 and CLDN9. The anti-CLDN4 antibody shows cross-reactivity with CLDN3, CLDN6 and CLDN9. The anti-CLDN3 antibody binds specifically to CLDN3 (FIG. 4).

b. Determination of the Specificity of Monoclonal Antibodies Produced According to the Invention Using Flow Cytometry HEK293T cells were co-transfected with a vector encoding different CLDN proteins and a vector encoding a fluorescence marker. 24 h post transfection cells were harvested using 0.05% trypsin/EDTA solution and washed with FACS buffer (PBS containing 2% FCS and 0.1% sodium azide). Cells were transferred into U-bottom microtiter plates at 2×10$^5$ cells per well and incubated for 60 min at 4° C. with hybridoma supernatants. Following washing three times with FACS buffer, cells were incubated with an allophycocyanin (APC)-conjugated anti-mouse IgG 1+2a+2b+3 specific secondary antibody (Dianova, 115-135-164). Thereafter, cells were washed twice and binding was assessed by flow cytometry using a BD FACSArray (FIG. 5). The expression of the fluorescence marker is plotted on the horizontal axis against the antibody binding on the vertical axis. A commercially available mouse anti-CLDN6 IgG2b antibody (R&D, MAB3656) served as a positive control and the antibody obtainable from Sigma under the product number M8894 served as an isotype control.

Antibodies in the supernatants from the monoclonal hybridoma subclones F3-6C3-H2, F3-6C3-H8, F3-6C3-H9, F3-6C3-D8 and F3-6C3-G4, all derived from hybridoma F3-6C3, were specific for CLDN6 and did not bind to CLDN9, CLDN3 and CLDN4. FIG. 5A exemplarily shows the results for the monoclonal hybridoma subclone F3-6C3-H8. Antibodies in the supernatant from the monoclonal hybridoma subclone F3-6C3-H8 also bind to cells transfected with the (I143V)-SNP variant of CLDN6. Antibodies in the supernatant from the monoclonal hybridoma subclone F4-4F7-F2 bind to both CLDN6 and CLDN9 (FIG. 5A). Antibodies in the supernatant from the monoclonal hybridoma subclone F3-7B3-B4 bind to CLDN6, CLDN3 and CLDN9 (FIG. 5B). Antibodies in the supernatant from the monoclonal hybridoma subclone F3-3F7-A5 bind to CLDN6, CLDN4 and CLDN9 (FIG. 5B).

Example 6: Generation and Testing of Monoclonal Antibodies Against CLDN6 a. Generation of Expression Vectors Encoding the Extracellular Domain 1 of CLDN6

A codon-optimized DNA sequence (SEQ ID NO: 12) coding for the putative extracellular domain 1 (EC1) fragment of CLDN6 (SEQ ID NO: 7) as a fusion with an N-terminal Ig kappa leader derived signal peptide followed by 4 additional amino acids to ensure a correct signal peptidase cleavage site (SEQ ID NO: 13) was prepared and cloned into the pcDNA3.1/myc-His vector yielding the vector p3973. Prior to immunization, expression of the EC1 fragment was confirmed by immunofluorescence microscopy on transiently transfected and paraformaldehyde (PFA)-fixed CHO-K1 cells using a commercially available anti-myc antibody (Cell Signaling, MAB 2276).

b. Immunization

Balb/c mice were immunized with 25 μg of p3973 plasmid DNA together with 4 μl PEI-mannose (PEI-Man; in vivo-jetPEI™-Man from PolyPlus Transfection) (150 mM PEI-Man in H$_2$O with 5% glucose) by intraperitoneal injection on days 0 and 14. On days 28 and 44 mice were immunized subcutaneously with KLH-conjugated peptides SEQ ID NO: 14 and SEQ ID NO: 15 (100 μg each in PBS, JPT Peptide Technologies GmbH, Germany) together with HPLC-purified PTO-CpG-ODN (25 μg in PBS; 5'-TCCAT-GACGTTCCTGACGTT; Eurofins MWG Operon, Germany). On days 64, 77 and 97 mice were immunized by intraperitoneal injection with 2×10$^7$ P3X63Ag8U.1 myeloma cells transfected with p3953 vector to stably express CLDN6. Prior to administration, cells were treated with mitomycin-C (2.5 μg/ml, Sigma-Aldrich, M4287). On days 64 and 97 cells were administered together with HPLC-purified PTO-CpG-ODN (50 μg in PBS), on day 77 together with incomplete Freund's adjuvant.

For generation of monoclonal antibodies, mice with detectable anti-CLDN6 immune responses were boosted four days prior to splenectomy by intraperitonal injection of $2\times10^7$ HEK293 cells stably transfected with p3953 vector.

c. Testing of Monoclonal Antibodies Against CLDN6

Flow Cytometry

To test the binding of monoclonal antibodies to CLDN6 and its homologous HEK293T cells were transiently transfected with the corresponding claudin-coding plasmid and the expression was analyzed by flow cytometry. In order to differentiate between transfected and non-transfected cells, HEK293T cells were co-transfected with a fluorescence marker as a reporter. 24 h post transfection cells were harvested with 0.05% trypsin/EDTA, washed with FACS buffer (PBS containing 2% FCS and 0.1% sodium azide) and resuspended in FACS buffer at a concentration of $2\times10^6$ cells/ml. 100 μl of the cell suspension were incubated with the appropriate antibody at indicated concentrations for 30 min at 4° C. A cross-reactive antibody was used to detect CLDN6 and CLDN9 expression. The commercially available mouse anti-claudin antibodies anti-CLDN3 (R&D, MAB4620) and anti-CLDN4 (R&D, MAB4219) served as positive controls, whereas mouse IgG2a (Sigma, M9144) and IgG2b (Sigma, M8894), respectively, served as isotype control. The cells were washed three times with FACS buffer and incubated with an APC-conjugated anti-mouse IgG 1+2a+2b+3a specific secondary antibody (Dianova, 115-135-164) for 30 min at 4° C. The cells were washed twice and resuspended in FACS buffer. The binding was analyzed by flow cytometry using a BD FACSArray. The expression of the fluorescence marker was plotted on the horizontal axis against the antibody binding on the vertical axis.

CDC

The complement dependent cytotoxicity (CDC) was determined by measuring the content of intracellular ATP in non-lysed cells after the addition of human complement to the target cells incubated with anti-CLDN6 antibodies. As a very sensitive analytical method the luminescent reaction of luciferase was used for measuring ATP.

CHO-K1 cells stably transfected with CLDN6 (CHO-K1-CLDN6) were harvested with 0.05% trypsin/EDTA, washed twice with X-Vivo 15 medium (Lonza, BE04-418Q) and suspended at a concentration of $1\times10^7$ cells/ml in X-Vivo 15 medium. 250 μl of the cell suspension were transferred into a 0.4 cm electroporation cuvette and mixed with 7 μg of in vitro transcribed RNA encoding for luciferase (luciferase IVT RNA). The cells were electroporated at 200 V and 300 μF using a Gene Pulser Xcell (Bio Rad). After electroporation, the cells were suspended in 2.4 ml pre-warmed D-MEM/F12 (1:1) with GlutaMax-I medium (Invitrogen, 31331-093) containing 10% (v/v) FCS, 1% (v/v) penicillin/streptomycin and 1.5 mg/ml G418. 50 μl of the cell suspension per well were seeded into a white 96-well PP-plate and incubated at 37° C. and 7.5% $CO_2$. 24 h post electroporation 50 μl monoclonal murine anti-CLDN6 antibodies in 60% RPMI (containing 20 mM HEPES) and 40% human serum (serum pool obtained from six healthy donors) were added to the cells at indicated concentrations. 10 μl 8% (v/v) Triton X-100 in PBS per well were added to total lysis controls, whereas 10 μl PBS per well were added to max viable cells controls and to the actual samples. After an incubation of 80 min at 37° C. and 7.5% $CO_2$ 50 μl luciferin mix (3.84 mg/ml D-luciferin, 0.64 U/ml ATPase and 160 mM HEPES in $ddH_2O$) were added per well. The plate was incubated in the dark for 45 min at RT. The luminescence was measured using a luminometer (Infinite M200, TECAN). Results are given as integrated digital relative light units (RLU).

NEC8 cells were electroporated at 200 V and 400 μF and cultivated in RPMI 1640 with GlutaMAX-I medium (Invitrogen, 61870) containing 10% (v/v) FCS.

The specific lysis is calculated as:

$$\text{specific lysis } [\%] = 100 - \left[ \frac{(\text{sample} - \text{total lysis})}{(\text{max viable cells} - \text{total lysis})} \times 100 \right]$$

max viable cells: 10 μl PBS, without antibody total lysis: 10 μl 8% (v/v) Triton X-100 in PBS, without antibody Early Treatment For early antibody treatments $2\times10^7$ NEC8 cells in 200 μl PBS were subcutaneously inoculated into the flank of athymic Nude-Foxn1$^{nu}$ mice. Each experimental group consisted of ten 6-8 week-old female mice. Three days after inoculation 200 μg of purified murine monoclonal antibodies muMAB 59A, 60A, 61D, 64A, 65A, 66B and 67A were applied for 46 days by alternating intravenous and intraperitoneal injections twice a week. Experimental groups treated with PBS served as a negative controls. The tumor volume (TV=(length×width$^2$)/2) was monitored bi-weekly. TV is expressed in mm$^3$, allowing construction of tumor growth curves over time. When the tumor reached a volume greater than 1500 mm$^3$ mice were killed.

d. Results

Murine monoclonal antibodies muMAB 59A, 60A, 61D, 64A, 65A, 66B and 67A showed strong binding to human CLDN6 and the CLDN6 SNP (single nucleotide polymorphism) variant I143V while no binding to CLDN3, 4, and 9 was observed (FIG. 6).

MuMAB 59A, 60A, 61D, 64A, 65A, 66B and 67A exhibited very low EC50 values (EC50 200-500 ng/ml) and saturation of binding was achieved at low concentrations (FIG. 7).

MuMAB 59A, 60A, 61D, 64A, 65A, 66B and 67A exhibited dose-dependent CDC activity and induced CDC at low concentrations (FIG. 8). The anti-CLDN6 antibodies muMAB 65A and 66B induced CDC on NEC8 cells in a dose dependent manner (FIG. 9). Target specificity of muMAB 65A and 66B was proved by using NEC8 LVTS2 54 cells (CLDN6 knock-down).

Furthermore, muMAB 59A, 60A, 61D, 64A, 65A, 66B and 67A showed tumor growth inhibition in mice engrafted with NEC8 cells (FIG. 10).

Example 7: Generation and Testing of Chimeric Monoclonal Antibodies Against CLDN6 a. Generation of Mouse/Human Chimeric Monoclonal Antibodies

For chimerization, the murine heavy chain and light chain variable region including leader sequences were amplified by PCR using primers listed in the table below. The murine heavy chains were fused by an ApaI restriction site (5'-GGGCCC-3') to the N-terminal part of the human Fcgamma1 chain, which was encoded by the expression vector. Variable domains of the murine kappa chain including leader sequences were cloned in front of the constant region using a BsiWI restriction site. The correct orientation of the constant region in the vector, i.e. suitable for the preceeding promoter of the vector, was verified by sequencing. Due to the position of the ApaI restriction site, any amplification of a variable region including leader sequence for this purpose has to include the first 11 nucleotides of the sequence of the human gamma-1 constant region in addition to the sequence of the ApaI site. The nucleotide sequence of human gamma-1 heavy chain constant region is listed as SEQ ID NO: 24, the amino acid sequence of the thus expressed human gamma-1 constant region is listed as SEQ ID NO: 25. The nucleotide sequence encoding the constant part of the kappa light chain is listed as SEQ ID NO: 26, the respective amino acid sequence is listed as SEQ ID NO: 27.

TABLE 1

Mouse hybridoma cell lines used for antibody cloning

|  | muMAB | Isotype | Primer SEQ ID NOs: |
|---|---|---|---|
| heavy chain | 64A | IgG2a | 17, 18 |
|  | 89A | IgG2a | 17, 19 |
|  | 61D | IgG2a | 17, 20 |
|  | 67A | IgG2a | 17, 20 |
| light chain | 64A | IgK | 21, 22 |
|  | 89A | IgK | 21, 23 |
|  | 61D | IgK | 21, 22 |
|  | 67A | IgK | 21, 22 |

Corresponding to their murine counterparts the chimeric monoclonal antibodies were named adding the prefix "chim", e.g. chimAB 64A.

Amplification of the murine variable regions of light and heavy chains including leader sequences was carried out according to the "step-out PCR" method described in Matz et al. (Nucleic Acids Research, 1999, Vol. 27, No. 6). For this, total RNA was prepared from monoclonal hybridoma cell lines (see Tab. 1) by standard methods known to those skilled in the art, for example with the use of RNeasy Mini Kit (Qiagen). Single stranded cDNA was prepared according to the "template-switch" method also described in Matz et al. (Nucleic Acids Research, 1999, Vol. 27, No. 6, 1558). In addition to a (dT)30 oligomer (SEQ ID NO: 28), it included a DNA/RNA hybrid oligomer (SEQ ID NO: 29) serving as an 5' adaptor for template switching during polymerization of the cDNA strand. In this adaptor oligomer the last three nucleotides were ribo-instead of deoxyribonucleotides. The subsequent "step-out PCR" used an antisense oligomer targeted to the constant region of the mouse kappa chain or to the constant region of the subclass 2a of the gamma chain (SEQ ID NO: 30 and 31, respectively). The IgG subclass of the murine monoclonal antibody produced by the hybridoma cell lines was afore immunologically analyzed with IsoStrip (Roche), and the appropriate antisense oligomer was chosen accordingly (see Tab. 1). A primer mix served as the sense oligomer in the "step-out PCR", comprising the two oligomers listed in SEQ ID NO: 32 and 33.

The identified murine variable regions including leader sequences were then amplified by PCR omitting the 5' UTR and the 3' mouse constant region, adding restriction sites to the ends which allowed subcloning into the prepared expression vectors carrying the human constant regions. In addition, the sense oligomers provided a consensus Kozak sequence (5'-GCCGCCACC-3') and the antisense oligomers for heavy chain variable regions included the first 11 nucleotides of the human gamma-1 constant region in addition to the ApaI restriction site (see Tab. 1, SEQ ID NOs: 17 to 23). Kappa light chain variable regions including leader sequences were cloned using HindIII and BsiWI restriction enzymes, gamma heavy chain variable regions demanded HindIII and ApaI restriction enzymes.

Further murine variable regions of light and heavy chains including leader sequences were amplified and further chimeric monoclonal antibodies against CLDN6 generated in accordance to the protocol disclosed above.

b. Production of Chimeric Monoclonal Anti-CLDN6 Antibodies

Chimeric monclonal antibodies were transiently expressed in HEK293T cells (ATCC CRL-11268) transfected with plasmid DNA coding for the light and heavy chains of the corresponding antibody. 24 h before transfection $8 \times 10^7$ cells were seeded on 145 mm cell culture plates and cultivated in 25 ml HEK293T-medium (DMEM/F12+ GlutaMAX-I, 10% FCS, 1% penicillin/streptomycin). 20 µg plasmid DNA were dissolved in 5 ml HEK293T-medium without supplements per cell culture plate. After adding 75 µl linear polyethylenimine (PEI) (1 mg/ml) (Polyscience, 23966) the (DNA:PEI)-mixture was incubated 15 min at RT. Thereafter, the transfection-mix was added dropwise to the cells. 24 h post transfection the HEK293T-medium was replaced with Pro293a-medium (Lonza, BE12-764Q) containing 1% penicillin/streptomycin. For optimal expression, the transfected cells were cultivated at 37° C. and 7.5% $CO_2$ for additional 96 to 120 h. The supernatant was harvested and the chimeric antibody was purified by FPLC using protein-A columns. The concentration of the antibody was determined and quality was tested by SDS-PAGE.

c. Testing of Chimeric Monoclonal Antibodies Against CLDN6

Flow Cytometry

To test the specificities and affinities of CLDN6-specific chimeric monoclonal antibodies binding to HEK293 cells stably transfected with CLDN3, 4, 6 or 9, respectively, and tumor cell lines that endogenously express CLDN6 was analyzed by flow cytometry. Therefore, cells were harvested with 0.05% Trypsin/EDTA, washed with FACS buffer (PBS containing 2% FCS and 0.1% sodium azide) and resuspended in FACS buffer at a concentration of $2 \times 10^6$ cells/ml. 100 µl of the cell suspension were incubated with the appropriate antibody at indicated concentrations for 60 min at 4° C. A chimeric cross-reactive antibody (chimAB 5F2D2) was used to detect CLDN6 and CLDN9 expression. The commercially available mouse anti-claudin antibodies anti-CLDN3 (R&D, MAB4620) and anti-CLDN4 (R&D, MAB4219) served as positive controls, whereas human IgG1-kappa (Sigma, 15154) served as a negative control. The cells were washed three times with FACS buffer and incubated for 30 min at 4° C. with an APC-conjugated goat anti-human IgG Fc-gamma (Dianova, 109-136-170) or an APC-conjugated anti-mouse IgG 1+2a+2b+3a (Dianova, 115-135-164) specific secondary antibody, respectively. The cells were washed twice and resuspended in FACS buffer. The binding was analyzed by flow cytometry using a BD FACSArray.

CDC

The complement dependent cytotoxicity (CDC) was determined by measuring the content of intracellular ATP in non-lysed cells after the addition of human complement to the target cells incubated with anti-CLDN6 antibodies. As a very sensitive analytical method the bioluminescent reaction of luciferase is used for measuring ATP.

In this assay, NEC8 wildtype cells (CLDN6 positive) and NEC8 CLDN6 knock-down cells (CLDN6 negative) were used which both were stably transduced with luciferase expression construct. The cells were harvested with 0.05% Trypsin/EDTA and adjusted to a concentration of $2 \times 10^5$ cells/ml in RPMI with GlutaMax-I medium (Invitrogen, 61870-010) containing 10% (v/v) FCS. $1 \times 10^4$ cells were seeded into a white 96-well PP-plate and incubated for 24 h at 37° C. and 5% $CO_2$. After incubation, 50 µl monoclonal chimeric anti-CLDN6 antibodies in 60% RPMI (containing 20 mM HEPES) and 40% human serum (serum pool obtained from six healthy donors) were added to the cells at indicated concentrations. 10 µl 8% (v/v) Triton X-100 in PBS per well were added to total lysis controls, whereas 10 µl PBS per well were added to max viable cells controls and to the actual samples. After a further incubation of 80 min at 37° C. and 5% $CO_2$ 50 µl luciferin mix (3.84 mg/ml D-luciferin, 0.64 U/ml ATPase and 160 mM HEPES in dd$H_2O$) was added per well. The plate was incubated in the dark at RT for 45 min. The bioluminescence was measured using a luminometer (Infinite M200, TECAN). Results are given as integrated digital relative light units (RLU).

The specific lysis is calculated as:

$$\text{specific lysis } [\%] = 100 - \left[ \frac{(\text{sample} - \text{total lysis})}{(\text{max viable cells} - \text{total lysis})} \times 100 \right]$$

max viable cells: 10 µl PBS, without antibody total lysis: 10 µl 8% (v/v) Triton X-100 in PBS, without antibody

ADCC

The antibody dependent cellular cytotoxicity (ADCC) was determined by measuring the content of intracellular ATP in non-lysed cells after the addition of human PBMC to the target cells incubated with anti-CLDN6 antibodies. As a very sensitive analytical method the bioluminescent reaction of luciferase is used for measuring ATP.

In this assay, NEC-8 wildtype cells (CLDN6 positive) and NEC-8 CLDN6 knock-down cells (CLDN6 negative) were used which both were stably transduced with luciferase expression construct. The cells were harvested with 0.05% Trypsin/EDTA and adjusted to a concentration of $2 \times 10^5$ cells/ml in RPMI with GlutaMax-I medium (Invitrogen, 61870-010) containing 10% (v/v) FCS and 20 mM Hepes. $1 \times 10^4$ cells were seeded into a white 96-well PP-plate and incubated 4 h at 37° C. and 5% $CO_2$.

PBMC were isolated from human donor blood samples by density gradient centrifugation using Ficoll Hypaque (GE Healthcare, 17144003). The PMBC containing interphase was isolated and cells were washed twice with PBS/EDTA (2 mM). $1 \times 10^8$ PBMC were seeded in 50 ml X-Vivo 15 medium (Lonza, BE04-418Q) containing 5% heat-inactivated human serum (Lonza, US14-402E) and incubated for 2 h at 37° C. and 5% $CO_2$.

4 h post seeding of the target cells (NEC-8) 25 µl monoclonal chimeric anti-CLDN6 antibodies in PBS were added to the cells at indicated concentrations. Nonadherent PBMC, which separated within the 2 h incubation from adherent monocytes, were harvested and adjusted to $8 \times 10^6$ cells/ml in X-vivo 15 medium. 25 µl of this cell suspension was added to the target cells and the monoclonal chimeric anti-CLDN6 antibodies. The plates were incubated for 24 h at 37° C. and 5% $CO_2$.

After the 24 h incubation 10 µl 8% (v/v) Triton X-100 in PBS per well were added to total lysis controls, whereas 10 µl PBS per well were added to max viable cells controls and to the actual samples. 50 µl luciferin mix (3.84 mg/ml D-luciferin, 0.64 U/ml ATPase and 160 mM HEPES in dd$H_2O$) was added per well. The plate was incubated in the dark at RT for 30 min. The bioluminescence was measured using a luminometer (Infinite M200, TECAN). Results are given as integrated digital relative light units (RLU).

The specific lysis is calculated as:

$$\text{specific lysis } [\%] = 100 - \left[ \frac{(\text{sample} - \text{total lysis})}{(\text{max viable cells} - \text{total lysis})} \times 100 \right]$$

max viable cells: 10 µl PBS, without antibody total lysis: 10 µl 8% (v/v) Triton X-100 in PBS, without antibody d. Results Anti-CLDN6 chimeric monoclonal antibodies chimAB 61D, 64A, 67A and 89A showed strong binding to human CLDN6 while no binding to CLDN3, 4, and 9 was observed (FIG. 11).

Regarding binding to human CLDN6 stably expressed on the surface of HEK293 cells, anti-CLDN6 chimeric monoclonal antibodies chimAB 64A and 89A exhibit very low EC50 values (EC50 450-600 ng/ml) and saturation of binding was achieved at low concentrations. ChimAB 67A and 61D showed low (EC50 1000 ng/ml) and medium (EC50 2300 ng/ml) EC50 values, respectively (FIG. 12).

Regarding binding to CLDN6 endogenously expressed in NEC8 cells, anti-CLDN6 chimeric monoclonal antibodies chimAB 64A and 89A exhibited very low EC50 values (EC50 600-650 ng/ml) and saturation of binding was achieved at low concentrations, whereas chimAB 61D and 67A showed medium (EC50 1700 ng/ml) and high (EC50 6100 ng/ml) EC50 values, respectively (FIG. 13).

Regarding binding to CLDN6 endogenously expressed in OV90 cells, anti-CLDN6 chimeric monoclonal antibodies chimAB 64A and 89A exhibited very low EC50 values (EC50 550-600 ng/ml) and saturation of binding was achieved at low concentrations. ChimAB 61D and 67A showed medium EC50 values (EC50 1500 ng/ml and EC50 2300 ng/ml, respectively) (FIG. 14).

Anti-CLDN6 chimeric monoclonal antibodies chimAB 61D, 64A, 67A and 89A exhibited CDC activity in a dose-dependent manner on NEC-8 cells (FIG. 15).

Anti-CLDN6 chimeric monoclonal antibodies chimAB 61D, 64A, 67A and 89A exhibited dose-dependent ADCC activity on NEC-8 cells and induced ADCC even at low antibody concentrations (FIG. 16).

These results clearly show the specificity of these chimeric monoclonal antibodies for CLDN6.

Example 8: Treatment Using Monoclonal Antibodies Against CLDN6

Early Treatment

For early antibody treatments $2 \times 10^7$ NEC8 cells in 200 µl RPMI medium (Gibco) were subcutaneously inoculated into the flank of athymic Nude-Foxn1$^{nu}$ mice. Each experimental group consisted of ten 6-8 week-old female mice. Three days after tumor cell inoculation 200 of purified murine monoclonal antibody muMAB 89A was applied for seven weeks by alternating intravenous and intraperitoneal injections twice a week. Experimental group treated with PBS served as negative control. The tumor volume (TV=length× width$^2$/2) was monitored bi-weekly. TV is expressed in mm$^3$, allowing construction of tumor growth curves over time. When the tumors reached a volume greater than 1500 mm$^3$ mice were sacrificed.

Advanced Treatments

For antibody treatments of advanced xenograft tumors $2 \times 10^7$ NEC8 cells in 200 µl RPMI medium (Gibco) were subcutaneously inoculated into the flank of 6-8 week-old female athymic Nude-Foxn1$^{nu}$ mice. The tumor volume (TV=(length×width$^2$)/2) was monitored bi-weekly. TV is expressed in mm$^3$, allowing construction of tumor growth curves over time. 15 to 17 days after tumor cell inoculation mice were divided into treatment groups of eight animals per cohorte with homogenous tumor sizes of above 80 mm$^3$. 200 µg of purified murine monoclonal antibodies muMAB 61D, 64A, 67A and 89A were applied for five weeks by alternating intravenous and intraperitoneal injections twice a week. Experimental groups treated with PBS and an unspecific antibody served as negative controls. When the tumors reached a volume bigger than 1500 mm$^3$ mice were sacrificed.

In an early treatment xenograft model using mice engrafted with the tumor cell line NEC8, mice treated with murine monoclonal antibodies muMAB 61D, 64A and 67A did not show any tumor growth even after stopping the immunotherapy (FIG. 17).

In an early treatment xenograft model using mice engrafted with the tumor cell line NEC8, muMAB 89A showed tumor growth inhibition and no tumors were detectable in mice treated with muMAB89A at the end of the study (FIG. 18).

In an advanced treatment xenograft model using mice engrafted with the tumor cell line NEC8, muMAB 64A showed an inhibition of tumor growth (FIG. 19).

In an advanced treatment xenograft model using mice engrafted with the tumor cell line NEC8, mice treated with muMAB 64A showed prolonged survival (FIG. 20).

In an advanced treatment xenograft model using mice engrafted with the tumor cell line NEC8, inhibition of tumor growth was achieved with the murine monoclonal anti-CLDN6 antibodies muMAB 61D, 67A and 89A (FIG. 21).

In an advanced treatment xenograft model using mice engrafted with the tumor cell line NEC8, mice treated with the CLDN6 specific antibody muMAB 61D or 67A showed prolonged survival (FIG. 22).

In an advanced treatment xenograft model using mice engrafted with NEC8 wildtype and NEC8 cells with a stable CLDN6 knock-down, muMAB 64A and 89A only show a therapeutic effect in mice engrafted with NEC8 wildtype but not in mice engrafted with NEC8 CLDN6 knock-down cells demonstrating CLDN6-specificity of the antibody in vivo (FIG. 23).

Example 9: High-Resolution Eitope Mapping of Monoclonal Antibodies Against CLDN6

The CLDN6 specific monoclonal antibodies only show very weak (if any) binding to linear peptides in ELISA epitope-mapping studies, implying that their epitopes are conformational. To analyze the interaction between antibodies described herein and CLDN6 in its native conformation site-directed mutagenesis in mammalian cell culture was used as an epitope-mapping technique. Alanine scanning mutagenesis of amino acids 27-81 and 137-161 within the first and second extracellular domain, respectively, was performed. Following transient expression in HEK293T cells, CLDN6 mutants were assessed for their ability to be bound by specific monoclonal antibodies. Impaired binding of a specific monoclonal antibody to a CLDN6 mutant suggest that the mutated amino acid is an important contact and/or conformational residue. The binding was analyzed by flow cytometry. To discriminate between transfected and non-transfected cell populations, cells were co-transfected with a fluorescence marker.

The amino acid residues of CLDN6 that are important for the interaction with CLDN6 specific chimeric antibodies have been systematically identified by alanine-scanning. Alanine and glycine mutations were generated by site-directed mutagenesis (GENEART AG, Germany). To test the binding of monoclonal chimeric antibodies to wild-type CLDN6 and its mutants HEK293T cells were transiently transfected with the corresponding claudin-coding plasmid and the expression was analyzed by flow cytometry. In order to differentiate between transfected and non-transfected cells, HEK293T cells were co-transfected with a fluorescence marker as a reporter. 24 h post transfection cells were harvested with 0.05% Trypsin/EDTA, washed with FACS buffer (PBS containing 2% FCS and 0.1% sodium azide) and resuspended in FACS buffer at a concentration of 2×10$^6$ cells/ml. 100 µl of the cell suspension were incubated with 10 µg/ml antibody for 45 min at 4° C. The commercially available mouse anti-CLDN6 (R&D, MAB3656) was used as a control to detect cell-surface expression of CLDN6 mutants. The cells were washed three times with FACS buffer and incubated with an APC-conjugated goat anti-human IgG Fc-gamma (Dianova, 109-136-170) or an APC-conjugated anti-mouse IgG 1+2a+2b+3a specific secondary antibody (Dianova, 115-135-164) for 30 min at 4° C. The cells were washed twice and resuspended in FACS buffer. The binding within the transfected cell population was analyzed by flow cytometry using a BD FACSArray. Therefore, the expression of the fluorescence marker was plotted on the horizontal axis against the antibody binding on the vertical axis. The average signal intensity of a monoclonal chimeric CLDN6 specific antibody bound to mutant CLDN6 was expressed as the percentage of wild-type binding. Amino acids that are essential for binding showed no binding after being mutated whereas amino acids that support binding only showed reduced binding compared to wild-type.

High resolution epitope-mapping demonstrated that the amino acids F35, G37, S39 and possibly T33 of the first extracellular domain of CLDN6 are important for the interaction with the CLDN6 specific chimeric antibodies chimAB 61D, 64A, 67A and 89A. Residue 140 is essential for the binding of chimAB 89A and it contributes to the binding of chimAB 61D and 67A. In addition, L151 of the second extracellular domain of CLDN6 is important for the interaction with chimAB 67A (FIG. 24).

The invention claimed is:

1. A bispecific antibody comprising a first antigen binding site having a binding specificity for CLDN6 and a second antigen binding site having a binding specificity for a second target epitope,
   wherein the first antigen binding site comprises a set of heavy chain CDR (HCDR) and light chain CDR (LCDR) selected from the group consisting of:
   a. a HCDR1 of amino acid sequence GYSFTGYT (SEQ ID NO: 47),
      a HCDR2 of amino acid sequence INPYNGGT (SEQ ID NO: 54),
      a HCDR3 of amino acid sequence ARDYGYVLDY (SEQ ID NO: 55),
      a LCDR1 of amino acid sequence SSVSY (SEQ ID NO: 56),
      a LCDR2 of amino acid sequence STS (SEQ ID NO: 53), and
      a LCDR3 of amino acid sequence QQRSIYPPWT (SEQ ID NO: 57);
   b. a HCDR1 of amino acid sequence GYSFTGYT (SEQ ID NO: 47),
      a HCDR2 of amino acid sequence INPYNGGT (SEQ ID NO: 54),
      a HCDR3 of amino acid sequence ARDYGFVLDY (SEQ ID NO: 58),
      a LCDR1 of amino acid sequence SSVSY (SEQ ID NO: 56),
      a LCDR2 of amino acid sequence STS (SEQ ID NO: 53), and
      a LCDR3 of amino acid sequence QQRSNYPPWT (SEQ ID NO: 59);
   c. a HCDR1 of amino acid sequence GYSFTGYT (SEQ ID NO: 47),
      a HCDR2 of amino acid sequence INPYNGGI (SEQ ID NO: 60),
      a HCDR3 of amino acid sequence ARDFGYVLDY (SEQ ID NO: 61),
      a LCDR1 of amino acid sequence SSVSY (SEQ ID NO: 56),
      a LCDR2 of amino acid sequence STS (SEQ ID NO: 53), and
      a LCDR3 of amino acid sequence QQRSTYPPWT (SEQ ID NO: 62); and
   d. a HCDR1 of amino acid sequence GYSFTGYT (SEQ ID NO: 47),
      a HCDR2 of amino acid sequence INPYNGGS (SEQ ID NO: 63),
      a HCDR3 of amino acid sequence ARDYGYVFDY (SEQ ID NO: 64),
      a LCDR1 of amino acid sequence SSVNY (SEQ ID NO: 65),
      a LCDR2 of amino acid sequence STS (SEQ ID NO: 53), and
      a LCDR3 of amino acid sequence QQRNNYPPWT (SEQ ID NO: 66); and wherein the second target epitope is selected from the group consisting of human Fc-gammaRI (CD64), human Fc-alpha receptor (CD89), and CD3.

2. The bispecific antibody of claim 1, wherein the first antigen binding site is not capable of detectably binding to at least one of (i) CLDN3 associated with the surface of a cell that expresses CLDN3, (ii) CLDN4 associated with the surface of a cell that expresses CLDN4, or (iii) CLDN9 associated with the surface of a cell that expresses CLDN9.

3. The bispecific antibody of claim 1, wherein CLDN6 has the amino acid sequence of SEQ ID NO: 2 or the amino acid sequence of SEQ ID NO: 8.

4. The bispecific antibody of claim 1, wherein the second target epitope is selected from the group consisting of an Fc receptor and a T cell receptor.

5. The bispecific antibody of claim 1, wherein the second target epitope is CD3.

6. The bispecific antibody of claim 1, wherein the first antigen binding site comprises:
a HCDR1 of amino acid sequence GYSFTGYT (SEQ ID NO: 47),
a HCDR2 of amino acid sequence INPYNGGT (SEQ ID NO: 54),
a HCDR3 of amino acid sequence ARDYGYVLDY (SEQ ID NO: 55),
a LCDR1 of amino acid sequence SSVSY (SEQ ID NO: 56),
a LCDR2 of amino acid sequence STS (SEQ ID NO: 53), and
a LCDR3 of amino acid sequence QQRSIYPPWT (SEQ ID NO: 57).

7. The bispecific antibody of claim 6, wherein the first antigen binding site comprises a heavy chain variable region having an amino acid sequence of SEQ ID NO: 34 and a light chain variable region having an amino acid sequence of SEQ ID NO: 35.

8. The bispecific antibody of claim 7, wherein the second target epitope is CD3.

9. The bispecific antibody of claim 1, wherein the first antigen binding site comprises:
a HCDR1 of amino acid sequence GYSFTGYT (SEQ ID NO: 47),
a HCDR2 of amino acid sequence INPYNGGT (SEQ ID NO: 54),
a HCDR3 of amino acid sequence ARDYGFVLDY (SEQ ID NO: 58),
a LCDR1 of amino acid sequence SSVSY (SEQ ID NO: 56),
a LCDR2 of amino acid sequence STS (SEQ ID NO: 53), and
a LCDR3 of amino acid sequence QQRSNYPPWT (SEQ ID NO: 59).

10. The bispecific antibody of claim 9, wherein the first antigen binding site comprises a heavy chain variable region having an amino acid sequence of SEQ ID NO: 36 and a light chain variable region having an amino acid sequence of SEQ ID NO: 37.

11. The bispecific antibody of claim 10, wherein the second target epitope is CD3.

12. The bispecific antibody of claim 1, wherein the first antigen binding site comprises:
a HCDR1 of amino acid sequence GYSFTGYT (SEQ ID NO: 47),
a HCDR2 of amino acid sequence INPYNGGI (SEQ ID NO: 60),
a HCDR3 of amino acid sequence ARDFGYVLDY (SEQ ID NO: 61),
a LCDR1 of amino acid sequence SSVSY (SEQ ID NO: 56),
a LCDR2 of amino acid sequence STS (SEQ ID NO: 53), and
a LCDR3 of amino acid sequence QQRSTYPPWT (SEQ ID NO: 62).

13. The bispecific antibody of claim 12, wherein the first antigen binding site comprises a heavy chain variable region having an amino acid sequence of SEQ ID NO: 38 and a light chain variable region having an amino acid sequence of SEQ ID NO: 39.

14. The bispecific antibody of claim 13, wherein the second target epitope is CD3.

15. The bispecific antibody of claim 1, wherein the first antigen binding site comprises:
a HCDR1 of amino acid sequence GYSFTGYT (SEQ ID NO: 47),
a HCDR2 of amino acid sequence INPYNGGS (SEQ ID NO: 63),
a HCDR3 of amino acid sequence ARDYGYVFDY (SEQ ID NO: 64),
a LCDR1 of amino acid sequence SSVNY (SEQ ID NO: 65),
a LCDR2 of amino acid sequence STS (SEQ ID NO: 53), and
a LCDR3 of amino acid sequence QQRNNYPPWT (SEQ ID NO: 66).

16. The bispecific antibody of claim 15, wherein the first antigen binding site comprises a heavy chain variable region having an amino acid sequence of SEQ ID NO: 40 and a light chain variable region having an amino acid sequence of SEQ ID NO: 41.

17. The bispecific antibody of claim 16, wherein the second target epitope is CD3.

18. The bispecific antibody of claim 1, wherein the bispecific antibody is a diabody.

19. A pharmaceutical composition comprising the bispecific antibody of claim 1.

* * * * *